(12) United States Patent
Liu et al.

(10) Patent No.: US 7,893,244 B2
(45) Date of Patent: Feb. 22, 2011

(54) COMPOSITION AND METHODS OF RNAI THERAPEUTICS FOR TREATMENT OF CANCER AND OTHER NEOVASCULARIZATION DISEASES

(75) Inventors: Yijia Liu, Gaithersburg, MD (US); Patrick Y. Lu, Rockville, MD (US); Martin C. Woodle, Bethesda, MD (US); Frank Y. Xie, Germantown, MD (US)

(73) Assignee: Intradigm Corporation, Palo Alto, CA (US)

( * ) Notice: Subject to any disclaimer, the term of this patent is extended or adjusted under 35 U.S.C. 154(b) by 0 days.

(21) Appl. No.: 12/069,349

(22) Filed: Feb. 8, 2008

(65) Prior Publication Data

US 2009/0203894 A1 Aug. 13, 2009

Related U.S. Application Data

(63) Continuation-in-part of application No. 11/824,084, filed on Jun. 29, 2007, which is a continuation of application No. PCT/US2006/013645, filed on Apr. 12, 2006.

(60) Provisional application No. 60/670,717, filed on Apr. 12, 2005, provisional application No. 60/900,858, filed on Feb. 9, 2007.

(51) Int. Cl.
C07H 21/04 (2006.01)
C07H 21/02 (2006.01)
A61K 48/00 (2006.01)

(52) U.S. Cl. .................. 536/24.5; 536/23.1; 514/44

(58) Field of Classification Search ................. None
See application file for complete search history.

(56) References Cited

U.S. PATENT DOCUMENTS

| | | | |
|---|---|---|---|
| 5,240,848 A | 8/1993 | Keck et al. | |
| 5,332,671 A | 7/1994 | Ferrara et al. | |
| 5,607,918 A | 3/1997 | Eriksson et al. | |
| 5,840,693 A | 11/1998 | Eriksson et al. | |
| 6,013,780 A | 1/2000 | Neufeld | |
| 6,140,073 A | 10/2000 | Bayne et al. | |
| 6,150,092 A | 11/2000 | Uchida et al. | |
| 6,187,822 B1 | 2/2001 | Leibovich | |
| 6,331,301 B1 | 12/2001 | Eriksson et al. | |
| 6,346,398 B1 | 2/2002 | Pavco et al. | |
| 6,352,975 B1 | 3/2002 | Schreiner et al. | |
| 6,395,707 B1 | 5/2002 | Zioncheck et al. | |
| 6,475,796 B1 | 11/2002 | Pollitt et al. | |
| 6,479,654 B1 | 11/2002 | Baird et al. | |
| 6,479,729 B1 | 11/2002 | Campochiaro et al. | |
| 6,485,942 B1 | 11/2002 | Zioncheck et al. | |
| 6,503,886 B1 | 1/2003 | Baird et al. | |
| 6,506,884 B1 | 1/2003 | Mintz et al. | |
| 6,569,434 B1 | 5/2003 | Bayne et al. | |
| 6,583,276 B1 | 6/2003 | Neufeld et al. | |
| 6,589,782 B1 | 7/2003 | Neufeld et al. | |
| 6,673,549 B1 | 1/2004 | Furness et al. | |
| 6,677,300 B1 | 1/2004 | Schreiner et al. | |
| 6,723,702 B2 | 4/2004 | Conrad et al. | |
| 6,727,066 B2 | 4/2004 | Kaser | |
| 6,743,909 B2 | 6/2004 | Cowsert et al. | |
| 6,750,044 B1 | 6/2004 | Keyt et al. | |
| 6,780,836 B2 | 8/2004 | Unemori | |
| 6,783,954 B2 | 8/2004 | Mintz et al. | |
| 6,783,961 B1 | 8/2004 | Edwards et al. | |
| 6,887,848 B2 | 5/2005 | Pollitt et al. | |
| 6,916,915 B1 | 7/2005 | Freedman et al. | |
| 6,927,779 B2 | 8/2005 | Mannion et al. | |
| 6,933,134 B2 | 8/2005 | Bayne et al. | |
| 6,943,153 B1 | 9/2005 | Manning, Jr. et al. | |
| 6,965,010 B2 | 11/2005 | Alitalo et al. | |
| 6,974,667 B2 | 12/2005 | Horne et al. | |
| 6,979,557 B2 | 12/2005 | Isogai et al. | |
| 7,005,505 B1 | 2/2006 | Keyt et al. | |
| 7,030,083 B2 | 4/2006 | Schreiner et al. | |
| 7,078,382 B1 | 7/2006 | Shen et al. | |
| 7,101,977 B2 | 9/2006 | Rosenblum et al. | |
| 7,115,416 B1 | 10/2006 | Edwards et al. | |

(Continued)

FOREIGN PATENT DOCUMENTS

CN 1834254 9/2006

(Continued)

OTHER PUBLICATIONS

U.S. Appl. No. 12/420,907, filed Apr. 9, 2009, Liu et al.
Shen et al., "Suppression of ocular neovascularization with siRNA targeting VEGF receptor 1," Gene Therapy, 13:225-234 (2006).
United States Patent and Trademark Office, "Notice of Allowance and Fee(s) Due," U.S. Appl. No. 11/824,085, Mar. 9, 2009.
U.S. Appl. No. 12/665,819, filed Dec. 21, 2009, Yang.
United States Patent and Trademark Office, "Notice of Allowance and Fee(s) Due," U.S. Appl. No. 11/824,084, Sep. 17, 2010.

*Primary Examiner*—Amy Bowman
(74) *Attorney, Agent, or Firm*—Ropes & Gray LLP; Jane T. Gunnison; Alla Brukman

(57) ABSTRACT

Compositions and methods are provided for treatment of diseases involving unwanted neovascularization (NV). The invention provides treatments that control NV through selective inhibition of pro-angiogenic biochemical pathways, including inhibition of the VEGF pathway gene expression and inhibition localized at pathological NV tissues. Tissue targeted nanoparticle compositions comprising polymer conjugates and nucleic acid molecules that induce RNA interference (RNAi) are provided. The nanoparticle compositions of the invention can be used alone or in combination with other therapeutic agents such as VEGF pathway antagonists. The compositions and methods can be used for the treatment of NV diseases such as cancer, ocular disease, arthritis, and inflammatory diseases.

29 Claims, 27 Drawing Sheets

U.S. PATENT DOCUMENTS

| | | |
|---|---|---|
| 7,148,342 B2 | 12/2006 | Tolentino et al. |
| 7,176,304 B2 | 2/2007 | McSwiggen et al. |
| 7,345,027 B2 | 3/2008 | Tolentino et al. |
| 7,534,878 B2 | 5/2009 | Liu et al. |
| 7,723,316 B2 | 5/2010 | Liu |
| 7,786,092 B2 | 8/2010 | Liu |
| 2001/0021772 A1 | 9/2001 | Uhlmann et al. |
| 2003/0138407 A1 | 7/2003 | Lu et al. |
| 2004/0018176 A1 | 1/2004 | Tolentino et al. |
| 2004/0142895 A1 | 7/2004 | Lockridge |
| 2005/0019927 A1 | 1/2005 | Hildinger et al. |
| 2005/0075304 A1 | 4/2005 | McSwiggen et al. |
| 2005/0153337 A1 | 7/2005 | Manoharan |
| 2005/0176024 A1 | 8/2005 | McSwiggen et al. |
| 2005/0222066 A1 | 10/2005 | Richards et al. |
| 2006/0094032 A1 | 5/2006 | Fougerolles et al. |
| 2006/0211637 A1 | 9/2006 | Scaria et al. |
| 2006/0217332 A1 | 9/2006 | Vargeese et al. |
| 2006/0223770 A1 | 10/2006 | Fougerolles et al. |
| 2006/0292120 A1 | 12/2006 | Tolentino et al. |
| 2007/0003523 A1 | 1/2007 | Tolentino et al. |
| 2007/0037760 A1 | 2/2007 | Tolentino et al. |
| 2007/0037761 A1 | 2/2007 | Tolentino et al. |
| 2007/0037762 A1 | 2/2007 | Tolentino et al. |
| 2007/0149471 A1 | 6/2007 | Reich et al. |
| 2008/0124301 A1 | 5/2008 | Schlingensiepen et al. |
| 2008/0153771 A1 | 6/2008 | Liu et al. |
| 2008/0171025 A1 | 7/2008 | Mixson |
| 2008/0188437 A1 | 8/2008 | Tolentino et al. |
| 2008/0220027 A1 | 9/2008 | Liu et al. |
| 2008/0241198 A1 | 10/2008 | Liu et al. |
| 2009/0104259 A1 | 4/2009 | Tolentino et al. |
| 2009/0149403 A1 * | 6/2009 | MacLachlan et al. ......... 514/44 |

FOREIGN PATENT DOCUMENTS

| | | |
|---|---|---|
| EP | 0854185 | 12/1995 |
| EP | 1426444 | 9/1997 |
| EP | 1417971 | 9/1999 |
| EP | 1033401 | 2/2000 |
| EP | 1262199 | 5/2001 |
| EP | 1293569 | 3/2003 |
| EP | 1498424 | 4/2004 |
| EP | 1607485 | 6/2004 |
| EP | 1548445 | 12/2004 |
| EP | 1714970 | 4/2005 |
| FR | 2835837 | 8/2003 |
| FR | 2835838 | 8/2003 |
| WO | WO 96/06641 | 3/1996 |
| WO | WO 99/63975 | 12/1999 |
| WO | WO 99/63982 | 12/1999 |
| WO | WO 00/53790 | 9/2000 |
| WO | WO 01/27292 | 4/2001 |
| WO | WO 01/58468 | 8/2001 |
| WO | WO 02/085308 | 10/2002 |
| WO | WO 02/085309 | 10/2002 |
| WO | WO 02/096927 | 12/2002 |
| WO | WO 03/040366 | 5/2003 |
| WO | WO 2004/009769 | 1/2004 |
| WO | WO 2004/045543 | 6/2004 |
| WO | WO 2004/091648 | 10/2004 |
| WO | WO 2004/111237 | 12/2004 |
| WO | WO 2005/019453 | 3/2005 |
| WO | WO 2005/028649 | 3/2005 |
| WO | WO 2005/054270 | 6/2005 |
| WO | WO 2005/059133 | 6/2005 |
| WO | WO 2005/062957 | 7/2005 |
| WO | WO 2005/076998 | 8/2005 |
| WO | WO 2005/076999 | 8/2005 |
| WO | WO 2005/086891 | 9/2005 |
| WO | WO 2005/089224 | 9/2005 |
| WO | WO 2005/115358 | 12/2005 |
| WO | WO 2006/084272 | 8/2006 |
| WO | WO 2006/086639 | 8/2006 |
| WO | WO 2006/110813 | 9/2006 |
| WO | WO 2006/117400 | 11/2006 |
| WO | WO 2009/002440 | 12/2008 |

* cited by examiner

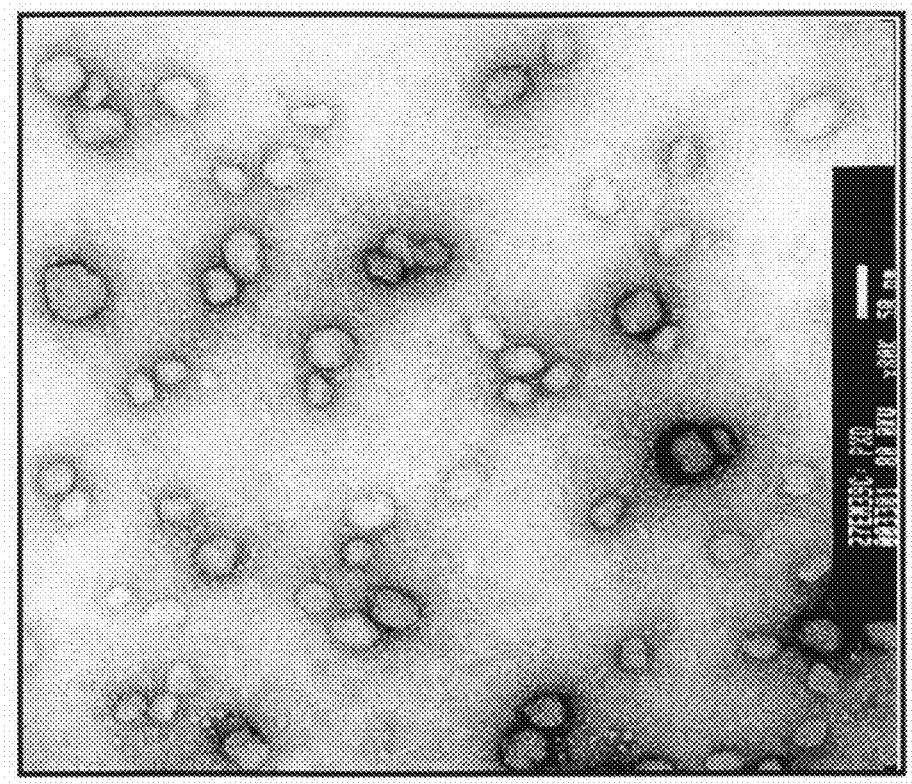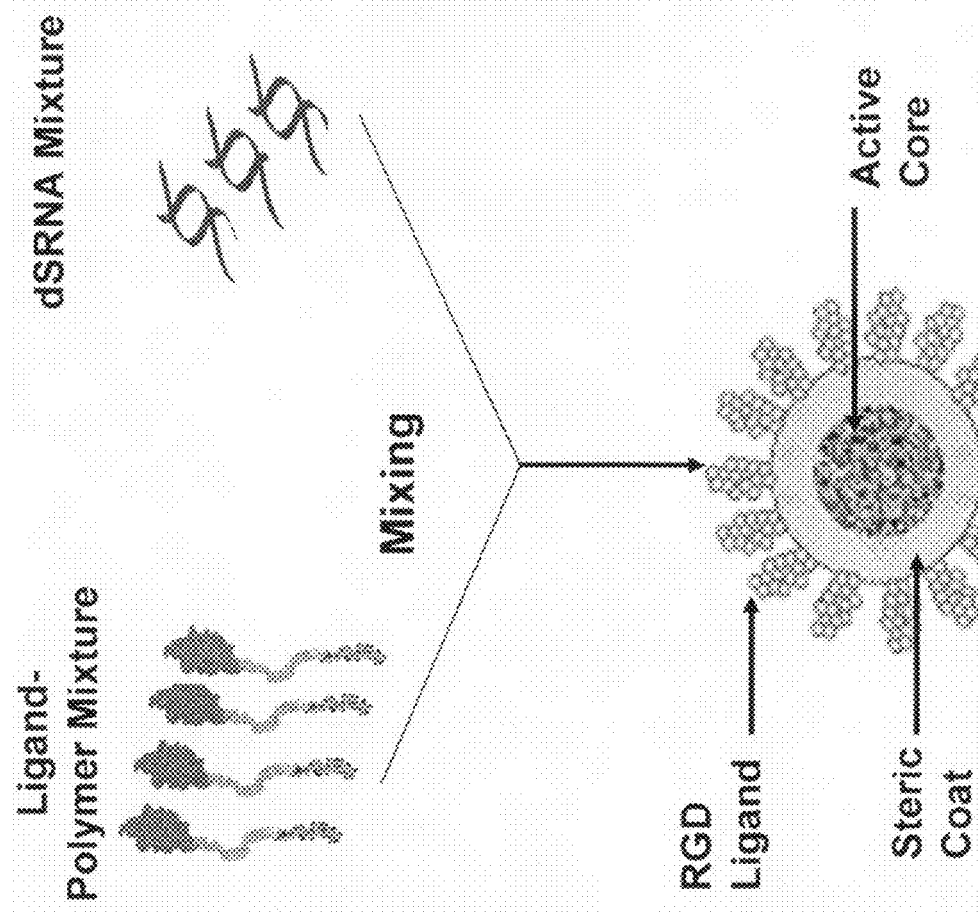
FIGURE 19

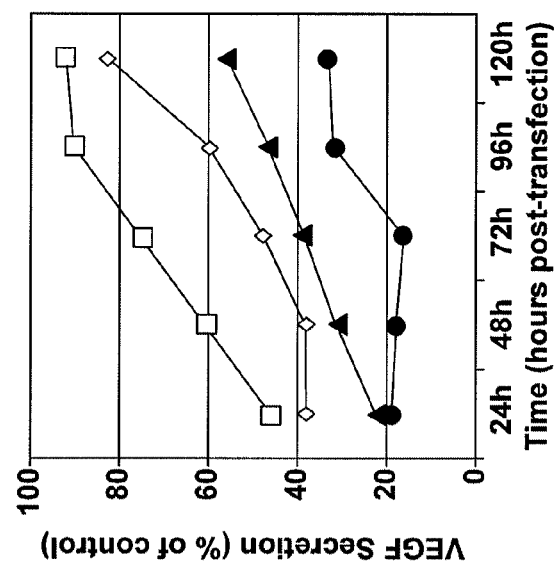
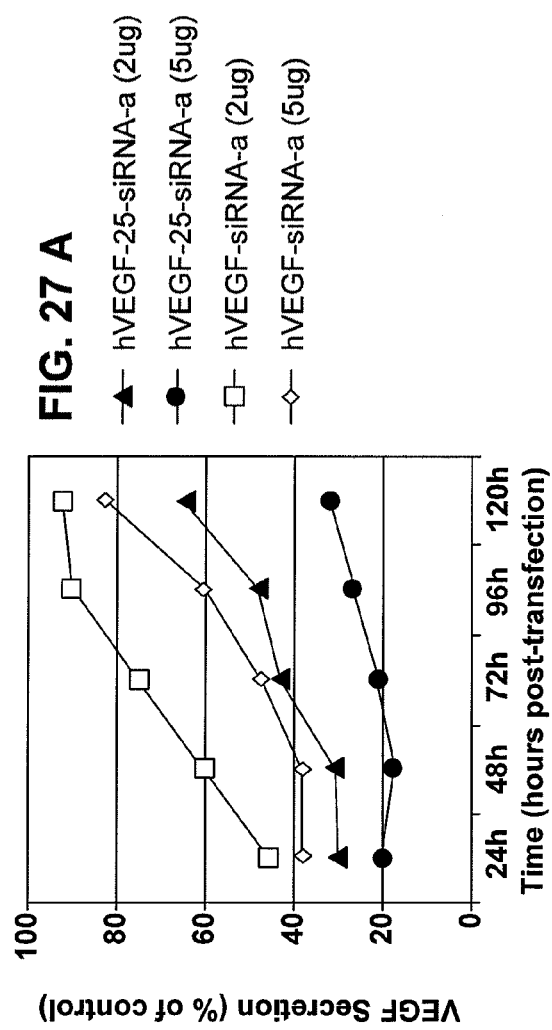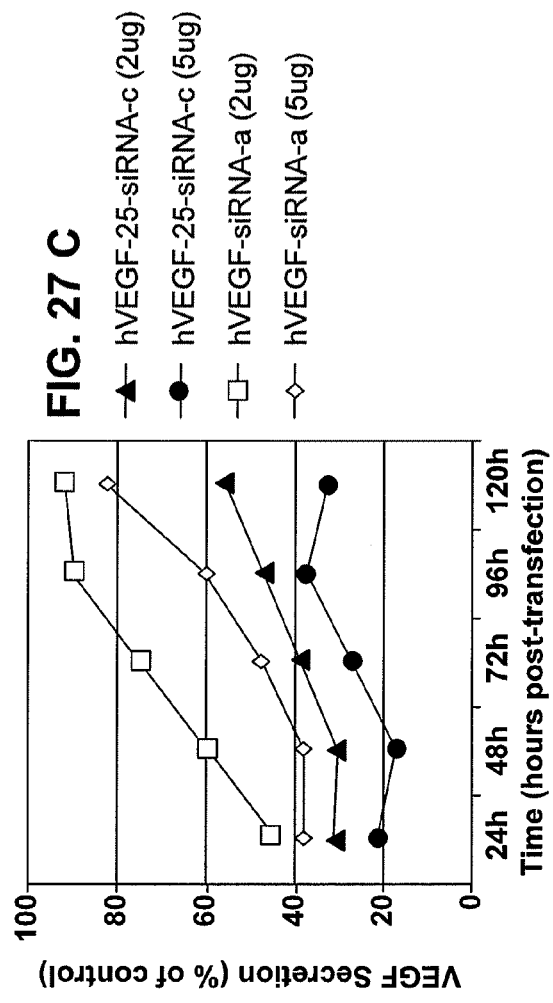

```
                     SEQUENCE LISTING

<160> NUMBER OF SEQ ID NOS: 322

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ccugaugaga ucgaguacau cuuca                                          25

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ugaagaugua cucgaucuca ucagg                                          25

<210> SEQ ID NO 3
<211> LENGTH: 25
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 3
gagagaugag cuuccuacag cacaa                                            25

<210> SEQ ID NO 4
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uugugcugua ggaagcucau cucuc                                            25

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cacaacaaau gugaaugcag accaa                                            25

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uuggucugca uucacauuug uugug                                            25

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
ucgagacccu gguggacaut t                                                21

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gccaacauau ucuacagugu ucuua                                            25

<210> SEQ ID NO 9
<211> LENGTH: 25
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 9
uaagaacacu guagaauaug uuggc                                              25

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cccucgccgg aaguuguaug guuaa                                              25

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uuaaccauac aacuuccggc gaggg                                              25

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
ggagaggacc ugaaacugut t                                                  21

<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ccucuucugu aagacacuca caauu                                              25

<210> SEQ ID NO 14
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
aauugugagu gucuuacaga agagg                                              25

<210> SEQ ID NO 15
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cccuugaguc caaucacaca auuaa                                                 25

<210> SEQ ID NO 16
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uuaauugugu gauuggacuc aaggg                                                 25

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ccaagugauu gaagcagaug ccuuu                                                 25

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaggcaucu gcuucaauca cuugg                                                 25

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
caguaagcga aagagccggt t                                                     21

<210> SEQ ID NO 20
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ccucaagagc aaacgugacu uauuu                                                 25
```

```
<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aaauaaguca cguuugcucu ugagg                                              25

<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
caagauccgc agacguguaa auguu                                              25

<210> SEQ ID NO 23
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aacauuuaca cgucugcgga ucuug                                              25

<210> SEQ ID NO 24
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gcagcuugag uuaaacgaac guacu                                              25

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aguacguucg uuuaacucaa gcugc                                              25

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
cagcuugagu uaaacgaacg uacuu                                              25
```

```
<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aaguacguuc guuuaacuca agcug                                                25

<210> SEQ ID NO 28
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ccaugccaag uggucccagg cugca                                                25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgcagcctgg gaccacttgg catgg                                                25

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cacauaggag agaugagcuu ccuca                                                25

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugaggaagcu caucucuccu augug                                                25

<210> SEQ ID NO 32
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ccuacggacc guuaagcggg ccaau                                                25

<210> SEQ ID NO 33
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
auuggcccgc uuaacggucc guagg                                           25

<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cucaugucug uucucaagau ccuca                                           25

<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ugaggaucuu gagaacagac augag                                           25

<210> SEQ ID NO 36
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cucaugguga uuuggaauu cugca                                            25

<210> SEQ ID NO 37
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ugcagaauuc cacaaucacc augag                                           25

<210> SEQ ID NO 38
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gagcauggaa gaggauucug gacuc                                           25

<210> SEQ ID NO 39
<211> LENGTH: 25
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 39
gaguccagaa uccucuucca ugctc                                                25

<210> SEQ ID NO 40
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cagaacagua agcgaaagag ccggc                                                25

<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gccggcucuu ucgcuuacug uucug                                                25

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gacuuccuga ccuuggagca ucuca                                                25

<210> SEQ ID NO 43
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ugagaugcuc caaggucagg aaguc                                                25

<210> SEQ ID NO 44
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccugaccuug gagcaucuca ucugu                                                25
```

```
<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
acagaugaga ugcuccaagg ucagg                                          25

<210> SEQ ID NO 46
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gcuaagggca uggaguucuu ggcau                                          25

<210> SEQ ID NO 47
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
augccaagaa cuccaugccc uuagc                                          25

<210> SEQ ID NO 48
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cacgcuguuu auugaaagag ucaca                                          25

<210> SEQ ID NO 49
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ugugacucuu ucaauaaaca gcgug                                          25

<210> SEQ ID NO 50
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
cgcuguuuau ugaaagaguc acaga                                          25

<210> SEQ ID NO 51
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ucugugacuc uuucaauaaa cagcg                                          25

<210> SEQ ID NO 52
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
caaggagggc cucugauggu gaugu                                          25

<210> SEQ ID NO 53
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
acaucaccau cagaggcccu ccuug                                          25

<210> SEQ ID NO 54
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ccaacuaccu caagagcaaa cguga                                          25

<210> SEQ ID NO 55
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ucacguuugc ucuugaggua guugg                                          25

<210> SEQ ID NO 56
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
cuaccucaag agcaaacgug acuua                                          25

<210> SEQ ID NO 57
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uaagucacgu uugcucuuga gguag                                      25

<210> SEQ ID NO 58
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ccagaaagug cauucaucgg gaccu                                      25

<210> SEQ ID NO 59
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
aggucccgau gaaugcacuu ucugg                                      25

<210> SEQ ID NO 60
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
cauucaucgg gaccuggcag cgaga                                      25

<210> SEQ ID NO 61
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ucucgcugcc aggucccgau gaaug                                      25

<210> SEQ ID NO 62
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
caucgggacc uggcagcgag aaaca                                      25

<210> SEQ ID NO 63
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 63
uguuucucgc ugccaggucc cgaug                                               25

<210> SEQ ID NO 64
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
gagccuggaa agaaucaaaa ccuuu                                               25

<210> SEQ ID NO 65
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
aaagguuuug auucuuucca ggcuc                                               25

<210> SEQ ID NO 66
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gccuggaaag aaucaaaacc uuuga                                               25

<210> SEQ ID NO 67
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ucaaagguuu ugauucuuuc caggc                                               25

<210> SEQ ID NO 68
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gccuggaaag aaucaaaacc uuuga                                               25

<210> SEQ ID NO 69
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 69
ucaaagguuu ugauucuuuc caggc                                         25

<210> SEQ ID NO 70
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cugaacugag uuuaaaaggc accca                                         25

<210> SEQ ID NO 71
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ugggugccuu uuaaacugag uucag                                         25

<210> SEQ ID NO 72
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gaacugaguu uaaaaggcac ccagc                                         25

<210> SEQ ID NO 73
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gcugggugcc uuuuaaacuc aguug                                         25

<210> SEQ ID NO 74
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
gaagauaaug acucaccugg ggcca                                         25

<210> SEQ ID NO 75
<211> LENGTH: 25
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 75
uggccccagg ugagucauua ucuuc                                         25

<210> SEQ ID NO 76
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
gauaaugacu caccuggggc cacau                                         25

<210> SEQ ID NO 77
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
auguggcccc aggugaguca uuauc                                         25

<210> SEQ ID NO 78
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
cucaccuggg gccacauuug aacau                                         25

<210> SEQ ID NO 79
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
auguucaaau guggccccag gugag                                         25

<210> SEQ ID NO 80
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cuugcuggga gccugcacca aguca                                         25

<210> SEQ ID NO 81
<211> LENGTH: 25
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 81
ugacuuggug caggcucccca gcaag                                        25

<210> SEQ ID NO 82
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
gauucuacuu ucuacaauaa gauca                                         25

<210> SEQ ID NO 83
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ugaucuuauu guagaaagua gaauc                                         25

<210> SEQ ID NO 84
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
cagagacuga gcgcugacag uggcu                                         25

<210> SEQ ID NO 85
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
agccacuguc ugcgcucagu cucug                                         25

<210> SEQ ID NO 86
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gaccugggca agaggaacag acaca                                         25

<210> SEQ ID NO 87
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 87
ugugucuguu ccucuugccc agguc                                        25

<210> SEQ ID NO 88
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ccaccuucau caagagagag gacga                                        25

<210> SEQ ID NO 89
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ucguccucuc ucuugaugaa ggugg                                        25

<210> SEQ ID NO 90
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uauggauuaa gccgguccca accugu                                       26

<210> SEQ ID NO 91
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
acagguuggg accggcuuaa uccaua                                       26

<210> SEQ ID NO 92
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
cugcagagac cucaaaaggu gucca                                        25

<210> SEQ ID NO 93
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 93
uggacaccuu uugaggucuc ugcag                                    25

<210> SEQ ID NO 94
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
cagagaccuc aaaaggugan cacgu                                    25

<210> SEQ ID NO 95
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
acguggacac cuuuugaggu cucug                                    25

<210> SEQ ID NO 96
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
guggugguga ucucagccau ccugg                                    25

<210> SEQ ID NO 97
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ccaggauggc ugagaucacc accac                                    25

<210> SEQ ID NO 98
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gguggugauc ucagccaucc uggcc                                    25

<210> SEQ ID NO 99
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
```
ggccaggaug gcugagauca ccacc					25

<210> SEQ ID NO 100
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ggcaagcugg ucaagaucug ugacu					25

<210> SEQ ID NO 101
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
agucacagau cuugaccagc uugcc					25

<210> SEQ ID NO 102
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gcaagcuggu caagaucugu gacuu					25

<210> SEQ ID NO 103
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
aagucacaga ucuugaccag cuugc					25

<210> SEQ ID NO 104
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
ggguggcacc ccuuacccag agcug					25

<210> SEQ ID NO 105
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
cagcucuggg uaaggggugc caccc                                              25

<210> SEQ ID NO 106
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gcaccccuua cccagagcug cccau                                              25

<210> SEQ ID NO 107
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
augggcagcu cuggguaagg ggugc                                              25

<210> SEQ ID NO 108
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
cuuacccaga gcugcccaug aacga                                              25

<210> SEQ ID NO 109
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
ucguucaugg gcagcucugg guaag                                              25

<210> SEQ ID NO 110
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
caugccuccg acgagaucua ugaga                                              25

<210> SEQ ID NO 111
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
ucucauagau cucgucggag gcaug                                              25

```
<210> SEQ ID NO 112
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
gccuccgacg agaucuauga gauca                                          25

<210> SEQ ID NO 113
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ugaucucaua gaucucgucg gaggc                                          25

<210> SEQ ID NO 114
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
ccgacgagau cuaugagauc augca                                          25

<210> SEQ ID NO 115
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
ugcaugaucu cauagaucuc gucgg                                          25

<210> SEQ ID NO 116
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gacgagaucu augagaucau gcaga                                          25

<210> SEQ ID NO 117
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
ucugcaugau cucauagauc ucguc                                          25
```

```
<210> SEQ ID NO 118
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
cucuggaucc cagaagguga gaaag                                               25

<210> SEQ ID NO 119
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cuuucucacc uucugggauc cagag                                               25

<210> SEQ ID NO 120
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
cagcauguca agaucacaga uuuug                                               25

<210> SEQ ID NO 121
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
caaaaucugu gaucuugaca ugcug                                               25

<210> SEQ ID NO 122
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gaucacagau uugggcugg ccaaa                                                25

<210> SEQ ID NO 123
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
uuuggccagc ccaaaaucug ugauc                                               25
```

```
<210> SEQ ID NO 124
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
cagauuuugg gcuggccaaa cugcu                                              25

<210> SEQ ID NO 125
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
agcaguuugg ccagcccaaa aucug                                              25

<210> SEQ ID NO 126
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
caaagugccu aucaagugga uggca                                              25

<210> SEQ ID NO 127
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ugccauccac uugauaggca cuuug                                              25

<210> SEQ ID NO 128
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ccaucgaugu cuacaugauc auggu                                              25

<210> SEQ ID NO 129
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
accaugauca uguagacauc gaugg                                              25

<210> SEQ ID NO 130
```

```
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
cgaugucuac augaucaugg ucaagu                                          26

<210> SEQ ID NO 131
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
acuugaccau gaucauguag acaucg                                          26

<210> SEQ ID NO 132
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
cuacaugauc auggucaagu gcugg                                           25

<210> SEQ ID NO 133
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ccagcacuug accaugauca uguag                                           25

<210> SEQ ID NO 134
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
caugaucaug gucaagugcu ggauga                                          26

<210> SEQ ID NO 135
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ucauccagca cuugaccaug aucaug                                          26

<210> SEQ ID NO 136
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ggaugaaaga augcauuugc caagu                                               25

<210> SEQ ID NO 137
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
acuuggcaaa ugcauucuuu caucc                                               25

<210> SEQ ID NO 138
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
gacaacccug acuaccagca ggacu                                               25

<210> SEQ ID NO 139
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
aguccugcug guagucaggg uuguc                                               25

<210> SEQ ID NO 140
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ccuucuuaaa gaccauccag gaggu                                               25

<210> SEQ ID NO 141
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
accuccugga uggucuuuaa gaagg                                               25

<210> SEQ ID NO 142
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 142
caagauccgc agacguguaa auguu                                              25

<210> SEQ ID NO 143
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
aacauuuaca cgucugcgga ucuug                                              25

<210> SEQ ID NO 144
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
caaggagggc cucugauggu gaugu                                              25

<210> SEQ ID NO 145
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
acaucaccau cagaggcccu ccuug                                              25

<210> SEQ ID NO 146
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
ccuacggacc guuaagcggg ccaau                                              25

<210> SEQ ID NO 147
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
auuggcccgc uuaacggucc guagg                                              25

<210> SEQ ID NO 148
<211> LENGTH: 25
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 148
caagauccgc agacguguaa auguu                                              25

<210> SEQ ID NO 149
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
aacauuuaca cgucugcgga ucuug                                              25

<210> SEQ ID NO 150
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ccagaaagug gauucaucgg gaccu                                              25

<210> SEQ ID NO 151
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
aggucccgau gaaugcacuu ucugg                                              25

<210> SEQ ID NO 152
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
cucaugucug uucucaagau ccuca                                              25

<210> SEQ ID NO 153
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
ugaggaucuu gagaacagac augag                                              25

<210> SEQ ID NO 154
<211> LENGTH: 25
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 154
gcagcuugag uuaaacgaac guacu                                              25

<210> SEQ ID NO 155
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
aguacguucg uuuaacucaa gcugc                                              25

<210> SEQ ID NO 156
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ccagaaagug cauucaucgg gaccu                                              25

<210> SEQ ID NO 157
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aggucccgau gaaugcacuu ucugg                                              25

<210> SEQ ID NO 158
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
cucaugucug uucucaagau ccuca                                              25

<210> SEQ ID NO 159
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ugaggaucuu gagaacagac augag                                              25

<210> SEQ ID NO 160
<211> LENGTH: 25
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 160
caagauccgc agacguguaa auguu                    25

<210> SEQ ID NO 161
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
aacauuuaca cgucugcgga ucuug                    25

<210> SEQ ID NO 162
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ccuacggacc guuaagcggg ccaau                    25

<210> SEQ ID NO 163
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
auuggcccgc uuaacggucc guagg                    25

<210> SEQ ID NO 164
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
cucuggaucc cagaagguga gaaag                    25

<210> SEQ ID NO 165
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
cuuucucacc uucuggdauc cagag                    25

<210> SEQ ID NO 166
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 166
caagauccgc agacguguaa auguu                                              25

<210> SEQ ID NO 167
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
aacauuuaca cgucugcgga ucuug                                              25

<210> SEQ ID NO 168
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
cucaugucug uucucaagau ccuca                                              25

<210> SEQ ID NO 169
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
ugaggaucuu gagaacagac augag                                              25

<210> SEQ ID NO 170
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
caaagugccu aucaagugga uggca                                              25

<210> SEQ ID NO 171
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ugccauccac uugauaggca cuuug                                              25

<210> SEQ ID NO 172
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 172
gcagcuugag uuaaacgaac guacu                                           25

<210> SEQ ID NO 173
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
aguacguucg uuuaacucaa gcugc                                           25

<210> SEQ ID NO 174
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
cucaugucug uucucaagau ccuca                                           25

<210> SEQ ID NO 175
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
ugaggaucuu gagaacagac augag                                           25

<210> SEQ ID NO 176
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
caugaucaug gucaagugcu ggauga                                          26

<210> SEQ ID NO 177
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
ucauccagca cuugaccaug aucaug                                          26

<210> SEQ ID NO 178
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
```

```
ccuacggacc guuaagcggg ccaau                                         25

<210> SEQ ID NO 179
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
auuggcccgc uuaacgaucc guagg                                         25

<210> SEQ ID NO 180
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
gaagauaaug acucaccugg ggcca                                         25

<210> SEQ ID NO 181
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uggccccagg ugagucauua ucuuc                                         25

<210> SEQ ID NO 182
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
cucuggaucc cagaagguga gaaag                                         25

<210> SEQ ID NO 183
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
cuuucucacc uucugggauc cagag                                         25

<210> SEQ ID NO 184
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
```

-continued ccagaaagug cauucaucgg gaccu          25

<210> SEQ ID NO 185
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aggucccgau gaaugcacuu ucugg          25

<210> SEQ ID NO 186
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
ccuacggacc guuaagcggg ccaau          25

<210> SEQ ID NO 187
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
auuggcccgc uuaacgglucc guagg          25

<210> SEQ ID NO 188
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
gauaaugacu caccuggggc cacau          25

<210> SEQ ID NO 189
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
auguggcccc aggugaguca uuauc          25

<210> SEQ ID NO 190
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
cucuggaucc cagaagguga gaaag          25

<210> SEQ ID NO 191
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
cuuucucacc uucugggauc cagag                                          25

<210> SEQ ID NO 192
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
ccuacggacc guuaagcggg ccaau                                          25

<210> SEQ ID NO 193
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
auuggcccgc uuaacggucc guagg                                          25

<210> SEQ ID NO 194
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
gauaaugacu caccuggggc cacau                                          25

<210> SEQ ID NO 195
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
auguggcccc aggugaguca uuauc                                          25

<210> SEQ ID NO 196
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
ccuucuuaaa gaccauccag gaggu                                          25

```
<210> SEQ ID NO 197
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
accuccugga uggucuuuaa gaagg                                               25

<210> SEQ ID NO 198
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
ccuacggacc guuaagcggg ccaau                                               25

<210> SEQ ID NO 199
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
auuggcccgc uuaacggucc guagg                                               25

<210> SEQ ID NO 200
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
ggcaagcugg ucaagaucug ugacu                                               25

<210> SEQ ID NO 201
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
agucacagau cuugaccagc uugcc                                               25

<210> SEQ ID NO 202
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
cucuggaucc cagaagguga gaaag                                               25
```

<210> SEQ ID NO 203
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
cuuucucacc uucugggauc cagag                                          25

<210> SEQ ID NO 204
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
ccuacggacc guuaagcggg ccaau                                          25

<210> SEQ ID NO 205
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
auuggcccgc uuaacggucc guagg                                          25

<210> SEQ ID NO 206
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
caugccuccg acgagaucua ugaga                                          25

<210> SEQ ID NO 207
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
ucucauagau cucgucggag gcaug                                          25

<210> SEQ ID NO 208
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
cucuggaucc cagaagguga gaaag                                          25

<210> SEQ ID NO 209

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
cuuucucacc uucugggauc cagag                                          25

<210> SEQ ID NO 210
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
ccuacggacc guuaagcggg ccaau                                          25

<210> SEQ ID NO 211
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
auuggcccgc uuaacggucc guagg                                          25

<210> SEQ ID NO 212
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
ggcaagcugg ucaagaucug ugacu                                          25

<210> SEQ ID NO 213
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
agucacagau cuugaccagc uugcc                                          25

<210> SEQ ID NO 214
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
ccuucuuaaa gaccauccag gaggu                                          25

<210> SEQ ID NO 215
<211> LENGTH: 25
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
accuccugga uggucuuuaa gaagg                                          25

<210> SEQ ID NO 216
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
ccuacggacc guuaagcggg ccaau                                          25

<210> SEQ ID NO 217
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
auuggcccgc uuaacggucc guagg                                          25

<210> SEQ ID NO 218
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
gauaaugacu caccuggggc cacau                                          25

<210> SEQ ID NO 219
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219 auuggcccc aggugaguca uuauc                                           25

<210> SEQ ID NO 220
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
ggcaagcugg ucaagaucug ugacu                                          25

<210> SEQ ID NO 221
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 221
agucacagau cuugaccagc uugcc                                           25

<210> SEQ ID NO 222
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
cucuggaucc cagaagguga gaaag                                           25

<210> SEQ ID NO 223
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
cuuucucacc uucugggauc cagag                                           25

<210> SEQ ID NO 224
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
ccagaaagug cauucaucgg gaccu                                           25

<210> SEQ ID NO 225
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
aggucccgau gaaugcacuu ucugg                                           25

<210> SEQ ID NO 226
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ccuacggacc guuaagcggg ccaau                                           25

<210> SEQ ID NO 227
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 227
auuggcccgc uuaacggucc guagg                                              25

<210> SEQ ID NO 228
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
caugccuccg acgagaucua ugaga                                              25

<210> SEQ ID NO 229
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
ucucauagau cucgucggag gcaug                                              25

<210> SEQ ID NO 230
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
cucuggaucc cagaagguga gaaag                                              25

<210> SEQ ID NO 231
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
cuuucucacc uucugggauc cagag                                              25

<210> SEQ ID NO 232
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
gcagcuugag uuaaacgaac guacu                                              25

<210> SEQ ID NO 233
<211> LENGTH: 25
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 233
aguacguucg uuuaacucaa gcugc                                               25

<210> SEQ ID NO 234
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
ccagaaagug cauucaucgg gaccu                                               25

<210> SEQ ID NO 235
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
aggucccgau gaaugcacuu ucugg                                               25

<210> SEQ ID NO 236
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
ccuacggacc guuaagcggg ccaau                                               25

<210> SEQ ID NO 237
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
auuggcccgc uuaacggucc guagg                                               25

<210> SEQ ID NO 238
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
gauaaugacu caccuggggc cacau                                               25

<210> SEQ ID NO 239
<211> LENGTH: 25
<212> TYPE: RNA
<213> ORGANISM: Artificial Sequence
<220> FEATURE:
<223> OTHER INFORMATION: Description of Artificial Sequence: Synthetic

```
                                  oligonucleotide

<400> SEQUENCE: 239
auguggcccc aggugaguca uuauc                                                 25

<210> SEQ ID NO 240
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
ggcaagcugg ucaagaucug ugacu                                                 25

<210> SEQ ID NO 241
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
agucacagau cuugaccagc uugcc                                                 25

<210> SEQ ID NO 242
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
ccuucuuaaa gaccauccag gaggu                                                 25

<210> SEQ ID NO 243
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
accuccugga uggucuuuaa gaagg                                                 25

<210> SEQ ID NO 244
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
gcagcuugag uuaaacgaac guacu                                                 25

<210> SEQ ID NO 245
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 245
aguacguucg uuuaacucaa gcugc                                            25

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ala Cys Arg Gly Asp Met Phe Gly Cys Ala
1               5                   10

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
aagctcagca cacagaaaga c                                                21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
aatgcggcgg tggtgacagt a                                                21

<210> SEQ ID NO 249
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
ggaaccgcug gagagcaacu gcaua                                            25

<210> SEQ ID NO 250
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
ccuuggcgac cucucguuga cguau                                            25

<210> SEQ ID NO 251
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 251
ucgagacccu gguggacaut t                                                   21

<210> SEQ ID NO 252
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 252
auguccacca gggucucgat t                                                   21

<210> SEQ ID NO 253
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 253
gcugacccug aaguucauct t                                                   21

<210> SEQ ID NO 254
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 254
gaugaacuuc agggucagct t                                                   21

<210> SEQ ID NO 255
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
ccaagugauu gaagcagaug ccuuu                                               25

<210> SEQ ID NO 256
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
```
tcaacgttga                                                          10

<210> SEQ ID NO 257
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
gctagacgtt agcgt                                                    15

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
aagccgtcct gtgtgccgct g                                             21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
aacgatgaag ccctggagtg c                                             21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
aagttaaaag tgcctgaact g                                             21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
aagcaggcca gactctcttt c                                             21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
aagctcagca cacagaaaga c							21

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
atgcggcggt ggtgacagta							20

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
aacagttgcg cagcctgaat g							21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
aacttaatcg ccttgcagca c							21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
aagctatgaa acgatatggg c							21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
aaccgctgga gagcaactgc a							21

<210> SEQ ID NO 268
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gatgtctacc agcgaagcta ctgccgtccg						30

<210> SEQ ID NO 269
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
gaacatcgat gacaagctta ggtatcgata caagctgcct cgccttg            47

<210> SEQ ID NO 270
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
gtcagctgct gggacaccgc ggtcttgcct                               30

<210> SEQ ID NO 271
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gaacatcgat gacaagctta ggtatcgata tagattgaag attccgc            47

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
tggctggtca aacagctcat c                                        21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
ctcatccaag ggcaattcat c                                        21

<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
cattgtgatg gactccggag acgg                                     24

```
<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
catctcctgc tgaagtctag agc                                              23

<210> SEQ ID NO 276
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
ccugaugaga ucgaguacau cuuca                                            25

<210> SEQ ID NO 277
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
gaguccaaca ucaccaugca gauua                                            25

<210> SEQ ID NO 278
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
aguccaacau caccaugcag auuau                                            25

<210> SEQ ID NO 279
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
ccaacaucac caugcagauu augcg                                            25

<210> SEQ ID NO 280
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
caccaugcag auuaugcgga ucaaa                                            25
```

```
<210> SEQ ID NO 281
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
gcacauagga gagaugagcu uccua                                               25

<210> SEQ ID NO 282
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
gagagaugag cuuccuacag cacaa                                               25

<210> SEQ ID NO 283
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
caaaggacuu uauacuuguc gugua                                               25

<210> SEQ ID NO 284
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
cccucgccgg aaguuguaug guuaa                                               25

<210> SEQ ID NO 285
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
caucacucag cgcauggcaa uaaua                                               25

<210> SEQ ID NO 286
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ccaccacuuu agacugucau gcuaa                                               25

<210> SEQ ID NO 287
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
cggacaaguc uaaucuggag cugau                                              25

<210> SEQ ID NO 288
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
ugacccacau uggccaccau cugaa                                              25

<210> SEQ ID NO 289
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gagggccucu gauggugauu guuga                                              25

<210> SEQ ID NO 290
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
cgagcuccgg cuuucaggaa gauaa                                              25

<210> SEQ ID NO 291
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
caaucaaugc cauacugaca ggaaa                                              25

<210> SEQ ID NO 292
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
gaaaguauuu cagcuccgaa guuua                                              25

<210> SEQ ID NO 293
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
ccucggucau uuaugucuau guuca                                              25

<210> SEQ ID NO 294
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
cagaucucca uuuauugcuu cuguu                                              25

<210> SEQ ID NO 295
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
gaccaacaug gagucgugua cauua                                              25

<210> SEQ ID NO 296
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
cccuugaguc caaucacaca auuaa                                              25

<210> SEQ ID NO 297
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ccauguucuu cuggcuacuu cuugu                                              25

<210> SEQ ID NO 298
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
ucauucauau uggucaccau cucaa                                              25

<210> SEQ ID NO 299
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 299
gaguucuugg caucgcgaaa gugua                                              25

<210> SEQ ID NO 300
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
cagcaggaau cagucaguau cugca                                              25

<210> SEQ ID NO 301
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
cagugguaug guucuugccu cagaa                                              25

<210> SEQ ID NO 302
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
ccacacugag cucuccuccu guuua                                              25

<210> SEQ ID NO 303
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
cagguauuuc uuacuggcuu ccaaa                                              25

<210> SEQ ID NO 304
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
gcuggugucu cagugaucau ggauu                                              25

<210> SEQ ID NO 305
<211> LENGTH: 25
<212> TYPE: RNA
<213> ORGANISM: Artificial Sequence
```

```
-continued

<220> FEATURE:
<223> OTHER INFORMATION: Description of Artificial Sequence: Synthetic
      oligonucleotide

<400> SEQUENCE: 305
cagaucucga ugguguggga gugaa                                              25

<210> SEQ ID NO 306
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
gauggagguu cguccacau uagua                                               25

<210> SEQ ID NO 307
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gccaagagau uauucuggac ugaua                                              25

<210> SEQ ID NO 308
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
cgaugccaag cagucuguga uugaa                                              25

<210> SEQ ID NO 309
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
uggcaggugg ugaaguugau cuaaa                                              25

<210> SEQ ID NO 310
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
gcgaagcuuu cauaugcccu ccuau                                              25

<210> SEQ ID NO 311
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 311
ucucuacgac uaaucaccua cucaa                                             25

<210> SEQ ID NO 312
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
cacugcaguc uuauuccaa guaag                                              25

<210> SEQ ID NO 313
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
cacaguggag cgaauuccuu uggaa                                             25

<210> SEQ ID NO 314
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314 cgcaaagug uguaacggaau aggua                                             25

<210> SEQ ID NO 315
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
cgcagcaugu caagaucaca gauuu                                             25

<210> SEQ ID NO 316
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
cagaaggagg caaagugccu aucaa                                             25

<210> SEQ ID NO 317
<211> LENGTH: 25
<212> TYPE: RNA
<213> ORGANISM: Artificial Sequence
<220> FEATURE:
<223> OTHER INFORMATION: Description of Artificial Sequence: Synthetic
```

```
                                -continued
        oligonucleotide

<400> SEQUENCE: 317
gccuaucaag uggauggcau uggaa                                              25

<210> SEQ ID NO 318
<211> LENGTH: 25
<212> TYPE: RNA
<213> ORGANISM: Artificial Sequence
<220> FEATURE:
<223> OTHER INFORMATION: Description of Artificial Sequence: Synthetic
        oligonucleotide

<400> SEQUENCE: 318
ccaaguccua cagacuccaa cuucu                                              25

<210> SEQ ID NO 319
<211> LENGTH: 25
<212> TYPE: RNA
<213> ORGANISM: Artificial Sequence
<220> FEATURE:
<223> OTHER INFORMATION: Description of Artificial Sequence: Synthetic
        oligonucleotide

<400> SEQUENCE: 319
ucucugagug caaccagcaa caauu                                              25

<210> SEQ ID NO 320
<211> LENGTH: 25
<212> TYPE: RNA
<213> ORGANISM: Artificial Sequence
<220> FEATURE:
<223> OTHER INFORMATION: Description of Artificial Sequence: Synthetic
        oligonucleotide

<400> SEQUENCE: 320
cagcuucuug cagcgauaca gcuca                                              25

<210> SEQ ID NO 321
<211> LENGTH: 25
<212> TYPE: RNA
<213> ORGANISM: Artificial Sequence
<220> FEATURE:
<223> OTHER INFORMATION: Description of Artificial Sequence: Synthetic
        oligonucleotide

<400> SEQUENCE: 321
gaagccaagc caaauggcau cuuua                                              25

<210> SEQ ID NO 322
<211> LENGTH: 25
<212> TYPE: RNA
<213> ORGANISM: Artificial Sequence
<220> FEATURE:
<223> OTHER INFORMATION: Description of Artificial Sequence: Synthetic
        oligonucleotide

<400> SEQUENCE: 322
uacagaaacg cauccagcaa gaaua                                              25
```

COMPOSITION AND METHODS OF RNAI THERAPEUTICS FOR TREATMENT OF CANCER AND OTHER NEOVASCULARIZATION DISEASES

This application claims priority from U.S. Provisional Patent Application No. 60/900,858, filed Feb. 9, 2007. This application is also a continuation-in-part of U.S. patent application Ser. No. 11/824,084, filed Jun. 29, 2007, which is a continuation application of International Patent Application No. PCT/US06/13645, filed Apr. 12, 2006, which designates the United States and which claims priority under 35 U.S.C. §119(e) from U.S. Provisional Patent Application No. 60/670,717, filed Apr. 12, 2005. The application also relates to the following applications: International Patent Application No. PCT/US05/03858, filed Feb. 7, 2005; International Patent Application No. PCT/US05/03857, filed Feb. 7, 2005; and International Patent Application No. PCT/US03/24587, filed Aug. 6, 2003. Each of the disclosures of PCT/US06/13645, PCT/US05/03858, PCT/US05/03857, PCT/US03/24587, U.S. Ser. No. 11/824,084, U.S. 60/900,858 and U.S. 60/670,717 is hereby incorporated by reference in its entirety.

The Sequence Listing associated with this application is provided in text format in lieu of a paper copy, and is hereby incorporated by reference into the specification. The name of the text file containing the Sequence Listing is sequence.txt. The text file is 76,968 bytes, was created on Feb. 23, 2009 and was submitted electronically via EFS-Web on Apr. 1, 2009 in this application.

FIELD OF THE INVENTION

The invention provides compositions and methods for treatments of diseases with unwanted neovascularization (NV), often an abnormal or excessive proliferation and growth of blood vessels. The development of NV itself often times has adverse consequences or it can be an early pathological step in disease. Despite introduction of new therapeutic antagonists of angiogenesis, including antagonists of the VEGF pathway, treatment options for controlling NV are inadequate and a large and growing unmet clinical need remains for effective treatments of NV, either to inhibit disease progression or to reverse unwanted angiogenesis. Since NV also can be a normal biological process, inhibition of unwanted NV is preferably accomplished with selectivity for a pathological tissue, which preferably requires selective delivery of therapeutic molecules to the pathological tissue.

The present invention overcomes this hurdle by providing treatments to control NV through selective inhibition of pro-angiogenic biochemical pathways, including inhibition of VEGF pathway gene expression and inhibition localized at pathological NV tissues. The present invention provides compositions and methods for using a tissue targeted nanoparticle composition comprising polymer conjugates and further comprising nucleic acid molecules that induce RNA interference (RNAi). The present invention provides compositions and methods for inhibition of individual genes or combinations of genes active in NV and more preferably in the VEGF pathway. The dsRNA nanoparticle compositions of the invention can be used alone or in combination with other therapeutic agents, including targeted therapeutics, including VEGF pathway antagonists, such as monoclonal antibodies and small molecule inhibitors, and targeted therapeutics inhibiting EGF and its receptor or PDGF and its receptors or MEK or Bcr-Abl, and immunotherapy and chemotherapy. The present invention also provides compositions and methods for the treatment of NV disease in a subject, including cancer, ocular disease, arthritis, and inflammatory diseases.

BACKGROUND OF THE INVENTION

Recent US FDA approved therapeutic agents, including Avastin, and Macugen, provide some benefit for NV diseases. Some of these agents act by binding to and inhibiting the action of Vascular Endothelial Growth Factor (VEGF), but these agents are not effective for many patients. Other agents being evaluated in clinical studies show signs that they may provide some benefit by binding to and inhibiting the action of the receptors for VEGF, or "down stream" proteins used by these receptors for signal transduction. The picture that has emerged is that means to control this VEGF "pathway" can provide a level of control of NV that provides benefit for some patients. In addition, studies of a series of small molecule kinase inhibitors found that a inhibitor called sunitinib that has activity against multiple kinase proteins, VEGF receptor, PDGF receptor, FLT3, and Kit, offers better clinical benefit for NV diseases. However, these benefits are still inadequate for most patients and better therapeutic means to control the VEGF pathway still are needed. The agents developed to date are mostly antagonists of VEGF or its receptors, VEGF R1 and VEGF R2. One problem that has emerged with use of antagonists appears to be a response by the pathological tissues to increase production of VEGF. Thus an attractive means to improve therapeutic control of NV is to inhibit production of the VEGF pathway proteins, i.e., down regulate their gene expression, and doing so by inducing RNA interference through in vivo delivery of small interfering dsRNA oligonucleotides (siRNA).

RNA interference (RNAi) is a post-transcriptional process where a double stranded RNA inhibits gene expression in a sequence specific fashion. The RNAi process occurs in at least two steps: During one step, a long dsRNA is cleaved by an endogenous ribonuclease into shorter, 21- or 23-nucleotide-long dsRNAs. In another second step, the smaller dsRNA mediates the degradation of an mRNA molecule with a matching sequence and as a result selectively down regulating expression of that gene. This RNAi effect can be achieved by introduction of either longer double-stranded RNA (dsRNA) or shorter small interfering RNA (siRNA) to the target sequence within cells. Recently, it was demonstrated that RNAi can also be achieved by introducing of plasmid that generate dsRNA complementary to target gene.

RNAi methods have been successfully used in gene function determination experiments in *Drosophila*[20, 22, 23, 25], *C. elegans*[14, 15, 16], and Zebrafish[20]. In those model organisms, it has been reported that both the chemically synthesized shorter siRNA or in vitro transcribed longer dsRNA can effectively inhibit target gene expression. Methods have been reported that successfully achieved RNAi effects in non human mammalian and human cell cultures[39-56]. However, RNAi effects have been difficult to observe in adult animal models[57]. This is for several reasons including: introduction of a long double-stranded RNA into mammalian cells can trigger an antiviral immune response including up-regulation of interferon, resulting in apoptosis and death of the cells that can be either detrimental or beneficial to the desired therapeutic effect: the efficiency of dsRNA entry into the target cell is low, especially in animals; short dsRNA molecules are rapidly excreted from the blood into the urine; and RNA molecules can be degraded by RNAse nuclease activity. Although RNAi has potential applications in both gene target validation and nucleic acid therapeutics, progress of the technology has been hindered due to the poor delivery of RNAi molecules into animal disease models.

It is apparent, therefore, that improved methods for delivering RNAi molecules in vivo are of great importance. It is also apparent that tissue targeted delivery of nucleic acid molecules inducing RNAi are of great importance. It is also apparent that methods for delivering nucleic acid molecules inducing RNAi selective for VEGF pathway genes will be of great benefit for the treatment of NV diseases. These needs are addressed by the compositions and methods of the invention.

SUMMARY OF THE INVENTION

It is therefore an object of the present invention to utilize RNAi to modulate angiogenesis process in order to reverse the disease process by down regulating gene expression involved in NV pathogenesis, more specifically genes in the VEGF pathway.

It is therefore an object of the invention to provide compositions and methods for inhibiting expression of one or more VEGF pathway genes in a mammal. It is a further object of the invention to provide compositions and methods for treating NV disease by inhibiting expression of one or more VEGF pathway genes alone or in combination with other agents including antagonists of the same VEGF pathway.

In achieving these objects there have been provided compositions and methods for down regulating endogenous VEGF pathway genes, comprising administering to a tissue of the mammal a composition comprising a double-stranded RNA molecule where the RNA molecule specifically reduces or inhibits expression of the endogenous VEGF pathway gene. This down regulation of an endogenous gene may be used for treating a disease that is caused or exacerbated by activity of the VEGF pathway. The disease may be in a human.

Additional embodiments of the invention have been provided as follows:

Paragraph 1. A nucleic acid molecule selected from the group consisting of:

```
(a)  5'-CCUGAUGAGAUCGAGUACAUCUUCA-3'
(b)  5'-GAGAGAUGAGCUUCCUACAGCACAA-3'
(c)  5'-CACAACAAAUGUGAAUGCAGACCAA-3'
(d)  5'-GAGUCCAACAUCACCAUGCAGAUUA-3'
(e)  5'-AGUCCAACAUCACCAUGCAGAUUAU-3'
(f)  5'-CCAACAUCACCAUGCAGAUUAUGCG-3'
(g)  5'-CACCAUGCAGAUUAUGCGGAUCAAA-3';
and
(h)  5'-GCACAUAGGAGAGAUGAGCUUCCUA-3'.
```

Paragraph 2. A 25 base pair nucleic acid molecule that is the complement of a nucleic acid molecule of paragraph 1.

Paragraph 3. A 25 base pair, blunt-ended double stranded nucleic acid selected from the group consisting of:

```
(a)     Sense strand:
        5'-CCUGAUGAGAUCGAGUACAUCUUCA-3'
        and antisense strand:
        5'-UGAAGAUGUACUCGAUCUCAUCAGG-3';

(b)     Sense strand:
        5'-GAGAGAUGAGCUUCCUACAGCACAA-3'
        and antisense strand:
        5'-UUGUGCUGUAGGAAGCUCAUCUCUC-3';
        and (c)     Sense strand:
        5'-CACAACAAAUGUGAAUGCAGACCAA-3'
        and antisense strand:
        5'-UUGGUCUGCAUUCACAUUUGUUGUG-3'.
```

Paragraph 4. A composition comprising the nucleic acid molecule of paragraph 2 or the double-stranded nucleic acid molecule of paragraph 3 and a pharmaceutically acceptable carrier.

Paragraph 5. The composition of paragraph 4, further comprising one or more additional nucleic acid molecules that induce RNA interference and decrease the expression of a gene of interest.

Paragraph 6. The composition of paragraph 5, wherein the one or more additional nucleic acid molecules decrease the expression of human VEGF.

Paragraph 7. The composition of paragraph 5, wherein the one or more additional nucleic acid molecules decrease the expression of a VEGF-pathway gene other than VEGF.

Paragraph 8. The composition of paragraph 5, wherein at least one of the one or more additional nucleic acid molecules decreases the expression of a gene that promotes angiogenesis.

Paragraph 9. The composition of paragraph 5, wherein at least one of the one or more additional nucleic acid molecules decreases the expression of a gene selected from the group consisting of; VEGFR1, VEGFR2, VEGFR3, PDGF, PDGFR-α, PDGFR-β, EGF, EGFR, RAF-a, RAF-c, AKT, RAS, NFkB, HIF, bFGF, bFGFR, Her-2, c-Met, c-Myc and HGF.

Paragraph 10. A composition comprising the nucleic acid molecule of paragraph 2 or the double stranded nucleic acid molecule of paragraph 3, and an additional nucleic acid molecule, wherein the additional nucleic acid molecule induces RNA interference and decreases the expression of human VEGFR1.

Paragraph 11. A composition comprising the nucleic acid molecule of paragraph 2 or the double stranded nucleic acid molecule of paragraph 3, and an additional nucleic acid molecule, wherein the additional nucleic acid molecule induces RNA interference and decreases the expression of human VEGFR2.

Paragraph 12. A composition comprising:
(a) the nucleic acid molecule of paragraph 2 or the double stranded nucleic acid molecule of paragraph 3,
(b) a nucleic acid molecule that induces RNA interference and decreases the expression of human VEGFR1; and
(c) a nucleic acid molecule that induces RNA interference and decreases the expression of human VEGFR2.

Paragraph 13. The composition of paragraph 4, wherein the carrier is a nucleic acid delivery vehicle.

Paragraph 14. The composition of paragraph 13, wherein the nucleic acid delivery vehicle is synthetic.

Paragraph 15. The composition of paragraph 14 wherein the synthetic nucleic acid delivery vehicle comprises a core region comprising a cationic polymer and the nucleic acid.

Paragraph 16. The composition of paragraph 15, wherein the cationic polymer is polyethyleneimine.

Paragraph 17. The composition of paragraph 15, wherein the cationic polymer is a histidine-lysine co-polymer.

Paragraph 18. The composition of paragraph 15, wherein the synthetic nucleic acid delivery vehicle further comprises a protective hydrophilic layer.

Paragraph 19. The composition of paragraph 18, wherein the protective hydrophilic layer comprises a component selected from the group consisting of: polyethylene glycol, a polyacetal and a polyoxazoline.

Paragraph 20. The composition of paragraph 15, wherein the synthetic nucleic acid vehicle further comprises a targeting moiety.

Paragraph 21. The composition of paragraph 18, wherein the synthetic nucleic acid vehicle further comprises a targeting moiety.

Paragraph 22. The composition of paragraph 20, wherein the targeting moiety binds a tumor specific molecule or an angiogenesis-specific molecule.

Paragraph 23. The composition of paragraph 20, wherein the targeting moiety binds endothelial cells.

Paragraph 24. The composition of paragraph 23, wherein the targeting moiety binds an integrin on vascular endothelial cells.

Paragraph 25. The composition of paragraph 24, wherein the targeting moiety is a peptide comprising the amino acid sequence RGD.

Paragraph 26. The composition of paragraph 25, wherein the peptide comprising RGD is a cyclic peptide.

Paragraph 27. The composition of paragraph 14, wherein the synthetic nucleic acid delivery vehicle comprises:
(a) a core region comprising PEI;
(b) a protective hydrophilic layer comprising PEG; and
(c) a cyclic RGD-containing peptide targeting moiety.

Paragraph 28. The composition of paragraph 4 comprising an additional therapeutic agent selected from the group consisting of: an anti-cancer agent, an anti-inflammatory agent and an anti-infective agent.

Paragraph 29. The composition of paragraph 4 comprising an anti-angiogenic agent.

Paragraph 30. The composition of paragraph 29, wherein the anti-angiogenic agent is an inhibitor selected from the group consisting of: an inhibitor of human VEGF, an inhibitor of human VEGFR1 and an inhibitor of human VEGFR2.

Paragraph 31. A method for reducing neovascularization in a subject in need thereof comprising the step of administering to the subject a composition selected from the group consisting of:
(a) the nucleic acid of paragraph 2; and
(b) the double stranded nucleic acid of paragraph 3.

Paragraph 32. A method for reducing neovascularization in a subject in need thereof comprising the step of administering to the subject the composition of paragraph 4.

Paragraph 33. A method for reducing neovascularization in a subject in need thereof comprising the step of administering to the subject the composition of paragraph 12.

Paragraph 34. A method of reducing tumor growth in a subject in need thereof, comprising the step of administering the nucleic acid of paragraph 3 or the double stranded nucleic acid of paragraph 41 to the subject.

Paragraph 35. A method for decreasing the VEGF protein level in a cell comprising introducing into the cell the nucleic acid molecule of paragraph 2 or the double-stranded nucleic acid of paragraph 3.

Paragraph 36. The nucleic acid molecule of paragraph 1, wherein said nucleic acid molecule is RNA.

Paragraph 37. The double-stranded nucleic acid molecule of paragraph 3, wherein said double-stranded nucleic acid molecule is RNA.

Paragraph 38. A nucleic acid molecule selected from the group consisting of:

```
(a)  5'-GCCAACAUAUUCUACAGUGUUCUUA-3';
(b)  5'-CCCUCGCCGGAAGUUGUAUGGUUAA-3';
(c)  5'-CCUCAAGAGCAAACGUGACUUAUUU-3';
(d)  5'-CAAAGGACUUUAUACUUGUCGUGUA-3';
(e)  5'-CAUCACUCAGCGCAUGGCAAUAAUA-3';
(f)  5'-CCACCACUUUAGACUGUCAUGCUAA-3';
(g)  5'-CGGACAAGUCUAAUCUGGAGCUGAU-3';
(h)  5'-UGACCCACAUUGGCCACCAUCUGAA-3';
(i)  5'-GAGGGCCUCUGAUGGUGAUUGUUGA-3';
(j)  5'-CGAGCUCCGGCUUUCAGGAAGAUAA-3';
(k)  5'-CAAUCAAUGCCAUACUGACAGGAAA-3';
    and
(l)  5'-GAAAGUAUUUCAGCUCCGAAGUUUA-3'.
```

Paragraph 39. A 25 base pair nucleic acid molecule that is the complement of a nucleic acid molecule of paragraph 39.

Paragraph 40. A 25 base pair, blunt-ended double stranded nucleic acid selected from the group consisting of:

```
(a)  Sense strand:
     5'-GCCAACAUAUUCUACAGUGUUCUUA-3'
     and antisense strand:
     5'-UAAGAACACUGUAGAAUAUGUUGGC-3';

(b)  Sense strand:
     5'-CCCUCGCCGGAAGUUGUAUGGUUAA-3'
     and antisense strand:
     5'-UUAACCAUACAACUUCCGGCGAGGG-3';
     and (c)  Sense strand:
     5'-CCUCAAGAGCAAACGUGACUUAUUU-3'
     and antisense strand:
     5'-AAAUAAGUCACGUUUGCUCUUGAGG-3'.
```

Paragraph 41. A composition comprising the nucleic acid molecule of paragraph 39 or the double-stranded nucleic acid molecule of paragraph 40 and a pharmaceutically acceptable carrier.

Paragraph 42. The composition of paragraph 41, further comprising one or more additional nucleic acid molecules that induce RNA interference and decrease the expression of a gene of interest.

Paragraph 43. The composition of paragraph 42, wherein the one or more additional nucleic acid molecules decrease the expression of human VEGFR1.

Paragraph 44. The composition of paragraph 42, wherein the one or more additional nucleic acid molecules decrease the expression of a VEGF-pathway gene other than VEGFR1.

Paragraph 45. The composition of paragraph 42, wherein at least one of the one or more additional nucleic acid molecules decreases the expression of a gene that promotes angiogenesis.

Paragraph 46. The composition of paragraph 42, wherein at least one of the one or more additional nucleic acid molecules decreases the expression of a gene selected from the group consisting of: VEGF, VEGFR2, VEGFR3, PDGF, PDGFR-α, PDGFR-β, EGF, EGFR, RAF-a, RAF-c, AKT, RAS, NFkB, HIF, bFGF, bFGFR, Her-2, c-Met, c-Myc and HGF.

Paragraph 47. A composition comprising the nucleic acid molecule of paragraph 39 or the double stranded nucleic acid molecule of paragraph 40, and an additional nucleic acid molecule, wherein the additional nucleic acid molecule induces RNA interference and decreases the expression of human VEGF.

Paragraph 48. A composition comprising the nucleic acid molecule of paragraph 39 or the double stranded nucleic acid molecule of paragraph 40, and an additional nucleic acid molecule, wherein the additional nucleic acid molecule induces RNA interference and decreases the expression of human VEGFR2.

Paragraph 49. A composition comprising:
(a) the nucleic acid molecule of paragraph 39 or the double stranded nucleic acid molecule of paragraph 40,
(b) a nucleic acid molecule that induces RNA interference and decreases the expression of human VEGF; and
(c) a nucleic acid molecule that induces RNA interference and decreases the expression of human VEGFR2.

Paragraph 50. The composition of paragraph 41, wherein the carrier is a nucleic acid delivery vehicle.

Paragraph 51. The composition of paragraph 50, wherein the nucleic acid delivery vehicle is synthetic.

Paragraph 52. The composition of paragraph 51, wherein the synthetic nucleic acid delivery vehicle comprises a core region comprising a cationic polymer and the nucleic acid.

Paragraph 53. The composition of paragraph 52, wherein the cationic polymer is polyethyleneimine.

Paragraph 54. The composition of paragraph 52, wherein the cationic polymer is a histidine-lysine co-polymer.

Paragraph 55. The composition of paragraph 52, wherein the synthetic nucleic acid delivery vehicle further comprises a protective hydrophilic layer.

Paragraph 56. The composition of paragraph 55, wherein the protective hydrophilic layer comprises a component selected from the group consisting of: polyethylene glycol, a polyacetal and a polyoxazoline.

Paragraph 57. The composition of paragraph 52, wherein the synthetic nucleic acid vehicle further comprises a targeting moiety.

Paragraph 58. The composition of paragraph 55, wherein the synthetic nucleic acid vehicle further comprises a targeting moiety.

Paragraph 59. The composition of paragraph 57, wherein the targeting moiety binds a tumor specific molecule or an angiogenesis-specific molecule.

Paragraph 60. The composition of paragraph 57, wherein the targeting moiety binds endothelial cells.

Paragraph 61. The composition of paragraph 60, wherein the targeting moiety binds an integrin on vascular endothelial cells.

Paragraph 62. The composition of paragraph 61, wherein the targeting moiety is a peptide comprising the amino acid sequence RGD.

Paragraph 63. The composition of paragraph 62, wherein the peptide comprising RGD is a cyclic peptide.

Paragraph 64. The composition of paragraph 51, wherein the synthetic nucleic acid delivery vehicle comprises:
(a) a core region comprising PEI;
(b) a protective hydrophilic layer comprising PEG; and
(c) a cyclic RGD-containing peptide targeting moiety.

Paragraph 65. The composition of paragraph 41 comprising an additional therapeutic agent selected from the group consisting of: an anti-cancer agent, an anti-inflammatory agent and an anti-infective agent.

Paragraph 66. The composition of paragraph 41 comprising an anti-angiogenic agent.

Paragraph 67. The composition of paragraph 66, wherein the anti-angiogenic agent is an inhibitor selected from the group consisting of: an inhibitor of human VEGF, an inhibitor of human VEGFR1 and an inhibitor of human VEGFR2.

Paragraph 68. A method for reducing neovascularization in a subject in need thereof comprising the step of administering to the subject a composition selected from the group consisting of:
(a) the nucleic acid of paragraph 39; and
(b) the double stranded nucleic acid of paragraph 40.

Paragraph 69. A method for reducing neovascularization in a subject in need thereof comprising the step of administering to the subject the composition of paragraph 41.

Paragraph 70. A method for reducing neovascularization in a subject in need thereof comprising the step of administering to the subject the composition of paragraph 49.

Paragraph 71. A method of reducing tumor growth in a subject in need thereof, comprising the step of administering the nucleic acid of paragraph 39 or the double stranded nucleic acid of paragraph 40 to the subject.

Paragraph 72. A method for decreasing the VEGFR1 protein level in a cell comprising introducing into the cell the nucleic acid molecule of paragraph 39 or the double-stranded nucleic acid of paragraph 40.

Paragraph 73. The nucleic acid molecule of paragraph 38, wherein said nucleic acid molecule is RNA.

Paragraph 74. The double-stranded nucleic acid molecule of paragraph 40, wherein said double-stranded nucleic acid molecule is RNA.

Paragraph 75. A nucleic acid molecule selected from the group consisting of:

(a) 5'-CCUCUUCUGUAAGACACUCACAAUU-3';

(b) 5'-CCCUUGAGUCCAAUCACACAAUUAA-3';

(c) 5'-CCAAGUGAUUGAAGCAGAUGCCUUU-3';

(d) 5'-CCUCGGUCAUUUAUGUCUAUGUUCA-3';

(e) 5'-CAGAUCUCCAUUUAUUGCUUCUGUU-3';

(f) 5'-GACCAACAUGGAGUCGUGUACAUUA-3';

(g) 5'-CCCUUGAGUCCAAUCACACAAUUAA-3';

(h) 5'-CCAUGUUCUUCUGGCUACUUCUUGU-3';

(i) 5'-UCAUUCAUAUUGGUCACCAUCUCAA-3';

(j) 5'-GAGUUCUUGGCAUCGCGAAAGUGUA-3';

-continued (k) 5'-CAGCAGGAAUCAGUCAGUAUCUGCA-3';

(l) 5'-CAGUGGUAUGGUUCUUGCCUCAGAA-3'; and (m) 5'-CCACACUGAGCUCUCCUCCUGUUUA-3'.

Paragraph 76. A 25 base pair nucleic acid molecule that is the complement of a nucleic acid molecule of paragraph 75.

Paragraph 77. A 25 base pair, blunt-ended double stranded nucleic acid selected from the group consisting of:

(a) Sense strand
5'-CCUCUUCUGUAAGACACUCACAAUU-3'
and antisense strand:
5'-AAUUGUGAGUGUCUUACAGAAGAGG-3';

(b) Sense strand:
5'-CCCUUGAGUCCAAUCACACAAUUAA-3'
and antisense strand:
5'-UUAAUUGUGUGAUUGGACUCAAGGG-3'

(c) Sense strand:
5'-CCAAGUGAUUGAAGCAGAUGCCUUU-3'
and antisense strand:
5'-AAAGGCAUCUGCUUCAAUCACUUGG-3'.

Paragraph 78. A composition comprising the nucleic acid molecule of paragraph 76 or the double-stranded nucleic acid molecule of paragraph 77 and a pharmaceutically acceptable carrier.

Paragraph 79. The composition of paragraph 78, further comprising one or more additional nucleic acid molecules that induce RNA interference and decrease the expression of a gene of interest.

Paragraph 80. The composition of paragraph 79, wherein the one or more additional nucleic acid molecules decrease the expression of human VEGFR2.

Paragraph 81. The composition of paragraph 79, wherein the one or more additional nucleic acid molecules decrease the expression of a VEGF-pathway gene other than VEGFR2.

Paragraph 82. The composition of paragraph 79, wherein at least one of the one or more additional nucleic acid molecules decreases the expression of a gene that promotes angiogenesis.

Paragraph 83. The composition of paragraph 79, wherein at least one of the one or more additional nucleic acid molecules decreases the expression of a gene selected from the group consisting of; VEGFR1, VEGF, VEGFR3, PDGF, PDGFR-α, PDGFR-β, EGF, EGFR, RAF-a, RAF-c, AKT, RAS, NFkB, HIF, bFGF, bFGFR, Her-2, c-Met, c-Myc and HGF.

Paragraph 84. A composition comprising the nucleic acid molecule of paragraph 76 or the double stranded nucleic acid molecule of paragraph 77, and an additional nucleic acid molecule, wherein the additional nucleic acid molecule induces RNA interference and decreases the expression of human VEGF.

Paragraph 85. A composition comprising the nucleic acid molecule of paragraph 76 or the double stranded nucleic acid molecule of paragraph 77, and an additional nucleic acid molecule, wherein the additional nucleic acid molecule induces RNA interference and decreases the expression of human VEGFR1.

Paragraph 86. A composition comprising:
(a) the nucleic acid molecule of paragraph 76 or the double stranded nucleic acid molecule of paragraph 77,
(b) a nucleic acid molecule that induces RNA interference and decreases the expression of human VEGFR1; and
(c) a nucleic acid molecule that induces RNA interference and decreases the expression of human VEGF.

Paragraph 87. The composition of paragraph 78, wherein the carrier is a nucleic acid delivery vehicle.

Paragraph 88. The composition of paragraph 87, wherein the nucleic acid delivery vehicle is synthetic.

Paragraph 89. The composition of paragraph 88 wherein the synthetic nucleic acid delivery vehicle comprises a core region comprising a cationic polymer and the nucleic acid.

Paragraph 90. The composition of paragraph 89, wherein the cationic polymer is polyethyleneimine.

Paragraph 91. The composition of paragraph 89, wherein the cationic polymer is a histidine-lysine co-polymer.

Paragraph 92. The composition of paragraph 89, wherein the synthetic nucleic acid delivery vehicle further comprises a protective hydrophilic layer.

Paragraph 93. The composition of paragraph 92, wherein the protective hydrophilic layer comprises a component selected from the group consisting of: polyethylene glycol, a polyacetal and a polyoxazoline.

Paragraph 94. The composition of paragraph 89, wherein the synthetic nucleic acid vehicle further comprises a targeting moiety.

Paragraph 95. The composition of paragraph 92, wherein the synthetic nucleic acid vehicle further comprises a targeting moiety.

Paragraph 96. The composition of paragraph 94, wherein the targeting moiety binds a tumor specific molecule or an angiogenesis-specific molecule.

Paragraph 97. The composition of paragraph 94, wherein the targeting moiety binds endothelial cells.

Paragraph 98. The composition of paragraph 97, wherein the targeting moiety binds an integrin on vascular endothelial cells.

Paragraph 99. The composition of paragraph 98, wherein the targeting moiety is a peptide comprising the amino acid sequence RGD.

Paragraph 100. The composition of paragraph 99, wherein the peptide comprising RGD is a cyclic peptide.

Paragraph 101. The composition of paragraph 88, wherein the synthetic nucleic acid delivery vehicle comprises:
(a) a core region comprising PEI;
(b) a protective hydrophilic layer comprising PEG; and
(c) a cyclic RGD-containing peptide targeting moiety.

Paragraph 102. The composition of paragraph 78 comprising an additional therapeutic agent selected from the group consisting of: an anti-cancer agent, an anti-inflammatory agent and an anti-infective agent.

Paragraph 103. The composition of paragraph 78 comprising an anti-angiogenic agent.

Paragraph 104. The composition of paragraph 103, wherein the anti-angiogenic agent is an inhibitor selected from the group consisting of: an inhibitor of human VEGF, an inhibitor of human VEGFR1 and an inhibitor of human VEGFR2.

Paragraph 105. A method for reducing neovascularization in a subject in need thereof comprising the step of administering to the subject a composition selected from the group consisting of:
(a) the nucleic acid of paragraph 76; and
(b) the double stranded nucleic acid of paragraph 77.

Paragraph 106. A method for reducing neovascularization in a subject in need thereof comprising the step of administering to the subject the composition of paragraph 78.

Paragraph 107. A method for reducing neovascularization in a subject in need thereof comprising the step of administering to the subject the composition of paragraph 86.

Paragraph 108. A method of reducing tumor growth in a subject in need thereof, comprising the step of administering the nucleic acid of paragraph 76 or the double stranded nucleic acid of paragraph 77 to the subject.

Paragraph 109. A method for decreasing the VEGFR2 protein level in a cell comprising introducing into the cell the nucleic acid molecule of paragraph 76 or the double-stranded nucleic acid of paragraph 77.

Paragraph 110. The nucleic acid molecule of paragraph 75, wherein said nucleic acid molecule is RNA.

Paragraph 111. The double-stranded nucleic acid molecule of paragraph 77, wherein said double-stranded nucleic acid molecule is RNA.

Paragraph 112. A composition selected from the group consisting of:

a composition comprising a siRNA identified by SEQ ID NO. 2, a siRNA identified by SEQ ID NO. 9 a siRNA identified by SEQ ID NO. 14 and a pharmaceutically acceptable carrier;

a composition comprising a siRNA identified by SEQ ID NO. 2, a siRNA identified by SEQ ID NO. 9, a siRNA identified by SEQ ID NO. 16 and a pharmaceutically acceptable carrier;

a composition comprising a siRNA identified by SEQ ID NO. 2, a siRNA identified by SEQ ID NO. 9, a siRNA identified by SEQ ID NO. 18 and a pharmaceutically acceptable carrier;

a composition comprising a siRNA identified by SEQ ID NO. 2, a siRNA identified by SEQ ID NO. 11, a siRNA identified by SEQ ID NO. 14 and a pharmaceutically acceptable carrier;

a composition comprising a siRNA identified by SEQ ID NO. 2, a siRNA identified by SEQ ID NO. 11, a siRNA identified by SEQ ID NO. 16 and a pharmaceutically acceptable carrier;

a composition comprising a siRNA identified by SEQ ID NO. 2, a siRNA identified by SEQ ID NO. 11, a siRNA identified by SEQ ID NO. 18 and a pharmaceutically acceptable carrier;

a composition comprising a siRNA identified by SEQ ID NO. 2, a siRNA with the sequence of SEQ ID NO. 21, a siRNA identified by SEQ ID NO. 14 and a pharmaceutically acceptable carrier;

a composition comprising a siRNA identified by SEQ ID NO. 2, a siRNA with the sequence of SEQ ID NO. 21, a siRNA identified by SEQ ID NO. 16 and a pharmaceutically acceptable carrier;

a composition comprising a siRNA identified by SEQ ID NO. 2, a siRNA with the sequence of SEQ ID NO. 21, a siRNA identified by SEQ ID NO. 18 and a pharmaceutically acceptable carrier;

a composition comprising a siRNA identified by SEQ ID NO. 4, a siRNA identified by SEQ ID NO. 9, a siRNA identified by SEQ ID NO. 14 and a pharmaceutically acceptable carrier;

a composition comprising a siRNA identified by SEQ ID NO. 4, a siRNA identified by SEQ ID NO. 9, a siRNA identified by SEQ ID NO. 16 and a pharmaceutically acceptable carrier;

a composition comprising a siRNA identified by SEQ ID NO. 4, a siRNA identified by SEQ ID NO. 9, a siRNA identified by SEQ ID NO. 18 and a pharmaceutically acceptable carrier;

a composition comprising a siRNA identified by SEQ ID NO. 4, a siRNA identified by SEQ ID NO. 11, a siRNA identified by SEQ ID NO. 14 and a pharmaceutically acceptable carrier;

a composition comprising a siRNA identified by SEQ ID NO. 4, a siRNA identified by SEQ ID NO. 11, a siRNA identified by SEQ ID NO. 16 and a pharmaceutically acceptable carrier;

a composition comprising a siRNA identified by SEQ ID NO. 4, a siRNA identified by SEQ ID NO. 11, a siRNA identified by SEQ ID NO. 18 and a pharmaceutically acceptable carrier;

a composition comprising a siRNA identified by SEQ ID NO. 4, a siRNA with the sequence of SEQ ID NO. 21, a siRNA identified by SEQ ID NO. 14 and a pharmaceutically acceptable carrier;

a composition comprising a siRNA identified by SEQ ID NO. 4, a siRNA with the sequence of SEQ ID NO. 21, a siRNA identified by SEQ ID NO. 16 and a pharmaceutically acceptable carrier;

a composition comprising a siRNA identified by SEQ ID NO. 4, a siRNA with the sequence of SEQ ID NO. 21, a siRNA identified by SEQ ID NO. 18 and a pharmaceutically acceptable carrier;

a composition comprising a siRNA identified by SEQ ID NO. 6, a siRNA identified by SEQ ID NO. 9, a siRNA identified by SEQ ID NO. 14 and a pharmaceutically acceptable carrier;

a composition comprising a siRNA identified by SEQ ID NO. 6, a siRNA identified by SEQ ID NO. 9, a siRNA identified by SEQ ID NO. 16 and a pharmaceutically acceptable carrier;

a composition comprising a siRNA identified by SEQ ID NO. 6, a siRNA identified by SEQ ID NO. 9, a siRNA identified by SEQ ID NO. 18 and a pharmaceutically acceptable carrier;

a composition comprising a siRNA identified by SEQ ID NO. 6, a siRNA identified by SEQ ID NO. 11, a siRNA identified by SEQ ID NO. 14 and a pharmaceutically acceptable carrier;

a composition comprising a siRNA identified by SEQ ID NO. 6, a siRNA identified by SEQ ID NO. 11, a siRNA identified by SEQ ID NO. 16 and a pharmaceutically acceptable carrier;

a composition comprising a siRNA identified by SEQ ID NO. 6, a siRNA identified by SEQ ID NO. 11, a siRNA identified by SEQ ID NO. 18 and a pharmaceutically acceptable carrier;

a composition comprising a siRNA identified by SEQ ID NO. 6, a siRNA with the sequence of SEQ ID NO. 21, a siRNA identified by SEQ ID NO. 14 and a pharmaceutically acceptable carrier;

a composition comprising a siRNA identified by SEQ ID NO. 6, a siRNA with the sequence of SEQ ID NO. 21, a siRNA identified by SEQ ID NO. 16 and a pharmaceutically acceptable carrier; and a composition comprising a siRNA identified by SEQ ID NO. 6, a siRNA with the sequence of SEQ ID NO. 21, a siRNA identified by SEQ ID NO. 18 and a pharmaceutically acceptable carrier.

Paragraph 113. A composition selected from the group consisting of:

a composition comprising a siRNA identified by SEQ ID NO. 2, a siRNA identified by SEQ ID NO. 9, and a pharmaceutically acceptable carrier;

a composition comprising a siRNA identified by SEQ ID NO. 2, a siRNA identified by SEQ ID NO. 11, and a pharmaceutically acceptable carrier;

a composition comprising a siRNA identified by SEQ ID NO. 2, a siRNA with the sequence of SEQ ID NO. 21, and a pharmaceutically acceptable carrier;

a composition comprising a siRNA identified by SEQ ID NO. 4, a siRNA identified by SEQ ID NO. 9, and a pharmaceutically acceptable carrier;

a composition comprising a siRNA identified by SEQ ID NO. 4, a siRNA identified by SEQ ID NO. 11, and a pharmaceutically acceptable carrier;

a composition comprising a siRNA identified by SEQ ID NO. 4, a siRNA with the sequence of SEQ ID NO. 21, and a pharmaceutically acceptable carrier;

a composition comprising a siRNA identified by SEQ ID NO. 6, a siRNA identified by SEQ ID NO. 9, and a pharmaceutically acceptable carrier;

a composition comprising a siRNA identified by SEQ ID NO. 6, a siRNA identified by SEQ ID NO. 11, and a pharmaceutically acceptable carrier;

a composition comprising a siRNA identified by SEQ ID NO. 6, a siRNA with the sequence of SEQ ID NO. 21, and a pharmaceutically acceptable carrier;

a composition comprising a siRNA identified by SEQ ID NO. 2, a siRNA identified by SEQ ID NO. 14, and a pharmaceutically acceptable carrier;

a composition comprising a siRNA identified by SEQ ID NO. 2, a siRNA identified by SEQ ID NO. 16, and a pharmaceutically acceptable carrier;

a composition comprising a siRNA identified by SEQ ID NO. 4, a siRNA identified by SEQ ID NO. 14, and a pharmaceutically acceptable carrier;

a composition comprising a siRNA identified by SEQ ID NO. 4, a siRNA identified by SEQ ID NO. 16, and a pharmaceutically acceptable carrier;

a composition comprising a siRNA identified by SEQ ID NO. 6, a siRNA identified by SEQ ID NO. 14, and a pharmaceutically acceptable carrier; and a composition comprising a siRNA identified by SEQ ID NO. 6, a siRNA identified by SEQ ID NO. 16, and a pharmaceutically acceptable carrier.

Paragraph 114. The composition of paragraph 112 or 113, further comprising one or more additional nucleic acid molecules that induce RNA interference and decrease the expression of a gene of interest.

Paragraph 115. The composition of paragraph 114, wherein at least one of the one or more additional nucleic acid molecules decreases the expression of a gene that promotes angiogenesis.

Paragraph 116. The composition of paragraph 114, wherein at least one of the one or more additional nucleic acid molecules decreases the expression of a gene selected from the group consisting of: VEGFR1, VEGFR2, VEGFR3, PDGF, PDGFR-α, PDGFR-β, EGF, EGFR, RAF-a, RAF-c, AKT, RAS, NFkB, HIF, bFGF, bFGFR, Her-2, c-Met, c-Myc and HGF.

Paragraph 117. The composition of paragraph 112 or 113, wherein the carrier is a nucleic acid delivery vehicle.

Paragraph 118. The composition of paragraph 117, wherein the nucleic acid delivery vehicle is synthetic.

Paragraph 119. The composition of paragraph 118 wherein the synthetic nucleic acid delivery vehicle comprises a core region comprising a cationic polymer and the nucleic acid.

Paragraph 120. The composition of paragraph 119, wherein the cationic polymer is polyethyleneimine.

Paragraph 121. The composition of paragraph 119, wherein the cationic polymer is a histidine-lysine co-polymer.

Paragraph 122. The composition of paragraph 119, wherein the synthetic nucleic acid delivery vehicle further comprises a protective hydrophilic layer.

Paragraph 123. The composition of paragraph 122, wherein the protective hydrophilic layer comprises a component selected from the group consisting of: polyethylene glycol, a polyacetal and a polyoxazoline.

Paragraph 124. The composition of paragraph 119, wherein the synthetic nucleic acid vehicle further comprises a targeting moiety.

Paragraph 125. The composition of paragraph 122, wherein the synthetic nucleic acid vehicle further comprises a targeting moiety.

Paragraph 126. The composition of paragraph 124, wherein the targeting moiety binds a tumor specific molecule or an angiogenesis-specific molecule.

Paragraph 127. The composition of paragraph 122, wherein the targeting moiety binds endothelial cells.

Paragraph 128. The composition of paragraph 127, wherein the targeting moiety binds an integrin on vascular endothelial cells.

Paragraph 129. The composition of paragraph 128, wherein the targeting moiety is a peptide comprising the amino acid sequence RGD.

Paragraph 130. The composition of paragraph 129, wherein the peptide comprising RGD is a cyclic peptide.

Paragraph 131. The composition of paragraph 128, wherein the synthetic nucleic acid delivery vehicle comprises:
(a) a core region comprising PEI;
(b) a protective hydrophilic layer comprising PEG; and
(c) a cyclic RGD-containing peptide targeting moiety.

Paragraph 132. The composition of paragraph 112 or 113 comprising an additional therapeutic agent selected from the group consisting of: an anti-cancer agent, an anti-inflammatory agent and an anti-infective agent.

Paragraph 133. The composition of paragraph 112 or 113 comprising an anti-angiogenic agent.

Paragraph 134. The composition of paragraph 133, wherein the anti-angiogenic agent is an inhibitor selected from the group consisting of: an inhibitor of human VEGF, an inhibitor of human VEGFR1 and an inhibitor of human VEGFR2.

Paragraph 135. A method for reducing neovascularization in a subject in need thereof comprising the step of administering to the subject the composition of paragraph 112 or 113.

Paragraph 136. A method for reducing neovascularization in a subject in need thereof comprising the step of administering to the subject the composition of paragraph 131.

Paragraph 137. A method of reducing tumor growth in a subject in need thereof, comprising the step of administering to the subject the composition of paragraph 112 or 113.

Paragraph 138. A method of reducing tumor growth in a subject in need thereof, comprising the step of administering to the subject the composition of paragraph 131.

Paragraph 139. A method for decreasing one or more of VEGF, VEGFR1 or VEGFR2 protein levels in a cell comprising introducing into the cell the composition of paragraph 112.

Paragraph 140. A method for decreasing the protein level of VEGF or VEGFR1, or of both VEGF and VEGFR1, in a cell comprising introducing into the cell the composition of paragraph 113.

Paragraph 141. A method for decreasing the protein level of VEGF or VEGFR2, or of both VEGF and VEGFR2, in a cell comprising introducing into the cell the composition of paragraph 113.

There also has been provided a method for treating a disease in a mammal associated with undesirable expression of a VEGF pathway gene, comprising applying a nucleic acid composition comprising a dsRNA oligonucleotide, as the active pharmaceutical ingredient (API), associated with a formulation, wherein the formulation can comprise a polymer, where the nucleic acid composition is capable of reducing expression of the VEGF pathway genes and inhibiting NV in the disease. The disease may be cancer or a precancerous growth and the tissue may be, for example, a kidney tissue, breast tissue, colon tissue, a prostate tissue, a lung tissue or an ovarian tissue.

As used herein, "oligonucleotides" and similar terms based on this relate to short oligos composed of naturally occurring nucleotides as well as to oligos composed of synthetic or modified nucleotides. Oligonucleotides may be 10 or more nucleotides in length, or 15, or 16, or 17, or 18, or 19, or 20 or more nucleotides in length, or 21, or 22, or 23, or 24 or more nucleotides in length, or 25, or 26, or 27, or 28 or 29, or 30 or more nucleotides in length, 35 or more, 40 or more, 45 or more, up to about 50, nucleotides in length.

An oligonucleotide that is an siRNA may have any number of nucleotides between 15 and 30 nucleotides. In many embodiments an siRNA may have any number of nucleotides between 19 and 27 nucleotides.

In many embodiments, an siRNA may have two blunt ends, or two sticky ends, or one blunt end with one sticky end. The overhang nucleotides of a sticky end can range from one to four nucleotides or more.

In a preferred embodiment, the invention provides siRNA of 25 base pairs with blunt ends.

The terms "polynucleotide" and "oligonucleotide" are used synonymously herein.

The composition may further comprise a polymeric carrier. The polymeric carrier may comprise a cationic polymer that binds to the RNA molecule and forms nanoparticles. The cationic polymer may be an amino acid copolymer, containing, for example, histidine and lysine residues. The polymer may comprise a branched polymer. The composition may comprise a targeted synthetic vector. The synthetic vector may comprise a cationic polymer as a nucleic acid carrier, a hydrophilic polymer as a steric protective material, and a targeting ligand as a target cell selective agent. The polymer may comprise a polyethyleneimine or a polyhistidine-lysine copolymer or a polylysine modified chemically or other effective polycationic carriers that can be used as the nucleic acid carrier module, the hydrophilic polymer may comprise a polyethylene glycol or a polyacetal or a polyoxazoline, and the targeting ligand may comprise a peptide comprising an RGD sequence or a sugar or a sugar analogue or an mAb or a fragment of an mAb, or any other effective targeting moieties.

In any of these methods, an electric field may be applied to a tissue substantially contemporaneously with the composition or subsequent to application of the composition. The composition and method of the invention comprises dsRNA oligonucleotides with a sequence matching an endogenous VEGF pathway gene or a mutated endogenous gene, and at least one mutation in the mutated gene may be in a coding or regulatory region of the gene. In any of these methods, the endogenous gene may be selected from the group consisting of VEGF pathway genes including growth factor genes, protein serine/threonine kinase genes, protein tyrosine kinase genes, protein serine/threonine phosphatase genes, protein tyrosine phosphatase genes, receptor genes, and transcription factor genes. The selected gene may include one or more genes from the group consisting of VEGF, VEGF-R1, VEGF-R2, VEGF-R3, VEGF121, VEGF165, VEGF 189, VEGF206, RAF-a, RAF-c, AKT, Ras, NF-Kb. The selected gene may include one or more genes from other biochemical pathways associated with NV including HIF, EGF, EGFr, bFGF, bFGFr, PDGF, and PDGFr. The selected gene may include one or more genes from other biochemical pathways operative in concert with NV including Her-2, c-Met, c-Myc and HGF.

The present invention also provides compositions and methods for nucleic acid agents inducing RNAi to inhibit multiple genes including cocktails of siRNA (siRNA-OC). The compositions and methods of the invention may inhibit multiple genes substantially contemporaneously or they may inhibit multiple genes sequentially. In a preferred embodiment siRNA-OC agents inhibit three VEGF pathway genes: VEGF, VEGF receptor 1, and VEGF receptor 2. In another preferred embodiment siRNA-OC are administered substantially contemporaneously. The present invention provides agents with gene inhibition selectivity derived from matching the sequence of the siRNA largely to a sequence in the targeted gene mRNA. It also provides siRNA agents with substantially similar physiochemical properties that inhibit different genes in the VEGF pathway. It also provides nanoparticle compositions largely independent of the siRNA sequence. It also provides methods for treatment of human diseases, especially NV related diseases, which can be treated with inhibitors of multiple endogenous genes. It also provides methods for treatment of human diseases by combinations of therapeutic agents administered substantially contemporaneously in some cases and, in other cases, sequentially.

One aspect of the present invention provides compositions and methods for treatment of cancer, arthritis, blindness, infectious diseases and inflammatory diseases. In another aspect of the present invention nucleic acid agents inducing RNAi are used in concert with other therapeutic agents, such as but not limited to small molecules and monoclonal antibodies (mAb), in the same therapeutic regimen.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 19. Self-assembled nanoparticle for siRNA delivery. When the pre-made RGD-PEG-PEI conjugate aqueous solution is mixed with the siRNA aqueous solution, the nanoparticles will be self-assembled as described. The nanoparticles are relatively homogeneous in size, from 50 nm to 100 nm.

FIG. 27. 25-mer blunted double-stranded siRNA mediated an elongated target gene silencing. MCF7/165 cells overexpressing hVEGF were transfected with either regular 21-mer siRNA (19 basepair siRNA with 3' overhangs) (hVEGF-siRNA-a, FIG. 27 A, B, C) or 25-mer siRNA targeting hVEGF (hVEGF-25-siRNA-a, FIG. 27A; hVEGF-25-siRNA-b, FIG. 27B; and hVEGF-25-siRNA-C, FIG. 27C). The culture media from the transfected cells were harvested at indicated time points post siRNA transfection and the VEGF protein levels were measured using a commercial hVEGF ELISA kit. Data were presented as Mean+/−SD.

DETAILED DESCRIPTION

Figure 1:
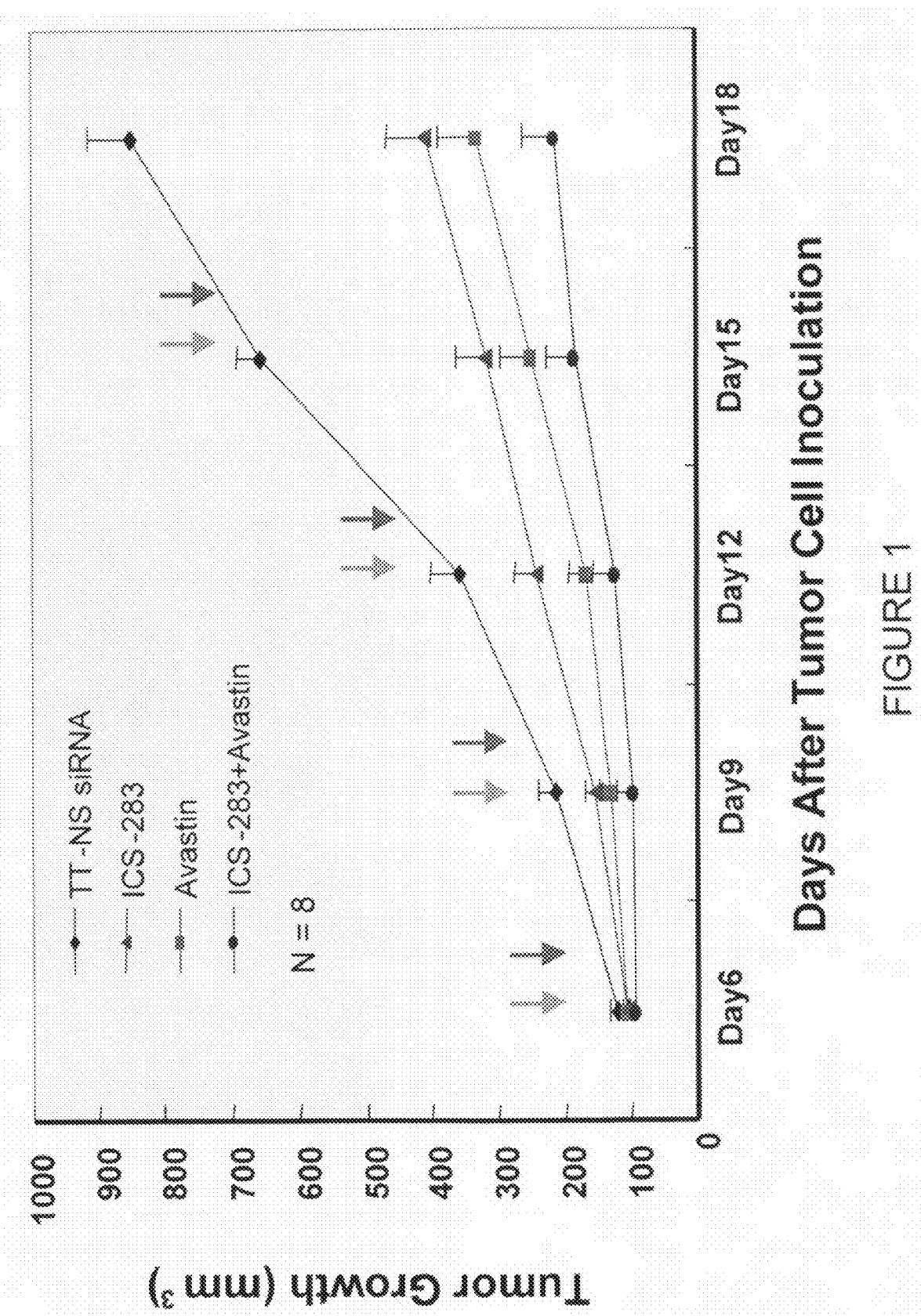
FIG. 1 shows the inhibition of DLD-1 colon xenograft tumor growth by VEGF pathway siRNA nanoparticle compositions targeted by an RGD peptide ligand alone or in combination with Avastin treatment. Stronger anti-tumor efficacy has been observed using a combination cancer therapeutics with VEGFR2-siRNA inhibitor and Avastin (Bevacizumab) in the same treatment regimen, in a human colon carcinoma (DLD-1) xenograft tumor model.

The present invention provides compositions and methods for treatment of NV diseases, which typically are characterized by attributes of multiple proteins and abnormally overexpressed disease-causing genes and multiple malfunctions of disease-causing proteins. The present invention provides nucleic acid agents, such as siRNA oligonucleotides, that activate RNA interference (RNAi) and are highly selective inhibitors of gene expression with a sequence specific manner. The present invention provides inhibition of NV by modulation of protein activity including reduction of protein expression levels and post transcriptional modification of proteins.

In cancer, the tumorigenesis process is thought to be the result of abnormal over-expression of oncogenes, angiogenesis factors, growth factors, and mutant tumor suppressors, even though under-expression of other proteins also plays a critical role. Increasing evidences supports the notion that siRNA molecules are able to "knockdown" tumorigenic genes both in vitro and in vivo, resulting in significant anti-tumor effects. The compositions and methods of the present invention demonstrate substantial knockdown of human VEGF in MCF-7 cells, MDA-MB-435 cells and 1483 cell-induced xenograft tumor models, achieving tumor growth inhibition of 40-80%, using intratumoral delivery of siRNA specifically targeting human VEGF pathway gene sequences. It is appreciated that inhibition of VEGF pathway gene expression induces anti-angiogenesis effects that alter the microvasculature in tumors and that activate tumor cell apoptosis and can enhance efficacy of cytotoxic chemotherapeutic drugs. However, to achieve significantly improved antitumor efficacy of anti-angiogenesis agents and chemotherapeutic drugs, a highly effective delivery method is necessary so that elevated concentrations of the drugs accumulate in the local tumor tissue, and in many instances through a systemic administration.

The present inventors have described a method of validating drug targets that determines which targets control disease pathways and therefore justify drug development efforts (see PCT/US02/31554). The present inventors also have described technologies suitable for delivery of nucleic acids into animal tissues. See WO01/47496, the contents of which are hereby incorporated by reference in their entirety. These methods enable administration of nucleic acid and achieve a significant (for example, seven-fold) increase in efficiency compared to "gold standard" nucleotide delivery reagents. Accordingly, the methods provide strong activity of nucleic acids in tissues including activity of candidate target proteins. This platform is a powerful tool for validation of candidate genes in a tissue.

In addition, the present inventors have used these methods to achieve gene silencing in animal tissues, which is highly desired for validation of candidate target genes and as a therapeutic modality. Recently, double stranded RNA has been demonstrated to induce gene-specific silencing by a phenomenon called RNA interference (RNAi). Although the mechanism of RNAi still is not completely understood, early results suggested that the RNAi effect may be achieved in vitro in various cell types including mammalian cells. A double stranded RNA targeted against a target mRNA results in the degradation of the target, thereby causing the silencing of the corresponding gene. Large double stranded RNA is cleaved into smaller fragments of 21-23 nucleotides long by an RNase III like activity involving an enzyme Dicer. These shorter fragments, known as siRNA (small interfering RNA), are believed to mediate the cleavage of mRNA.

Although gene down-regulation by the RNAi mechanism has been studied in *C. elegans* and other lower organisms in recent past, its effectiveness in mammalian cells in culture has only recently been demonstrated. An RNAi effect recently was demonstrated in mouse using the firefly luciferase gene reporter system. To develop an RNAi technology platform for in vivo gene inhibition for research and for clinical application of nucleic acid therapeutics to treat human diseases, the present inventors performed several in vivo studies in mouse models of disease. In those experiments, either siRNA or dsRNA targeting a tumor related ligand (human VEGF) or receptor (mouse VEGFR2) was delivered to nude mice bearing xenografted human MCF-7 derived tumor or human MDA-MB-435 tumors. For the first time we were able to demonstrate that RNAi can effectively silencing target gene in tumor cells in vivo and that, as a result, tumor growth was inhibited.

The present inventors have achieved for the first time therapeutic compositions and methods for treatment of a wide variety of NV diseases using dsRNA oligonucleotides inhibiting VEGF pathway genes. The invention is described here in detail, but one skilled in the art will appreciate the full extent of the invention.

A. Potent siRNA for VEGF Pathway Gene Inhibition

The present invention provides nucleic acid agents targeting and inhibiting VEGF pathway gene sequences with a variety of physicochemical structures. One preferred embodiment of the present invention uses nucleic acid agents called siRNA including 19 base pair dsRNA with 3' overhangs and 25 base pair dsRNA with blunt ends. The siRNA of the invention with 25 base pair dsRNA with blunt ends were found to be some of the most potent inhibitors with some of the greatest duration of inhibition. Additionally, incorporation of non-naturally occurring chemical analogues are useful in the invention, including 2'-O-Methyl ribose analogues of RNA, DNA and RNA chimeric oligonucleotides, and other chemical analogues of nucleic acid oligonucleotides. The 25 basepair siRNA with and without 2'-O-Methyl ribose in the sense strand of the siRNA and targeting human VEGF sequence provide strong and durable inhibitory effect, up to 70-80% in MCF-7/VEGF165 cells and in tumors growing in animals. This inhibitory effect in MCF-7/VEGF165 cell culture lasted for 5 days. One aspect provided for by the invention is siRNA targeting human genes and the encoded sequence also targets other mammalian species such as other primates, mice, and rats but not limited to these species. Methods well known to one skilled in the art can be used to identify and select siRNA provided by the invention. Many other forms of siRNA targeting VEGF pathway genes are provided for by the invention and others will be understood by one skilled in the art.

a. Human VEGF specific siRNA:

25 base pair blunt ends:

```
hVEGF-25-siRNA-a:
Sense strand:
5'-r(CCUGAUGAGAUCGAGUACAUCUUCA)-3'     (SEQ ID NO: 1)

Antisense strand:
5'-r(UGAAGAUGUACUCGAUCUCAUCAGG)-3'.    (SEQ ID NO: 2)

hVEGF-25-siRNA-b:
Sense strand:
5'-r(GAGAGAUGAGCUUCCUACAGCACAA)-3'     (SEQ ID NO: 3)

Antisense strand:
5'-r(UUGUGCUGUAGGAAGCUCAUCUCUC)-3'.    (SEQ ID NO: 4)

hVEGF-25-siRNA-c:
Sense strand:
5'-r(CACAACAAAUGUGAAUGCAGACCAA)-3'     (SEQ ID NO: 5)

Antisense strand:
5'-r(UUGGUCUGCAUUCACAUUUGUUGUG)-3'     (SEQ ID NO: 6)
```

19 base pairs with two nucleotide (TT) overhangs at 3':

```
                                          (SEQ ID NO: 7)
    hVEGF165 5'-r (UCGAGACCCUGGUGGACAUTT)-3'
``` b. Human VEGF receptor 1 specific siRNA:
25 base pair blunt ends:

```
hVEGFR1-25-siRNA-a,
Sense strand:
                                        (SEQ ID NO: 8)
5'-r(GCCAACAUAUUCUACAGUGUUCUUA)-3'

Antisense strand:
                                        (SEQ ID NO: 9)
5'-r(UAAGAACACUGUAGAAUAUGUUGGC)-3' hVEGFR1-25-siRNA-b,
Sense strand:
                                        (SEQ ID NO: 10)
5'-r(CCCUCGCCGGAAGUUGUAUGGUUAA)-3'

Antisense strand:
                                        (SEQ ID NO: 11)
5'-r(UUAACCAUACAACUUCCGGCGAGGG)-3'.
```

19 basepairs with 2 3' (TT) nucleotide overhangs:

```
                                        (SEQ ID NO: 12)
VEGF R1 (FLT) 5'-GGAGAGGACCUGAAACUGUTT
``` c. Human VEGF receptor 2 specific siRNA:
25 basepair blunt ends:

```
hVEGFR2-25-siRNA-a,
Sense strand:
                                        (SEQ ID NO: 13)
5'-r(CCUCUUCUGUAAGACACUCACAAUU)-3'

Antisense strand:
                                        (SEQ ID NO: 14)
5'-r(AAUUGUGAGUGUCUUACAGAAGAGG)-3'.

hVEGFR2-25-siRNA-b,
Sense strand:
                                        (SEQ ID NO: 15)
5'-r(CCCUUGAGUCCAAUCACACAAUUAA)-3'

Antisense strand:
                                        (SEQ ID NO: 16)
5'-r(UUAAUUGUGUGAUUGGACUCAAGGG)-3'.

hVEGFR2-25--siRNA-c,
Sense strand:
                                        (SEQ ID NO: 17)
5'-r(CCAAGUGAUUGAAGCAGAUGCCUUU)-3'

Antisense strand:
                                        (SEQ ID NO: 18)
5'-r(AAAGGCAUCUGCUUCAAUCACUUGG)-3'.
```

19 basepairs with 2 3' (TT) nucleotide overhangs:

```
                                        (SEQ ID NO: 19)
hVEGF R2 (KDR) 5'-CAGUAAGCGAAAGAGCCGGTT-3'
```

In another embodiment, the siRNA targeting human VEGF receptor 1 has the following sequence:

```
Sense strand:
                                        (SEQ ID NO: 20)
5'-r(CCUCAAGAGCAAACGUGACUUAUUU)-3'

Antisense strand:
                                        (SEQ ID NO: 21)
5'-r(AAAUAAGUCACGUUUGCUCUUGAGG)-3'.
```

25 Base Pair siRNA Oligos can Target the Corresponding Genes from Both Human and Mouse.

In another embodiment, the 25 base pair siRNA sequences were selected to against the corresponding mRNA sequences, including human VEGF, VEGFR1, VEGFR2, PDGFR-alpha, PDGFR-beta and EGFR genes. The sequences selected are not only specific to the human genes but also specific to the corresponding mouse genes, such as the sequences against human VEGF mRNAs are also against mouse VEGF mRNAs.

The 25 base pair siRNA oligos are very useful for mouse xenograft tumor study since the anti-tumor efficacy relies on knockdown both human and mouse genes in the tumor tissue. For example, knockdown VEGF expressions from both tumor cells (human origin) and endothelium cells (mouse origin) with the siRNA oligos targeting both sequences will provide better anti-tumor efficacy.

Meanwhile, the toxicity study with the siRNA oligos targeting both genes from testing animals (e.g. mouse or monkey) and human genes will be very useful since the actual drugs were tested for both drug agent toxicology and exaggerated pharmacology.

The following sequences are the 25 base pair siRNA oligo sequences targeting VEGF, VEGFR2, VEGFR1, PDGFR-alpha, PDGFR-beta and EGFR mRNAs from both human and mouse genes, some of them can also target to their monkey and dog counterparts.

25 Base Pair VEGF siRNA Targeting Human, Mouse, Rat, Macaque, Dog VEGF mRNA Sequences:

```
mhVEGF25-1:
sense,
5'-CAAGAUCCGCAGACGUGUAAAUGUU-3';      (SEQ ID NO. 22)

antisense,
5'-AAC AUUUACACGUCUGCGGAUCUUG-3'      (SEQ ID NO. 23)

mhVEGF25-2:
sense,
5'-GCAGCUUGAGUUAAACGAACGUACU-3';      (SEQ ID NO. 24)

antisense,
5'-AGUACGUUCGUUUAACUCAAGCUGC-3'       (SEQ ID NO. 25)

mhVEGF25-3:
sense,
5'-CAGCUUGAGUUAAACGAACGUACUU-3';      (SEQ ID NO. 26)

antisense,
5'-AAGUACGUUCGUUUAACUCAAGCUG-3'       (SEQ ID NO. 27)

mhVEGF25-4:
sense,
5'-CCAUGCCAAGUGGUCCCAGGCUGCA-3';      (SEQ ID NO. 28)

antisense,
5'-TGCAGCCUGGGACCACUUGGCAUGG-3'       (SEQ ID NO. 29)

mhVEGF25-4:
sense,
5'-CACAUAGGAGAGAUGAGCUUCCUCA-3';      (SEQ ID NO. 30)

antisense,
5'-UGAGGAAGCUCAUCUCUCCUAUGUG-3'       (SEQ ID NO. 31)
```

25 Base Pair VEGF R2 siRNA Sequences Targeting Both Human and Mouse VEGFR2 mRNA Sequences:

```
mhVEGFR225-1:
sense,
5'-CCUACGGACCGUUAAGCGGGCCAAU-3';      (SEQ ID NO. 32)
```

-continued antisense:
5'-AUUGGCCCGCUUAACGGUCCGUAGG-3'     (SEQ ID NO. 33)

mhVEGFR225-2:
sense,
5'-CUCAUGUCUGUUCUCAAGAUCCUCA-3';    (SEQ ID NO. 34)

antisense:
5'-UGAGGAUCUUGAGAACAGACAUGAG-3'     (SEQ ID NO. 35)

mhVEGFR225-3:
sense,
5'-CUCAUGGUGAUUGUGGAAUUCUGCA-3';    (SEQ ID NO. 36)

antisense:
5'-UGCAGAAUUCCACAAUCACCAUGAG-3'     (SEQ ID NO. 37)

mhVEGFR225-4:
sense,
5'-GAGCAUGGAAGAGGAUUCUGGACUC-3';    (SEQ ID NO. 38)

antisense:
5'-GAGUCCAGAAUCCUCUUCCAUGCUC-3'     (SEQ ID NO. 39)

mhVEGFR225-5:
sense,
5'-CAGAACAGUAAGCGAAAGAGCCGGC-3';    (SEQ ID NO. 40)

antisense:
5'-GCCGGCUCUUUCGCUUACUGUUCUG-3'     (SEQ ID NO. 41)

mhVEGFR225-6:
sense,
5'-GACUUCCUGACCUUGGAGCAUCUCA-3';    (SEQ ID NO. 42)

antisense:
5'-UGAGAUGCUCCAAGGUCAGGAAGUC-3'     (SEQ ID NO. 43)

mhVEGFR225-7:
sense,
5'-CCUGACCUUGGAGCAUCUCAUCUGU-3';    (SEQ ID NO. 44)

antisense:
5'-ACAGAUGAGAUGCUCCAAGGUCAGG-3'     (SEQ ID NO. 45)

mhVEGFR225-8:
sense,
5'-GCUAAGGGCAUGGAGUUCUUGGCAU-3';    (SEQ ID NO. 46)

antisense:
5'-AUGCCAAGAACUCCAUGCCCUUAGC-3'     (SEQ ID NO. 47)

25 Base Pairs VEGF R1 siRNA Sequences Targeting Both Human and Mouse VEGFR1 mRNA Sequences:

mhVEGFR125-1:
sense,
5'-CACGCUGUUUAUUGAAAGAGUCACA-3';    (SEQ ID NO. 48)

antisense:
5'-UGUGACUCUUUCAAUAAACAGCGUG-3'     (SEQ ID NO. 49)

mhVEGFR125-2:
sense,
5'-CGCUGUUUAUUGAAAGAGUCACAGA-3';    (SEQ ID NO. 50)

antisense:
5'-UCUGUGACUCUUUCAAUAAACAGCG-3'     (SEQ ID NO. 51)

mhVEGFR125-3:
sense,
5'-CAAGGAGGGCCUCUGAUGGUGAUGU-3';    (SEQ ID NO. 52)

antisense:
5'-ACAUCACCAUCAGAGGCCCUCCUUG-3'     (SEQ ID NO. 53)

mhVEGFR125-4:
sense,
5'-CCAACUACCUCAAGAGCAAACGUGA-3';    (SEQ ID NO. 54)

antisense:
5'-UCACGUUUGCUCUUGAGGUAGUUGG-3'     (SEQ ID NO. 55)

mhVEGFR125-5:
sense,
5'-CUACCUCAAGAGCAAACGUGACUUA-3';    (SEQ ID NO. 56)

antisense:
5'-UAAGUCACGUUUGCUCUUGAGGUAG-3'     (SEQ ID NO. 57)

mhVEGFR125-6:
sense,
5'-CCAGAAAGUGCAUUCAUCGGGACCU-3';    (SEQ ID NO. 58)

antisense:
5'-AGGUCCCGAUGAAUGCACUUUCUGG-3'     (SEQ ID NO. 59)

mhVEGFR125-7:
sense,
5'-CAUUCAUCGGGACCUGGCAGCGAGA-3';    (SEQ ID NO. 60)

antisense:
5'-UCUCGCUGCCAGGUCCCGAUGAAUG-3'     (SEQ ID NO. 61)

mhVEGFR125-8:
sense,
5'-CAUCGGGACCUGGCAGCGAGAAACA-3';    (SEQ ID NO. 62)

antisense:
5'-UGUUUCUCGCUGCCAGGUCCCGAUG-3'     (SEQ ID NO. 63)

mhVEGFR125-9:
sense,
5'-GAGCCUGGAAAGAAUCAAAACCUUU-3';    (SEQ ID NO. 64)

antisense:
5'-AAAGGUUUUGAUUCUUUCCAGGCUC-3'     (SEQ ID NO. 65)

mhVEGFR125-10:
sense,
5'-GCCUGGAAAGAAUCAAAACCUUUGA-3';    (SEQ ID NO. 66)

antisense:
5'-UCAAAGGUUUUGAUUCUUUCCAGGC-3'     (SEQ ID NO. 67)

mhVEGFR125-11:
sense,
5'-GCCUGGAAAGAAUCAAAACCUUUGA-3';    (SEQ ID NO. 68)

antisense:
5'-UCAAAGGUUUUGAUUCUUUCCAGGC-3'     (SEQ ID NO. 69)

mhVEGFR125-12:
sense,
5'-CUGAACUGAGUUUAAAAGGCACCCA-3';    (SEQ ID NO. 70)

antisense:
5'-UGGGUGCCUUUUAAACUCAGUUCAG-3'     (SEQ ID NO. 71)

mhVEGFR125-13:
sense,
5'-GAACUGAGUUUAAAAGGCACCCAGC-3';    (SEQ ID NO. 72)

antisense:
5'-GCUGGGUGCCUUUUAAACUCAGUUG-3'     (SEQ ID NO. 73)

25 Base Pairs siRNA Sequences Targeting Both Human and Mouse PDGFR-Alpha:

mhPDGFRa25-1:
sense,
5'-GAAGAUAAUGACUCACCUGGGGCCA-3';    (SEQ ID NO. 74)

-continued antisense:
5'-UGGCCCCAGGUGAGUCAUUAUCUUC-3' (SEQ ID NO. 75)

mhPDGFRa25-2:
sense,
5'-GAUAAUGACUCACCUGGGGCCACAU-3'; (SEQ ID NO. 76)

antisense:
5'-AUGUGGCCCCAGGUGAGUCAUUAUC-3' (SEQ ID NO. 77)

mhPDGFRa25-3:
sense,
5'-CUCACCUGGGGCCACAUUUGAACAU-3'; (SEQ ID NO. 78)

antisense:
5'-AUGUUCAAAUGUGGCCCCAGGUGAG-3' (SEQ ID NO. 79)

mhPDGFRa25-4:
sense,
5'-CUUGCUGGGAGCCUGCACCAAGUCA-3'; (SEQ ID NO. 80)

antisense:
5'-UGACUUGGUGCAGGCUCCCAGCAAG-3' (SEQ ID NO. 81)

mhPDGFRa25-5:
sense,
5'-GAUUCUACUUUCUACAAUAAGAUCA-3'; (SEQ ID NO. 82)

antisense:
5'-UGAUCUUAUUGUAGAAAGUAGAAUC-3' (SEQ ID NO. 83)

mhPDGFRa25-6:
sense,
5'-CAGAGACUGAGCGCUGACAGUGGCU-3'; (SEQ ID NO. 84)

antisense:
5'-AGCCACUGUCAGCGCUCAGUCUCUG-3' (SEQ ID NO. 85)

mhPDGFRa25-7:
sense,
5'-GACCUGGGCAAGAGGAACAGACACA-3'; (SEQ ID NO. 86)

antisense:
5'-UGUGUCUGUUCCUCUUGCCCAGGUC-3' (SEQ ID NO. 87)

mhPDGFRa25-8:
sense,
5'-CCACCUUCAUCAAGAGAGGACGA-3'; (SEQ ID NO. 88)

antisense:
5'-UCGUCCUCUCUUGAUGAAGGUGG-3' (SEQ ID NO. 89)

mhPDGFRa25-9:
sense,
5'-UAUGGAUUAAGCCGGUCCCAACCUGU-3'; (SEQ ID NO. 90)

antisense:
5'-ACAGGUUGGGACCGGCUUAAUCCAUA-3' (SEQ ID NO. 91)

25 Base Pairs siRNA Sequences Targeting Both Human and Mouse PDGFRbeta:

mhPDGFRB25-1:
sense,
5'-CUGCAGAGACCUCAAAAGGUGUCCA-3'; (SEQ ID NO. 92)

antisense:
5'-UGGACACCUUUUGAGGUCUCUGCAG-3' (SEQ ID NO. 93)

mhPDGFRB25-2:
sense,
5'-CAGAGACCUCAAAAGGUGUCCACGU-3'; (SEQ ID NO. 94)

antisense:
5'-ACGUGGACACCUUUUGAGGUCUCUG-3' (SEQ ID NO. 95)

-continued mhPDGFRB25-3:
sense,
5'-GUGGUGGUGAUCUCAGCCAUCCUGG-3'; (SEQ ID NO. 96)

antisense:
5'-CCAGGAUGGCUGAGAUCACCACCAC-3' (SEQ ID NO. 97)

mhPDGFRB25-4:
sense,
5'-GGUGGUGAUCUCAGCCAUCCUGGCC-3'; (SEQ ID NO. 98)

antisense:
5'-GGCCAGGAUGGCUGAGAUCACCACC-3' (SEQ ID NO. 99)

mhPDGFRB25-5:
sense,
5'-GGCAAGCUGGUCAAGAUCUGUGACU-3'; (SEQ ID NO. 100)

antisense:
5'-AGUCACAGAUCUUGACCAGCUUGCC-3' (SEQ ID NO. 101)

mhPDGFRB25-6:
sense,
5'-GCAAGCUGGUCAAGAUCUGUGACUU-3'; (SEQ ID NO. 102)

antisense:
5'-AAGUCACAGAUCUUGACCAGCUUGC-3' (SEQ ID NO. 103)

mhPDGFRB25-7:
sense,
5'-GGGUGGCACCCCUUACCCAGAGCUG-3'; (SEQ ID NO. 104)

antisense:
5'-CAGCUCUGGGUAAGGGGUGCCACCC-3' (SEQ ID NO. 105)

mhPDGFRB25-8:
sense,
5'-GCACCCCUUACCCAGAGCUGCCCAU-3'; (SEQ ID NO. 106)

antisense:
5'-AUGGGCAGCUCUGGGUAAGGGGUGC-3' (SEQ ID NO. 107)

mhPDGFRB25-9:
sense,
5'-CUUACCCAGAGCUGCCCAUGAACGA-3' (SEQ ID NO. 108)

antisense:
5'-UCGUUCAUGGGCAGCUCUGGGUAAG-3' (SEQ ID NO. 109)

mhPDGFRB25-10:
sense,
5'-CAUGCCUCCGACGAGAUCUAUGAGA-3'; (SEQ ID NO. 110)

antisense:
5'-UCUCAUAGAUCUCGUCGGAGGCAUG-3' (SEQ ID NO. 111)

mhPDGFRB25-11:
sense,
5'-GCCUCCGACGAGAUCUAUGAGAUCA-3'; (SEQ ID NO. 112)

antisense:
5'-UGAUCUCAUAGAUCUCGUCGGAGGC-3' (SEQ ID NO. 113)

mhPDGFRB25-12:
sense,
5'-CCGACGAGAUCUAUGAGAUCAUGCA-3'; (SEQ ID NO. 114)

antisense:
5'-UGCAUGAUCUCAUAGAUCUCGUCGG-3' (SEQ ID NO. 115)

mhPDGFRB25-13:
sense,
5'-GACGAGAUCUAUGAGAUCAUGCAGA-3'; (SEQ ID NO. 116)

antisense:
5'-UCUGCAUGAUCUCAUAGAUCUCGUC-3' (SEQ ID NO. 117)

25 Base Pairs siRNA Sequences Targeting Both Human and Mouse EGFR:

```
mhEGFR-1:
sense,
5'-CUCUGGAUCCCAGAAGGUGAGAAAG-3';    (SEQ ID NO. 118)

antisense:
5'-CUUUCUCACCUUCUGGGAUCCAGAG-3'     (SEQ ID NO. 119)

mhEGFR-2:
sense,
5'-CAGCAUGUCAAGAUCACAGAUUUUG-3';    (SEQ ID NO. 120)

antisense:
5'-CAAAAUCUGUGAUCUUGACAUGCUG-3'     (SEQ ID NO. 121)

mhEGFR-3:
sense,
5'-GAUCACAGAUUUUGGGCUGGCCAAA-3';    (SEQ ID NO. 122)

antisense:
5'-UUUGGCCAGCCCAAAAUCUGUGAUC-3'     (SEQ ID NO. 123)

mhEGFR-4:
sense,
5'-CAGAUUUUGGGCUGGCCAAACUGCU-3';    (SEQ ID NO. 124)

antisense:
5'-AGCAGUUUGGCCAGCCCAAAAUCUG-3'     (SEQ ID NO. 125)

mhEGFR-5:
sense,
5'-C AAAGUGCCUAUCAAGUGGAUGGCA-3'    (SEQ ID NO. 126)

antisense:
5'-UGCCAUCCACUUGAUAGGCACUUUG-3'     (SEQ ID NO. 127)

mhEGFR-6:
sense,
5'-CCAUCGAUGUCUACAUGAUCAUGGU-3';    (SEQ ID NO. 128)

antisense:
5'-ACCAUGAUCAUGUAGACAUCGAUGG-3'     (SEQ ID NO. 129)

mhEGFR-7:
sense,
5'-CGAUGUCUACAUGAUCAUGGUCAAGU-3';   (SEQ ID NO. 130)

antisense:
5'-ACUUGACCAUGAUCAUGUAGACAUCG-3'    (SEQ ID NO. 131)

mhEGFR-8:
sense,
5'-CUACAUGAUCAUGGUCAAGUGCUGG-3';    (SEQ ID NO. 132)

antisense:
5'-CCAGCACUUGACCAUGAUCAUGUAG-3'     (SEQ ID NO. 133)

mhEGFR-9:
sense,
5'-CAUGAUCAUGGUCAAGUGCUGGAUGA-3';   (SEQ ID NO. 134)

antisense:
5'-UCAUCCAGCACUUGACCAUGAUCAUG-3'    (SEQ ID NO. 135)

mhEGFR-10:
sense,
5'-GGAUGAAAGAAUGCAUUUGCCAAGU-3';    (SEQ ID NO. 136)

antisense:
5'-ACUUGGCAAAUGCAUUCUUUCAUCC-3'     (SEQ ID NO. 137)

mhEGFR-11:
sense,
5'-GACAACCCUGACUACCAGCAGGACU-3';    (SEQ ID NO. 138)

antisense:
5'-AGUCCUGCUGGUAGUCAGGGUUGUC-3'     (SEQ ID NO. 139)

mhEGFR-12:
sense,
5'-CCUUCUUAAAGACCAUCCAGGAGGU-3';    (SEQ ID NO. 140)

antisense:
5'-ACCUCCUGGAUGGUCUUUAAGAAGG-3'     (SEQ ID NO. 141)
```

Another embodiment is use of a combination of these oligos in the same drug payload. When three or more of those 25 base pair siRNAs targeting three or more genes involving in the disease process were packaged in the same nanoparticles and delivered through the same administration routs (or different routes), the treatment is e more effective since the knockdown of multiple gene expressions can effectively block the particular tumorigenic pathway. The following combinations can be further expended using the same general principles applied here.

Combinations of 25 Base Pair siRNA Oligos, Each of them can Target the Corresponding Genes from Both Human and Mouse, can Achieve More Potent Therapeutic (Multi-targeted) Efficacy:

1. Targeting VEGF Pathways:

VEGF-VEGFR1-VEGFR2 cocktail A:

```
mhVEGF25-1:
sense,
5'-CAAGAUCCGCAGACGUGUAAAUGUU-3';    (SEQ ID NO. 142)

antisense,
5'-AACAUUUACACGUCUGCGGAUCUUG-3'     (SEQ ID NO. 143)

mhVEGFR125-3:
sense,
5'-CAAGGAGGGCCUCUGAUGGUGAUGU-3';    (SEQ ID NO. 144)

antisense:
5'-ACAUCACCAUCAGAGGCCCUCCUUG-3'     (SEQ ID NO. 145)

mhVEGFR225-1:
sense,
5'-CCUACGGACCGUUAAGCGGGCCAAU-3';    (SEQ ID NO. 146)

antisense:
5'-AUUGGCCCGCUUAACGGUCCGUAGG-3'     (SEQ ID NO. 147)
```

VEGF-VEGFR1-VEGFR2 cocktail B:

```
mhVEGF25-1:
sense,
5'-CAAGAUCCGCAGACGUGUAAAUGUU-3';    (SEQ ID NO. 148)

antisense,
5'-AACAUUUACACGUCUGCGGAUCUUG-3'     (SEQ ID NO. 149)

mhVEGFR125-6:
sense,
5'-CCAGAAAGUGCAUUCAUCGGGACCU-3';    (SEQ ID NO. 150)

antisense:
5'-AGGUCCCGAUGAAUGCACUUUCUGG-3'     (SEQ ID NO. 151)

mhVEGFR225-2:
sense,
5'-CUCAUGUCUGUUCUCAAGAUCCUCA-3';    (SEQ ID NO. 152)

antisense:
5'-UGAGGAUCUUGAGAACAGACAUGAG-3'     (SEQ ID NO. 153)
```

VEGF-VEGFR1-VEGFR2 cocktail C:

```
mhVEGF25-2:
sense,
5'-GCAGCUUGAGUUAAACGAACGUACU-3';    (SEQ ID NO. 154)

antisense,
5'-AGUACGUUCGUUUAACUCAAGCUGC-3'     (SEQ ID NO. 155)

mhVEGFR125-6:
sense,
5'-CCAGAAAGUGCAUUCAUCGGGACCU-3';    (SEQ ID NO. 156)

antisense:
5'-AGGUCCCGAUGAAUGCACUUUCUGG-3'     (SEQ ID NO. 157)

mhVEGFR225-2:
sense,
5'-CUCAUGUCUGUUCUCAAGAUCCUCA-3';    (SEQ ID NO. 158)

antisense:
5'-UGAGGAUCUUGAGAACAGACAUGAG-3'     (SEQ ID NO. 159)
```

Many other combinations with the 25 base pair siRNA oligos targeting VEGF, VEGFR1 and VEGFR2 respectively can be composed for the best anti-angiogenesis efficacy, by either equal or different ratios of each components.

2. Targeting Both VEGF and EGF Pathways:

VEGF-VEGFR2-EGFR cocktail A:

```
mhVEGF25-1:
sense,
5'-CAAGAUCCGCAGACGUGUAAAUGUU-3';    (SEQ ID NO. 160)

antisense,
5'-AACAUUUACACGUCUGCGGAUCUUG-3'     (SEQ ID NO. 161)

mhVEGFR225-1:
sense,
5'-CCUACGGACCGUUAAGCGGGCCAAU-3';    (SEQ ID NO. 162)

antisense:
5'-AUUGGCCCGCUUAACGGUCCGUAGG-3'     (SEQ ID NO. 163)

mhEGFR-1:
sense,
5'-CUCUGGAUCCCAGAAGGUGAGAAAG-3';    (SEQ ID NO. 164)

antisense:
5'-CUUUCUCACCUUCUGGGAUCCAGAG-3'     (SEQ ID NO. 165)
```

VEGF-VEGFR2-EGFR cocktail B:

```
mhVEGF25-1:
sense,
5'-CAAGAUCCGCAGACGUGUAAAUGUU-3';    (SEQ ID NO. 166)

antisense,
5'-AACAUUUACACGUCUGCGGAUCUUG-3'     (SEQ ID NO. 167)

mhVEGFR225-2:
sense,
5'-CUCAUGUCUGUUCUCAAGAUCCUCA.3';    (SEQ ID NO. 168)

antisense:
5'-UG AGGAUCUUGAGAACAGACAUGAG-3'    (SEQ ID NO. 169)

mhEGFR-5:
sense,
5'-CAAAGUGCCUAUCAAGUGGAUGGCA-3';    (SEQ ID NO. 170)

antisense:
5'-UGCCAUCCACUUGAUAGGCACUUUG-3'     (SEQ ID NO. 171)
```

VEGF-VEGFR2-EGFR cocktail C:

```
mhVEGF25-2:
sense,
5'-GCAGCUUGAGUUAAACGAACGUACU-3';    (SEQ ID NO. 172)

antisense,
5'-AGUACGUUCGUUUAACUCAAGCUGC-3'     (SEQ ID NO. 173)

mhVEGFR225-2:
sense,
5'-CUCAUGUCUGUUCUCAAGAUCCUCA-3';    (SEQ ID NO. 174)

antisense:
5'-UGAGGAUCUUGAGAACAGACAUGAG-3'     (SEQ ID NO. 175)

mhEGFR-9:
sense,
5'-CAUGAUCAUGGUCAAGUGCUGGAUGA-3';   (SEQ ID NO. 176)

antisense:
5'-UCAUCCAGCACUUGACCAUGAUCAUG-3'    (SEQ ID NO. 177)
```

Many other combinations can be made with other sequences targeting those three genes with different composition and equal or different rations of the siRNA oligos.

3. Targeting VEGF, PDGF and EGF Pathways:

VEGFR2-PDGFRa-EGFR cocktail A:

```
mhVEGFR225-1:
sense,
5'-CCUACGGACCGUUAAGCGGGCCAAU-3'     (SEQ ID NO. 178)

antisense:
5'-AUUGGCCCGCUUAACGGUCCGUAGG-3'     (SEQ ID NO. 179)

mhPDGFRa25-1:
sense,
5'-GAAGAUAAUGACUCACCUGGGGCCA-3';    (SEQ ID NO. 180)

antisense:
5'-UGGCCCCAGGUGAGUCAUUAUCUUC-3'     (SEQ ID NO. 181)

mhEGFR-1:
sense,
5'-CUCUGGAUCCCAGAAGGUGAGAAAG-3';    (SEQ ID NO. 182)

antisense:
5'-CUUUCUCACCUUCUGGGAUCCAGAG-3'     (SEQ ID NO. 183)
```

VEGFR1-VEGFR2-PDGFRa-EGFR cocktail B:

```
mhVEGFR125-6:
sense,
5'-CCAGAAAGUGCAUUCAUCGGGACCU-3';    (SEQ ID NO. 184)

antisense:
5'-AGGUCCCGAUGAAUGCACUUUCUGG-3'     (SEQ ID NO. 185)

mhVEGFR225-1:
sense,
5'-CCUACGGACCGUUAAGCGGGCCAAU-3';    (SEQ ID NO. 186)

antisense:
5'-AUUGGCCCGCUUAACGGUCCGUAGG-3'     (SEQ ID NO. 187)

mhPDGFRa25-2:
sense,
5'-GAUAAUGACUCACCUGGGGCCACAU-3';    (SEQ ID NO. 188)

antisense:
5'-AUGUGGCCCCAGGUGAGUCAUUAUC-3'     (SEQ ID NO. 189)

mhEGFR-1:
sense,
5'-CUCUGGAUCCCAGAAGGUGAGAAAG-3';    (SEQ ID NO. 190)
```

-continued antisense:
5'-CUUUCUCACCUUCUGGGAUCCAGAG-3'   (SEQ ID NO. 191)

VEGFR2-PDGFRa-EGFR cocktail C:

mhVEGFR225-1:
sense,
5'-CCUACGGACCGUUAAGCGGGCCAAU-3';   (SEQ ID NO. 192)

antisense:
5'-AUUGGCCCGCUUAACGGUCCGUAGG-3'   (SEQ ID NO. 193)

mhPDGFRa25-2:
sense,
5'-GAUAAUGACUCACCUGGGGCCACAU-3';   (SEQ ID NO. 194)

antisense:
5'-AUGUGGCCCCAGGUGAGUCAUUAUC-3'   (SEQ ID NO. 195)

mhEGFR-12:
sense,
5'-CCUUCUUAAAGACCAUCCAGGAGGU-3';   (SEQ ID NO. 196)

antisense:
5'-ACCUCCUGGAUGGUCUUUAAGAAGG-3'   (SEQ ID NO. 197)

VEGFR2-PDGFRb-EGFR cocktail A:

mhVEGFR225-1:
sense,
5'-CCUACGGACCGUUAAGCGGGCCAAU-3';   (SEQ ID NO. 198)

antisense:
5'-AUUGGCCCGCUUAACGGUCCGUAGG-3'   (SEQ ID NO. 199)

mhPDGFRB25-5:
sense,
5'-GGCAAGCUGGUCAAGAUCUGUGACU-3';   (SEQ ID NO. 200)

antisense:
5'-AGUCACAGAUCUUGACCAGCUUGCC-3'   (SEQ ID NO. 201)

mhEGFR-1:
sense,
5'-CUCUGGAUCCCAGAAGGUGAGAAAG-3';   (SEQ ID NO. 202)

antisense:
5'-CUUUCUCACCUUCUGGGAUCCAGAG-3'   (SEQ ID NO. 203)

VEGFR2-PDGFRb-EGFR cocktail B:

mhVEGFR225-1:
sense,
5'-CCUACGGACCGUUAAGCGGGCCAAU-3';   (SEQ ID NO. 204)

antisense:
5'-AUUGGCCCGCUUAACGGUCCGUAGG-3'   (SEQ ID NO. 205)

mhPDGFRB25-10:
sense,
5'-CAUGCCUCCGACGAGAUCUAUGAGA-3';   (SEQ ID NO. 206)

antisense:
5'-UCUCAUAGAUCUCGUCGGAGGCAUG-3'   (SEQ ID NO. 207)

mhEGFR-1:
sense,
5'-CUCUGGAUCCCAGAAGGUGAGAAAG-3';   (SEQ ID NO. 208)

antisense:
5'-CUUUCUCACCUUCUGGGAUCCAGAG-3'   (SEQ ID NO. 209)

VEGFR2-PDGFRb-EGFR cocktail C:

mhVEGFR225-1:
sense,
5'-CCUACGGACCGUUAAGCGGGCCAAU-3';   (SEQ ID NO. 210)

antisense:
5'-AUUGGCCCGCUUAACGGUCCGUAGG-3'   (SEQ ID NO. 211)

mhPDGFRB25-5:
sense,
5'-GGCAAGCUGGUCAAGAUCUGUGACU-3';   (SEQ ID NO. 212)

antisense:
5'-AGUCACAGAUCUUGACCAGCUUGCC-3'   (SEQ ID NO. 213)

mhEGFR-12:
sense,
5'-CCUUCUUAAAGACCAUCCAGGAGGU-3';   (SEQ ID NO. 214)

antisense:
5'-ACCUCCUGGAUGGUCUUUAAGAAGG-3'   (SEQ ID NO. 215)

Many other combinations can be made with other sequences targeting those three genes with different composition and equal or different ratios of the siRNA oligos.

The combinations can also be made with more than three sequences:

VEGFR2-PDGFRab-EGFR cocktail A:

mhVEGFR225-1:
sense,
5'-CCUACGGACCGUUAAGCGGGCCAAU-3';   (SEQ ID NO. 216)

antisense:
5'-AUUGGCCCGCUUAACGGUCCGUAGG-3'   (SEQ ID NO. 217)

mhPDGFRa25-2:
sense,
5'-GAUAAUGACUCACCUGGGGCCACAU-3';   (SEQ ID NO. 218)

antisense:
5'-AUGUGGCCCCAGGUGAGUCAUUAUC-3'   (SEQ ID NO. 219)

mhPDGFRb25-5:
sense,
5'-GGCAAGCUGGUCAAGAUCUGUGACU-3';   (SEQ ID NO. 220)

antisense:
5'-AGUCACAGAUCUUGACCAGCUUGCC-3'   (SEQ ID NO. 221)

mhEGFR-1:
sense,
5'-CUCUGGAUCCCAGAAGGUGAGAAAG-3';   (SEQ ID NO. 222)

antisense:
5'-CUUUCUCACCUUCUGGGAUCCAGAG-3'   (SEQ ID NO. 223)

VEGFR1-VEGFR2-PDGFRb-EGFR-VEGF cocktail A:

mhVEGFR125-6:
sense,
5'-CCAGAAAGUGCAUUCAUCGGGACCU-3';   (SEQ ID NO. 224)

antisense:
5'-AGGUCCCGAUGAAUGCACUUUCUGG-3'   (SEQ ID NO. 225)

mhVEGFR225-1:
sense,
5'-CCUACGGACCGUUAAGCGGGCCAAU-3';   (SEQ ID NO. 226)

antisense:
5'-AUUGGCCCGCUUAACGGUCCGUAGG-3'   (SEQ ID NO. 227)

-continued mhPDGFRB25-10:
sense,
5'-CAUGCCUCCGACGAGAUCUAUGAGA-3';   (SEQ ID NO. 228)

antisense:
5'-UCUCAUAGAUCUCGUCGGAGGCAUG-3'    (SEQ ID NO. 229)

mhEGFR-1:
sense,
5'-CUCUGGAUCCCAGAAGGUGAGAAAG-3';   (SEQ ID NO. 230)

antisense:
5'-CUUUCUCACCUUCUGGGAUCCAGAG-3'    (SEQ ID NO. 231)

mhVEGF25-2:
sense,
5'-GCAGCUUGAGUUAAACGAACGUACU-3';   (SEQ ID NO. 232)

antisense:
5'-AGUACGUUCGUUUAACUCAAGCUGC-3'    (SEQ ID NO. 233)

VEGFR1-VEGFR2-PDGFRb-EGFR-VEGF cocktail C:

mhVEGFR125-6:
sense,
5'-CCAGAAAGUGCAUUCAUCGGGACCU-3';   (SEQ ID NO. 234)

antisense:
5'-AGGUCCCGAUGAAUGCACUUUCUGG-3'    (SEQ ID NO. 235)

mhVEGFR225-1:
sense,
5'-CCUACGGACCGUUAAGCGGGCCAAU-3';   (SEQ ID NO. 236)

antisense:
5'-AUUGGCCCGCUUAACGGUCCGUAGG-3'    (SEQ ID NO. 237)

mhPDGFRa25-2:
sense,
5'-GAUAAUGACUCACCUGGGGCCACAU-3';   (SEQ ID NO. 238)

antisense:
5'-AUGUGGCCCCAGGUGAGUCAUUAUC-3'    (SEQ ID NO. 239)

mhPDGFRB25-5:
sense,
5'-GGCAAGCUGGUCAAGAUCUGUGACU-3';   (SEQ ID NO. 240)

antisense:
5'-AGUCACAGAUCUUGACCAGCUUGCC-3'    (SEQ ID NO. 241)

mhEGFR-12:
sense,
5'-CCUUCUUAAAGACCAUCCAGGAGGU-3';   (SEQ ID NO. 242)

antisense:
5'-ACCUCCUGGAUGGUCUUUAAGAAGG-3'    (SEQ ID NO. 243)

mhVEGF25-2:
sense,
5'-GCAGCUUGAGUUAAACGAACGUACU-3'    (SEQ ID NO. 244)

antisense,
5'-AGUACGUUCGUUUAACUCAAGCUGC-3'    (SEQ ID NO. 245)

B. Combined VEGF Pathway Gene Inhibition

A number of factors were considered during development of the compositions and methods of the present invention for inhibition of NV. First, NV diseases are complex and the result of multiple proteins and abnormally over-expressed disease-causing genes and multiple malfunctions of disease-causing proteins. Second, nucleic acid agents that activate RNA interference (RNAi) are highly selective inhibitors of gene expression in a sequence specific manner. Thirdly, inhibition of NV by modulation of protein activity can be achieved by a number of methods, including an inhibition of protein function (antagonists), stimulation of protein function (agonists), reduction of protein expression levels, and post transcriptional modification of proteins. Treatment of NV disease ideally requires sophisticated therapeutic actions to effectively shut down a particular biological pathway that is critical for disease progression, including simultaneously blocking functions of both ligands and their receptor, simultaneously blocking receptor activity and down stream signaling proteins, and simultaneously blocking redundant elements of a pathway. This is the case for the NV disease and the VEGF pathway.

However, identification of a single agent selective for two or three or more proteins is difficult and oftentimes impractical, if not impossible. To overcome this difficulty, use of a combination of drugs has been something of a trend in modern medicine. In oncology applications, combined chemotherapies have achieved remarkable anti-cancer efficacy. One example is the use of docetaxel, ifosfamide and cisplatin combination therapy for treatment of oropharyngeal cancer with multiple bone metastases from prostate cancer (2). In other therapeutic areas, another example is the treatment of ulcerative colitis with combination of Corticosteroids, Metronidazole and Vancomycin (3). For treatment of insufficiently controlled type 2 diabetes, the efficacy and safety of adding rosiglitazone to a combination of glimepiride and metformin therapy were evaluated (4).

Although those clinical studies have demonstrated remarkable therapeutic efficacies, the toxicities of higher dosage and long time safeties are always major concerns, due to their different sources of origins, different manufacturing processes and different chemistry properties. To overcome these problems, an aspect of the present invention are using s siRNA oligonucleotide gene inhibitors to provide a unique advantage to achieve combination effects with a combination of siRNA to target multiple disease causing genes in the same treatment. One advantage provided by the present invention is a result that all siRNA oligonucleotides are very similar chemically and pharmacologically, and can be from the same source of origin and same manufacturing process. Another advantage provided by the present invention is that multiple siRNA oligonucleotides can be formulated in a single preparation such as a nanoparticle preparation.

Accordingly, an aspect of the present invention is to combine siRNA agents so as to achieve specific and selective inhibition of multiple VEGF pathway genes and as a result achieve a inhibition of NV disease and a better clinical benefit. The present invention provides for many combinations of siRNA targeting including combinations that target VEGF itself together with its receptors including VEGF R1 (Flt1) and VEGF R2 (KDR), parallel growth factors including PDGF and EGF and their receptors, down stream signaling factors including RAF and AKT, and transcription factors including NFKB, and their combination. A preferred embodiment is a combination of siRNA inhibiting VEGF and two of its receptors VEGF R1 (Flt1) and VEGF R2 (KDR). Another preferred embodiment is a combination of siRNA inhibiting VEGF and its receptors, PDGF and its receptors, and EGF and its receptors. Yet another preferred embodiment is a combination of siRNA inhibiting VEGF and its receptors and down stream signaling.

The dsRNA oligonucleotides can be combined for a therapeutic for the treatment of NV disease. In one embodiment of the present invention they can be mixed together as a cocktail and in another embodiment they can be administered sequentially by the same route or by different routes and formulations and in yet another embodiment some can be administered as a cocktail and some administered sequentially. Other combinations of siRNA and methods for their combination will be understood by one skilled in the art to achieve treatment of NV diseases.

C. Combined VEGF Pathway Antagonist and Gene Inhibition

Disease is complicated and often involves multiple pathological processes as well as variations in severity of disease symptoms and, often, variations from one patient to another. Many diseases are caused by abnormal overexpression of disease-causing or disease control genes, or from foreign infectious organisms, or both. Disease progression, the development of reduced response to treatments over time and drug resistance also limit clinical benefit of a single treatment or modality. One means to overcome such limitations is through use of combinations of treatments and drugs.

Therefore, an aspect of the present invention is to combine siRNA agents with other agents so as to achieve a strong, durable, and robust inhibition of NV disease and a superior clinical benefit. The present invention provides multiple combinations of siRNA agents together with other agents, including combinations of therapeutic siRNA for VEGF itself and its receptors with antagonists of VEGF itself and its receptors (such as Avastin). The present invention also provides combinations of therapeutic siRNA agents with orally available kinase inhibitors (such as SU1 1248). The present invention also provides combinations of therapeutic siRNA agents with immunotherapy. Yet another embodiment of the present invention is to combine siRNA with antiproliferative agents. Other combinations of siRNA agents and other agents will be understood by one skilled in the art to achieve treatment of NV diseases.

D. Formulation and Administration

Recent efforts towards developing tissue targetable nucleic acid delivery systems based on synthetic reagents have produced promising results. To be robust, effective delivery systems should have multiple levels of selectivity, i.e. selective localization at the disease tissue and selective inhibition of biochemical pathways driving the pathology. Moreover, the most effective current therapies require "multi-targeted" therapeutics, i.e. designer "dirty" drugs with multiple mechanisms of activity, blocking redundant pathological pathways. A superior approach would be use "smart" nanoparticles that simultaneously target disease and deliver nucleic acid agents into the target cells and into the correct subcellular compartment.

In one embodiment, the present invention provides for formulations for siRNA dsRNA oligonucleotides that comprise tissue-targetable delivery with three additional properties. These properties are nucleic acid binding into a core that can release the siRNA into the cytoplasm, protection from non-specific interactions, and tissue targeting that provides cell uptake. No one material has all of these required properties in one molecule. The invention provides for compositions and methods that use modular conjugates of three materials to combine and assemble the multiple properties required. They can be designed and synthesized to incorporate various properties and then mixed with the siRNA payload to form the nanoparticles. Based on these embodiments, a preferred embodiment comprises a modular polymer conjugate targeting neovasculature by coupling a peptide ligand specific for those cells to one end of a protective polymer, coupled at its other end to a cationic carrier for nucleic acids. This polymer conjugate has three functional domains, sometimes referred to as a tri-functional polymer (TFP). The modular design of this conjugate allows replacement and optimization of each component separately. An alternative approach has been to attach surface coatings onto preformed nanoparticles. Adsorption of a steric polymer coating onto polymers is self-limiting; once a steric layer begins to form it will impede further addition of polymer. The compositions and methods of the invention permit an efficient method for optimization of each of the three functions, largely independent of the other two functions.

Formation of Nucleic Acid Core Particle

Delivery agents for nucleic acids must assist their gaining access to the interior of cells and in a manner such that they can exert their biological activity. Efforts to address this challenge for nucleic acid therapeutics with synthetic materials include use of simple cationic lipid and polymer complexes developed as in vitro DNA transfection reagents. It was quickly found that both getting nucleic acids into cells and obtaining biological activity is extremely difficult. For example, achieving a stable nucleic acid package for transport is possible but not always easy to reconcile with the need to release the nucleic acid into the nucleus, or in the case of siRNA into the cytoplasm. Also, a large number of cationic lipids and polymers that are effective in vitro do not retain activity when administered in vivo, unfortunately for reasons still largely unknown, providing little predictive value for developing complexes active in vivo. Interest in studies with RNA have lagged far behind, until now with the recent eruption of interest in siRNA. Nonetheless, lung tissue can often be transfected from an intravenous administration of DNA complexes. Similar biological activity has been observed when siRNA has been used as the payload.

Recent studies have identified one class of cationic polymers composed of defined polypeptide structures that appear to have broad capabilities. A large number of members of this class can be synthesized with defined structures covering linear and branched forms and have been found to offer biological activity both in vitro and in vivo. They have been shown to have activity with several types of nucleic acids, including plasmids and DNA or RNA oligonucleotides. The success with this class of cationic polymer appears to result from a design incorporating specific structures, including branching, and using a mixture of hard and weak bases to form a polymer with mixed cationic properties. Another advantage of this particular class is its biodegradable nature, being constructed entirely from natural amino acids, albeit non-natural branching. Having a polymer with at least two properties to use for optimization, continuing development of materials for forming effective core complexes with siRNA can be refined and focused on for further improvements to balance stability and cytoplasmic release. Optimized core forming polymers can be used as the basis for the other functions.

Protective Steric Coating

Even liposomes with an external lipid bilayer resembling the outer cellular membrane are rapidly recognized and cleared from blood. Unlike viral particles, though, nanotechnology has access to a broad range of synthetic polymer chemistry. Hydrophilic polymers, such as PEG and polyacetals and polyoxazolines, have proven effective to form a "steric" protective layer on the surface of colloidal drug delivery systems whether liposomes, polymer or electrostatic nanoparticles, reducing immune clearance from blood. The use of this steric PEG layer was first developed and most extensively studied with sterically stabilized liposomes. The present invention provides for alternative approaches, such as chemical reduction of surface charge, in addition to a steric polymer coating.

The evidence is strong that the steric barrier, and biological consequences, derive from physical, not chemical, properties. Several other hydrophilic polymers have been reported as alternatives to PEG. Physical studies on sterically stabilized liposomes have provided a strong mechanistic underpinning for physical behavior of the polymer layer and can be used to achieve similar coatings on other types of particles. However, while physical studies have shown formation of a similar polymer layer on the surface of polymer complexes with nucleic acids, and achievement of similar biological properties, we lack sufficient information today to use of the physical properties to accurately predict the desired biological properties, protection from immune clearance from blood.

Advanced studies are constructing nanoparticle complexes with controlled variations in their physical properties followed by determination of their biological properties. From the many liposome studies, it is clear than physical properties with the greatest impact on biological activity can be obtained by synthesis of a matrix of conjugates varying size of the two polymers and the grafting density. Note that while the surface steric layer function is due to physical properties, the optimal conjugation chemistry still depends on the specific chemical nature of the steric polymer and the carrier to which it is coupled.

Methods for formation of the nanoparticles with the surface steric polymer layer are also a relevant parameter. One embodiment of the present invention provides for methods where the steric polymer is coupled to the carrier polymer to give a conjugate that self-assembles with the nucleic acid forming a nanoparticle with the steric polymer surface layer. Another embodiment is to attach surface coatings onto preformed nanoparticles. In self-assembly formation of the surface steric layer depends on interactions of the carrier polymer with the payload, not on penetration through a forming steric layer to react with particle surface. In this case, effects of the steric polymer on ability of the carrier polymer to bind the nucleic acid payload may have adverse effects on particle formation, and thus the surface steric layer. If this occurs, the grafting density of the steric polymer on the carrier will have exceeded its maximum, or the structural nature of the grafting is not adequate.

Surface Exposed Ligands Targeting Specific Tissues

Ability of the nanoparticle to reach the interior of the target cells, selectively, resides in its ability to induce a specific receptor mediated uptake. This is provided in the present invention by exposed ligands with the binding specificity. While many types of ligands have been studied extensively for targeting colloidal delivery systems, many have relied on antibodies. Over twenty years ago, this idea was developed for coupling antibodies to the surface of liposomes, usually referred to as immunoliposomes. One important parameter that has emerged in the impact of ligand density. The extensive studies achieved good success in vitro but only recently have begun to produce positive results in vivo, now reaching the stage of clinical development for delivery of small molecule drugs.

Antibodies tend to meet many requirements for use as the ligand, including good binding selectivity and nearly routine preparation for nearly any receptor and broad applicability of protein coupling methods regardless of nanoparticle type. Monoclonal antibodies even show signs of utility to cross the blood-brain-barrier. On the other hand, they are not ideal. As targeting ligands, antibodies are very large proteins, about 150 Kd. This makes conjugation to yield a specific orientation difficult unless an extra Cys amino acid residue can be introduced, or other unique site identified, for the chemical coupling. Truncated forms can be used to reduce size but loss of affinity can occur, such as with "scFv" constructions.

Another troubling property of antibodies is their multitude of biological activities, many conveyed in domains not associated with antigen binding, which are part of their role in the mammalian immune system. These immune activities can be exploited but they also can interfere in the nanoparticle steric layer role of avoiding immune clearance. Other proteins that are natural ligands also have been considered for targeting nanoparticles, such as transferrin for transferrin receptor and Factor VII and Factor VIIa proteins and their fragments. These agents can be good candidates but their successful use requires considerable effort to identify specific coupling chemistry, coupling without loss of binding activity, and exposure on the particle without reintroducing immune clearance.

A preferred class of ligands are small molecular weight compounds with strong selective binding affinity for internalizing receptors. Studies have been evaluated natural metabolites such as vitamins like folate and thiamine, polysaccharides like wheat germ agglutinin or sialyl Lewis$^x$ for e-selectin, and peptide binding domains like RGD for integrins. Peptides offer a versatile class of ligand, since phage display libraries can be used to screen for natural or unnatural sequences, even with in vivo panning methods. Such phage display methods can permit retention of an unpaired Cys residue at one end for ease of coupling regardless of sequence. The recent in vivo success using an RGD peptide for targeted delivery of nanoparticles to neovasculature indicates this approach can be very effective to meet the major requirements for effective ligands: specific chemistry that doesn't interfere in ligand binding or induce immune clearance yet enables selective receptor mediated uptake at the target cells.

A preferred embodiment of the invention comprises an RGD-2C peptide ligand conjugate. The RGD-2C ligand provides localization at neovasculature as well as tumor cells nearby tumor neovasculature, intracellular internalization of the nucleic acid containing nanoparticles, and release of the nucleic acid giving effective biological activity of the nucleic acid.

Another preferred embodiment of the invention comprises mixtures of ligand-conjugates of two or more ligands, or conjugates of two or more ligands. A preferred embodiment of the invention comprises mixtures of RGD peptide ligands with Factor VII proteins or their peptide fragments or chemical analogues. Another preferred embodiment of the invention comprises mixtures of RGD peptide ligands with ligands binding e-selectins. Another preferred embodiment of the invention comprises mixtures of RGD peptide ligands with apoE proteins or their peptide fragments or chemical analogues. Another preferred embodiment of the invention comprises mixtures of RGD peptide ligands with tumor cell binding ligands such as folate, transferrin, porphyrin, bFGF, and EGF. Another preferred embodiment of the invention comprises mixtures of three or more of these ligands. A preferred embodiment of the invention comprises a conjugate of two or more ligands at one domain of a carrier and a polyamine agent at a second domain of said carrier.

Another preferred embodiment of the invention comprises mixtures of ligand conjugates. The mixture of ligand conjugates can comprise the ligands conjugated to the same carrier agent and optionally to the same domain of the carrier or the mixture of ligand conjugates can comprise the ligands conjugated to different carrier agents or optionally to different domains of carrier agents. The mixture of ligand conjugates can be further comprised of protective, fusogenic, or carrier agents, such as PEG or polyacetals or pH-sensitive polymers or polyamines or histidine-lysine copolymers.

The compositions and methods of the present invention provide for administration of RNAi comprising polymers, polymer conjugates, lipids, micelles, self-assembly colloids, nanoparticles, sterically stabilized nanoparticles, or ligand-directed nanoparticles. Targeted synthetic vectors of the type described in WO01/49324, which is hereby incorporated by reference in its entirety, may be used for systemic delivery of nucleic acids of the present invention inducing RNAi. In one embodiment, a PEI-PEG-RGD (polyethyleneimine-polyethylene glycol-argine-glycine-aspartic acid) synthetic vector can be prepared and used, for example as in Examples 53 and 56 of WO01/49324. This vector was used to deliver RNAi systemically via intravenous injection. The skilled artisan will recognize that other targeted synthetic vector molecules known in the art may be used. For example, the vector may have an inner shell made up of a core complex comprising the RNAi and at least one complex forming reagent.

Figure 25:
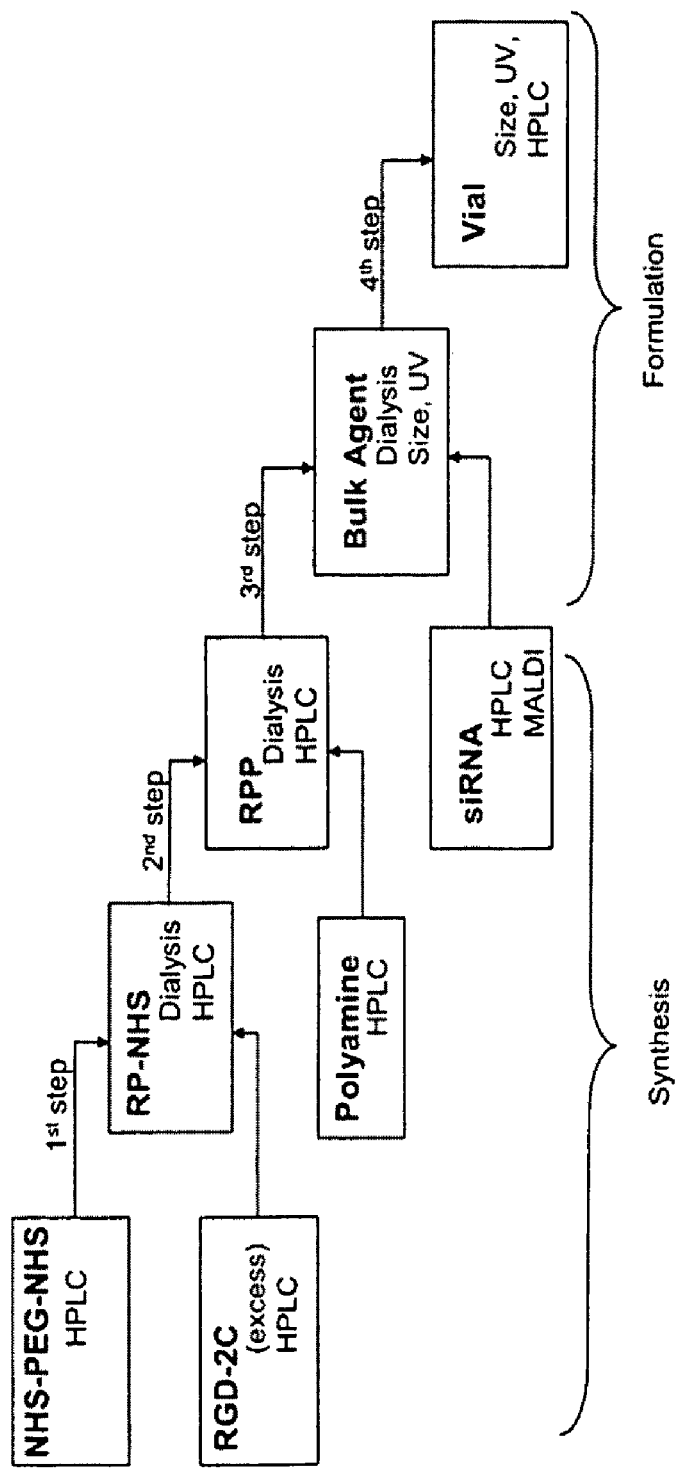
FIG. 25. Manufacturing flow chart for production of an RGD-polymer conjugate and a nanoparticle-siRNA preparation starting from raw materials of a homobifunctional activated PEG, an RGD-2C peptide, a polyamine containing agent, and a mixture of dsRNA.
Figure 26:
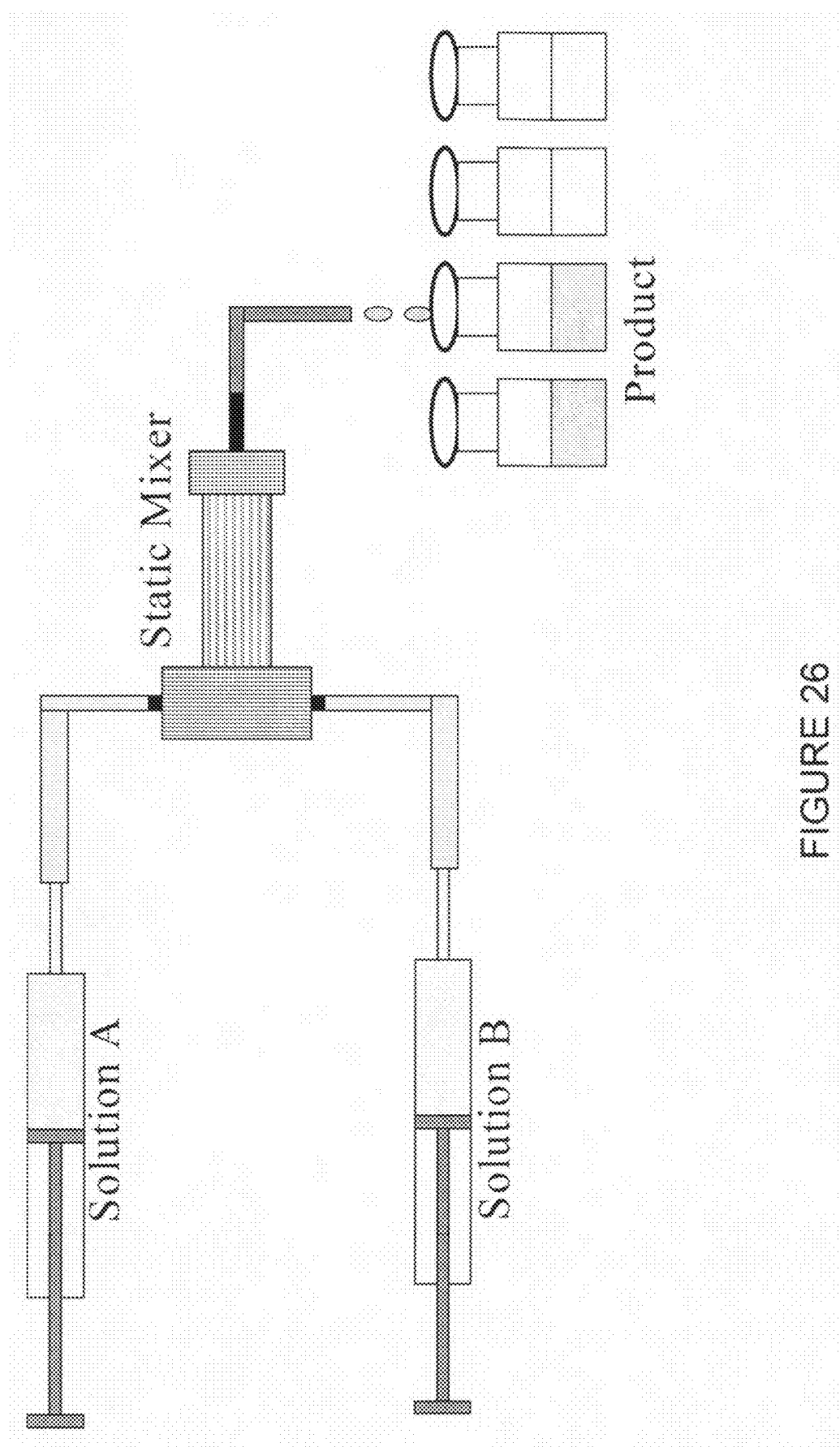
FIG. 26. The use of a static mixer to manufacture a nanoparticle-siRNA preparation starting from two solutions, a polymer solution comprising polymer conjugates and an siRNA solution comprising three dsRNA agents.

The vector also may contain a fusogenic moiety, which may comprise a shell that is anchored to the core complex, or may be incorporated directly into the core complex. The vector may further have an outer shell moiety that stabilizes the vector and reduces nonspecific binding to proteins and cells. The outer shell moiety may comprise a hydrophilic polymer, and/or may be anchored to the fusogenic moiety. The outer shell moiety may be anchored to the core complex. The vector may contain a targeting moiety that enhances binding of the vector to a target tissue and cell population. Suitable targeting moieties are known in the art and are described in detail in WO01/49324.

a. Preparation of RGD-Targeted Nanoparticles Containing VEGF Pathway siRNA:

One embodiment of the present invention provides compositions and methods for RGD-mediated ligand-directed nanoparticle preparations of anti-VEGF pathway siRNA short dsRNA molecules. FIGS. 25 and 26 show a method for the manufacture of RGD-2C-mediated tissue targeted nanoparticle containing siRNA. The targeting ligand, RGD containing peptide (ACRGDMFGCA) (SEQ ID NO: 246) is conjugated to a steric polymer such as polyethylene glycol, or other polymers with similar properties. This ligand-steric polymer conjugate is further conjugated to a polycation such as polyethyleneimine or other effective material such as a histidine-lysine copolymer. The conjugates can be covalent or non-covalent bonds and the covalent bonds can be non-cleavable or they can be cleavable such as by hydrolysis or by reducing agents. The conjugates can be prepared with heterobifunctional polymers, such as an NHS-PEG-VS commercially available reagent (Nektar) or hetero-bifunctional agents prepared for manufacturing, or with homo-bifunctional polymers, such as NHS-PEG-NHS commercially available reagent (Rapp Polymere) or homo-bifunctional agents prepared for manufacturing. One preferred embodiment of the present invention comprises use of a homo-bifunctional NHS-PEG-NHS agent, such as a reagent commercially available from RAPP Polymere, first to couple with an RGD-2C peptide prepared by solid phase synthesis and send to couple with a polyamine containing polymer such as PEI commercially available or a histidine-lysine copolymer prepared by solid phase synthesis.

Another preferred embodiment of the present invention comprises a first combination of an RGD-PEG-polyamine conjugate with a polyamine polymer, such as PEI or a histidine-lysine copolymer, and a second combination of the said polymer mixture with a second mixture of dsRNA oligonucleotides. A solution comprising the polymer conjugate, or comprising a mixture of a polymer conjugate with other polymer, lipid, or micelle such as materials comprising a ligand or a steric polymer or fusogen, is mixed with a solution comprising the nucleic acid, in one embodiment an siRNA targeted against specific genes of interest, in desirable ratios to obtain nanoparticles that contain siRNA.

In this embodiment, nanoparticles are formed by layered nanoparticle self-assembly comprising mixing the polymer conjugate and the nucleic acid. Non-covalent electrostatic interactions between the negatively charged nucleic acid and the positively charged segment of the polymer conjugate drive the self-assembly process that leads to formation of nanoparticles. This process involves simple mixing of two solutions where one of the solutions containing the nucleic acid is added to another solution containing the polymer conjugate followed by or concurrent stirring. In one embodiment, the ratio between the positively charged components and the negatively charged components in the mixture is determined by appropriately adjusting the concentrations of each solution or by adjusting the volume of solution added. In another embodiment, the two solutions are mixed under continuous flow conditions using mixing apparatus such as static mixer (FIG. 26). In this embodiment, two or more solutions are introduced into a static mixer at rates and pressures giving a ratio of the solutions, where the streams of solutions get mixed within the static mixer. Arrangements are possible for mixers to be arranged in parallel or in series.

E. Combined Formulation and Electric Field

For certain applications, RNAi may be administered with or without application of an electric field. This can be used, for example, to deliver the RNAi molecules of the invention via direct injections into, for example, tumor tissue and directly into or nearby an angiogenic tissue or a tissue with neovasculature. The siRNA may be in a suitable pharmaceutical carrier such as, for example, a saline solution or a buffered saline solution. The present invention, thus generally described, will be understood more readily by reference to the following examples, which are provided by way of illustration and are not intended to be limiting of the present invention.

EXAMPLES

Example 1

Tumor Growth Inhibition with Combination Use of siRNA Duplexes Targeting VEGFR2 and Bevacizumab (Avastin) Against VEGF Material and Methods.

Reagents: Avastin, monoclonal antibody against VEGF (25 mg/ml, Genetech); siRNA against mouse VEGFR2, sequence ((a) AAGCTCAGCACACAGAAAGAC (SEQ ID NO: 247); (b) AATGCGGCGGTGGTGACAGTA) (SEQ ID NO: 248); siRNA against luciferase (Qiagen); Avertin made of 1.5 gram 2,2,2,Tribromoethanol and 1.5 ml t-amyl alcohol (Cat# T4840-2, Cat# 24048-6, Aldrich) in 100 ml distill water, St. Louis, Mo.]. Mice: athymus female nude mice, 5 to 6 weeks old, were purchased from TACONIC and housed conventionally. All investigations followed guidelines of the Committee on the Care of Laboratory Animals Resources, Commission of Life Sciences, National Research Council. The animal facility of Biomedical Research Institute in Rockville Md. is fully accredited by the American Association of Laboratory Animal Care. Cells: Colon carcinoma cell line, DLD-1 (CCL-221, ATCC) was grown in RPMI 1640 medium with 2 mM L-glutamine, 1.5 g/L sodium bicarbonate, 4.5 g/L glucose, 10 mM HEPES, and 1.0 mM sodium pyruvate, 10% fetal bovine serum.

Procedure: 1) DLD-1 cells near confluence were harvested and resuspended in serum-free RPMI medium. 2) Mice were anaesthetized with Avertin, 0.4 ml/mouse i.p. 3) 100 million cells in 0.1 ml serum-free RPMI medium were injected into mice back s.c. on the left flank for establishment of xenograft tumor model. 4) 5 days after inoculation of tumor cells, sizes of growing tumors were measured with a caliper. Mice were then randomly grouped into 6 groups, 8 mice per group. 5) Experiment design and dosing scheme were as following. 6) SiRNA was delivered through tail-vein injection after been formed a complex with RPP.

ment alone, and in combination with Avastin, did not show any significant (detectable) upregulation or induction of IFN activity (FIG. 4), indicating that the inhibition of NV and inhibition of tumor growth was not due to a non-specific interferon-mediated effect.

Summary

This example illustrates the present invention as it provides compositions and methods for treatment of cancer with small interfering dsRNA oligonucleotide gene inhibitors in combination with monoclonal antibodies (mAb) in the same therapeutic regimen, where the agents inhibit both expression of disease-causing genes and biological functions of disease-causing proteins, resulting in enhanced therapeutic efficacy. In addition, the example provides illustration of simulta-

TABLE I

Regimen of anti-angiogenesis siRNA/mAb treatment of DLD-1 tumor model

| Group | Day-5 | Day-6 | Day-8 | Day-9 | Day-11 | Day-12 | Day-14 | Day |
|---|---|---|---|---|---|---|---|---|
| G1 - Luc-siRNA | | siRNA | | siRNA | | siRNA | siRJ | |
| G2 - Avastin | Avastin | | Avastin | | Avastin | | Avastin | |
| G3 - VEGFR2-siRNA | | siRNA | | siRNA | | siRNA | | siRJ |
| G4 - Mouse-IgG + VEGFR2 | Mouse-IgG | siRNA | Mouse-IgG | siRNA | Mouse-IgG | siRNA | Mouse-IgG | siRJ |
| G5 - Avastin + Luc-siRNA | Avastin | siRNA | Avastin | siRNA | Avastin | siRNA | Avastin | siRJ |
| G6-Avastin + VEGFR2-siRNA | Avastin | siRNA | Avastin | siRNA | Avastin | siRNA | Avastin | siRJ |

Results and Discussion

1. RGD ligand-directed nanoparticle carrying VEGF R2 specific siRNA dsRNA itself was able to achieve tumor growth inhibition after repeated systemic intravenous administrations (FIG. 1) with only 2 mg/kg siRNA.
2. This siRNA-based antiangiogenesis activity (Targeting VEGF R2) was able to enhance the VEGF monoclonal antibody (mAb)-mediated antiangiogenesis, resulting further tumor growth inhibition (FIG. 1).
3. Although many biochemical pathways may be critical independently or collectively for malignant neoplasia, it is widely acknowledged that neo-angiogenesis is critical for growth of many types of cancers. Therefore neo-angiogenesis process has naturally become one of the most targeted areas for tumor drug development. Among many factors involved in neo-angiogenesis VEGF is believed an important controlling factor and one that can enable a therapeutic effect giving clinical benefit as achieved by Avastin, a monoclonal antibody against VEGF and demonstrated to inhibit growth of colon cancer. The combination of NV targeted VEGF siRNA gene inhibition shows evidence of being additive with an antagonist therapeutic when administrated in a combination protocol.
4. The example shows the great benefit of using gene inhibitors and with antagonists such as mAb inhibitors in the same treatment regimen to improve the therapeutic outcome.
5. RT-PCR results directly demonstrated that the VEGFR2 mRNA level in the tumor samples treated with the nanoparticle delivered VEGFR2 specific siRNA has dramatically down regulated, comparing to the expression levels in the untreated tumors (FIG. 2).
6. Immunohistologicalchemistry (IHC analysis) indicated that the protein level knockdown has occurred for VEGFR2 and CD31 which is a marker for neo vasculature (FIG. 3).
7. The ELISA measurement for IFN-alpha activity in the blood samples from nanoparticle/VEGFR2 siRNA treatment alone, and in combination with Avastin, did not show any significant (detectable) upregulation or induction of IFN activity (FIG. 4), indicating that the inhibition of NV and inhibition of tumor growth was not due to a non-specific interferon-mediated effect.

neously blocking both the ligand (e.g. VEGF) and its receptor (e.g. VEGF R2) to provide effective inhibition of a particular biological pathway (e.g. angiogenesis pathway) thereby providing a treatment inhibiting disease progression. Therefore, combined applications of inhibitory activities contributed by two potent and targeted biological inhibitors, RNAi and mAb, is a means for effective treatment of NV diseases including cancer.

Example 2 siRNA-Mediated VEGF Silencing In Vitro and In Vivo

Figure 2:
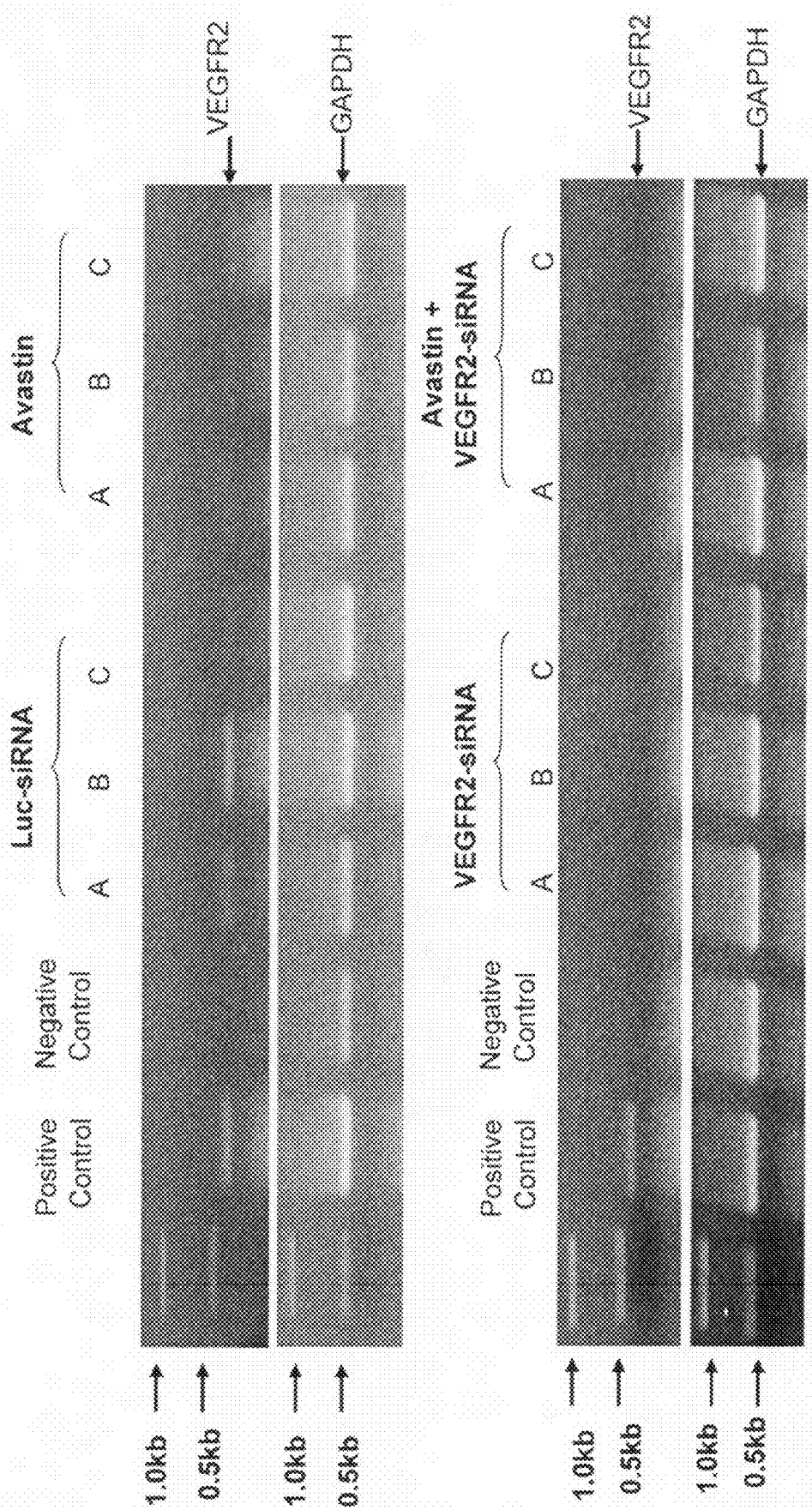
FIG. 2. VEGFR2-siRNA nanoparticle targeting neovasculature through systemic delivery demonstrated potent efficacy in colon carcinoma xenograft mouse model (DLD-1 tumor) after four repeated administrations every three days. RT-PCR results illustrate the knockdown of VEGFR2 gene expression at mRNA level.
Figure 3:
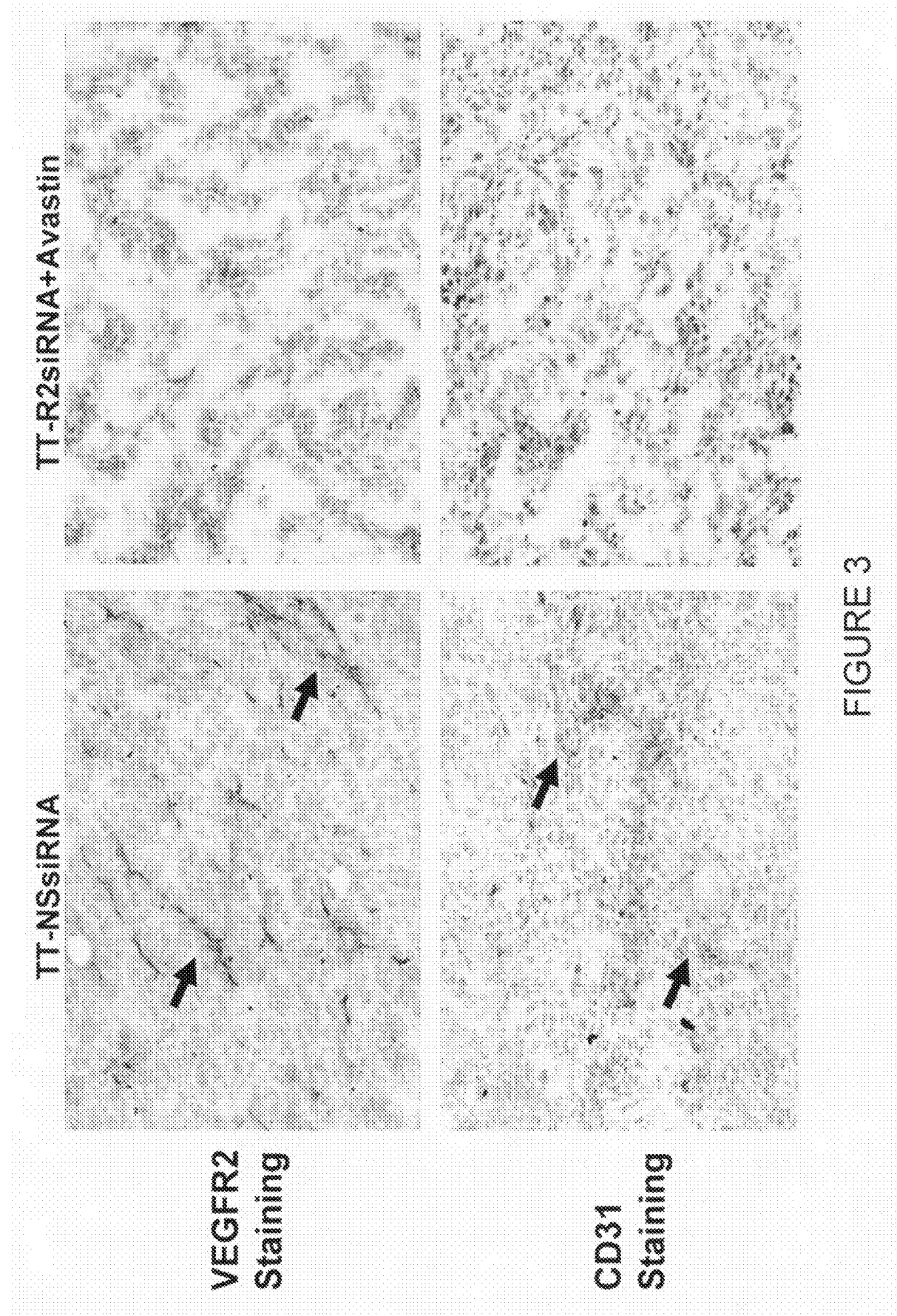
FIG. 3. Human VEGFR2-siRNA nanoparticle targeting neovasculature through systemic delivery demonstrated potent efficacy in colon carcinoma xenograft mouse model (DLD-1 tumor) after four repeated administrations every three days. Immunohistochemistry images show down regulation of VEGFR2 and CD31 expression in the tumor tissue.

Human VEGF 165 specific siRNA was transfected into the MCF-7/VEGF165 cell (hVEGF over-expression) by Lipofectamine resulting in knockdown of hVEGF mRNA in the cell (FIG. 2 upper panel). Using an electroporation procedure, MCF-7/VEGF165 cells were transfected by hVEGF165 specific siRNA, resulting in down regulation of hVEGF expression as determined with an ELISA analysis.

When the hVEGF165 specific siRNA were delivered through intratumoral administration repeatedly, the growth of MCF-7/VEGF165 cell induced xenograft tumors were significantly inhibited. This inhibition was further validated when the tumor tissues were collected for testing hVEGF mRNA expression which resulted in significant down regulation based on RT-PCR analysis. Using the same hVEGF165 specific siRNA, we are also able to demonstrate tumor growth inhibition with head and neck squamous cell carcinoma (HNSCC, 1483 cell) xenograft model, through 5 repeated administrations intratumorally with seven day interval. Each injection requires 10 μg of the specific siRNA in 15 to 30 μL of RNAse free aqueous solution.

Example 3

25 Basepair Blunted Double-Stranded siRNA is More Potent than Regular 19 Basepair siRNA with 3'-Overhangs in Silencing Target Gene Expression In one of in vitro siRNA transfection studies, the MCF/165 breast cancer cells overexpressing human VEGF (hVEGF) were transfected with either 25 basepair blunted double-stranded siRNA (hVEGF-25-siRNA-a, hVEGF-25-siRNA-b, hVEGF-25-siRNA-c, Luc-25-siRNA) or 19 basepair siRNA with 3' overhangs (hVEGF-siRNA-a, GFP-siRNA-a) using an electroporation mediated transfection method. $4 \times 10^6$ MCF7/165 cells were resuspended in 200 µl of siPORT siRNA Electroporation Buffer (Ambion) mixed with 5 µg siRNA and then subjected to electroporation treatment using an Electro Square Porator ECM830 (BTX, Fisher Scientific). The parameters for the electroporation are: voltage 500 v; duration of pulse 60 µs; pulse number 2; pulse interval 1 second. The transfected cells were seeded to 24-well plate at a density of $5 \times 10^4$ cell/well and cultured at 37° C. incubator with 5% $CO_2$. At 24 hours post transfection, the culture media from each well were harvested and the concentration of human VEGF protein in the media was measured using a commercial hVEGF ELISA kit (R&D Systems).

Figure 7:
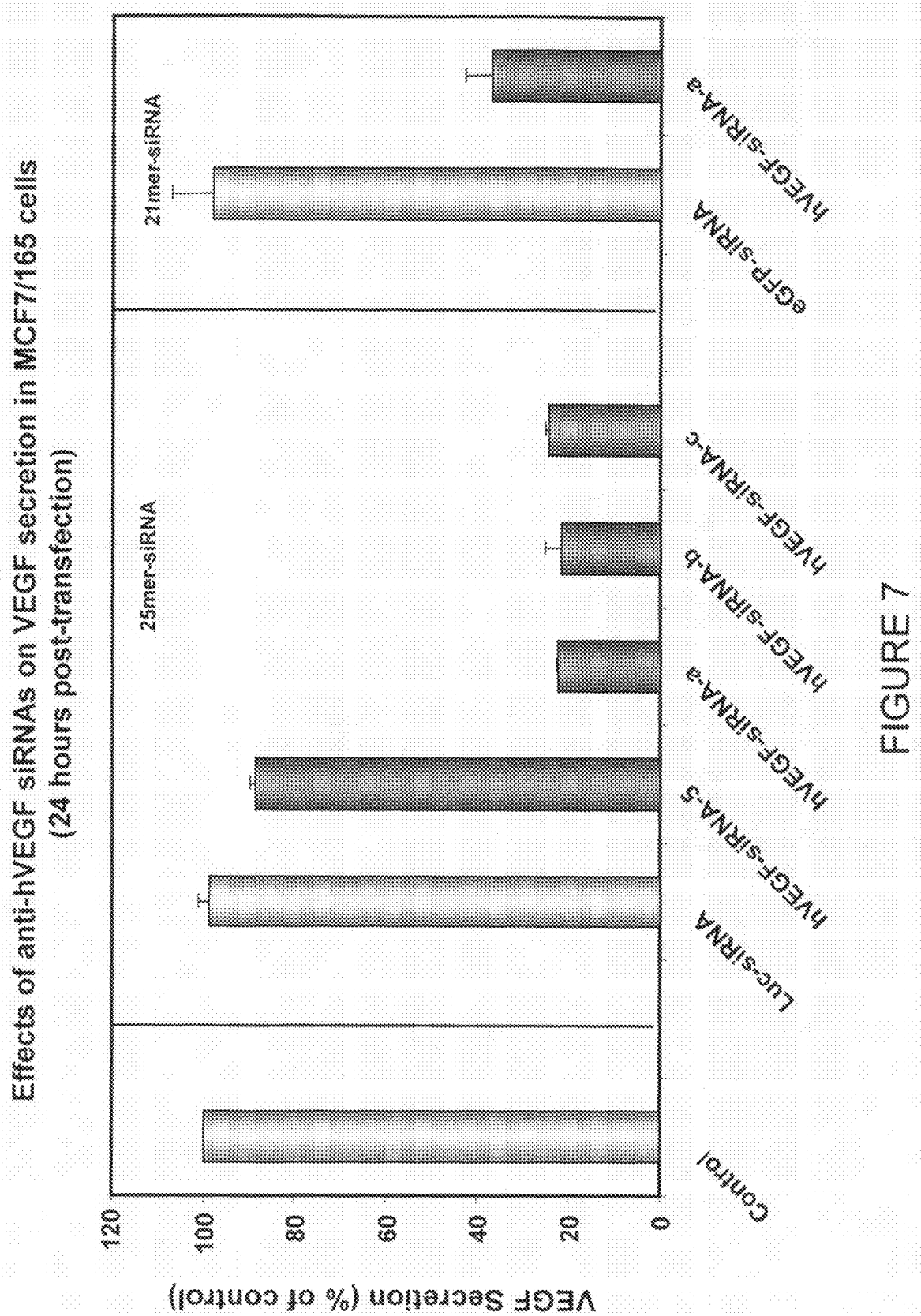
FIG. 7. Human VEGF-siRNA (25 basepair blunt end) is more effective for silencing hVEGF expression in vitro and stronger than the 19 base pair siRNA.

We observed a significant stronger hVEGF target gene inhibition in 25 basepair hVEGF-siRNA treated cells than that in regular 19 basepair hVEGF siRNA treated cells. There was a more than 75% reduction of the secreted hVEGF protein in the culture media of cells transfected with 25 basepair blunted double-stranded hVEGF-25-siRNA molecules at 24 hours post siRNA transfection, compared to an about 60% hVEGF protein reduction observed in cells transfected with regular 19 basepair hVEGF-siRNA-a. Both non-specific sequence control 25 basepair blunted double-stranded siRNA (Luc-25-siRNA) or regular GFP-siRNA with 3'-overhangs did not affect VEGF expression under the same siRNA transfection condition (FIG. 7).

Example 4

25 Basepair Blunted Double-Stranded siRNA Mediated an Elongated Target Gene Silencing In another one of in vitro siRNA transfection studies, the MCF/165 breast cancer cells overexpressing human VEGF (hVEGF) were transfected with either 25 basepair blunted double-stranded siRNA (hVEGF-25-siRNA-a, hVEGF-25-siRNA-b, hVEGF-25-siRNA-c, Luc-25-siRNA) or 19 basepair siRNA with 3' overhangs (hVEGF-siRNA-a, GFP-siRNA-a) using an electroporation mediated transfection method. $4 \times 10^6$ MCF7/165 cells were resuspended in 200 µl of siPORT siRNA Electroporation Buffer (Ambion) mixed with 2 µg or 5 µg siRNA and then subjected to electroporation treatment using an Electro Square Porator ECM830 (BTX, Fisher Scientific). The parameters for the electroporation are: voltage 500 v; duration of pulse 60 µs; pulse number 2; pulse interval 1 second. The transfected cells were seeded to 24-well plate at a density of $5 \times 10^4$ cell/well and cultured at 37° C. incubator with 5% $CO_2$. At 24, 48, 72, 96, and 120 hours post transfection, the culture media from each well were harvested and replaced with fresh culture media. The concentration of human VEGF protein in the media harvested at various time points was measured using a commercial hVEGF ELISA kit (R&D). The siRNA mediated hVEGF knockdown was normalized with the hVEGF protein levels measured in cells treated with respective non-specific control siRNA.

Figure 8:
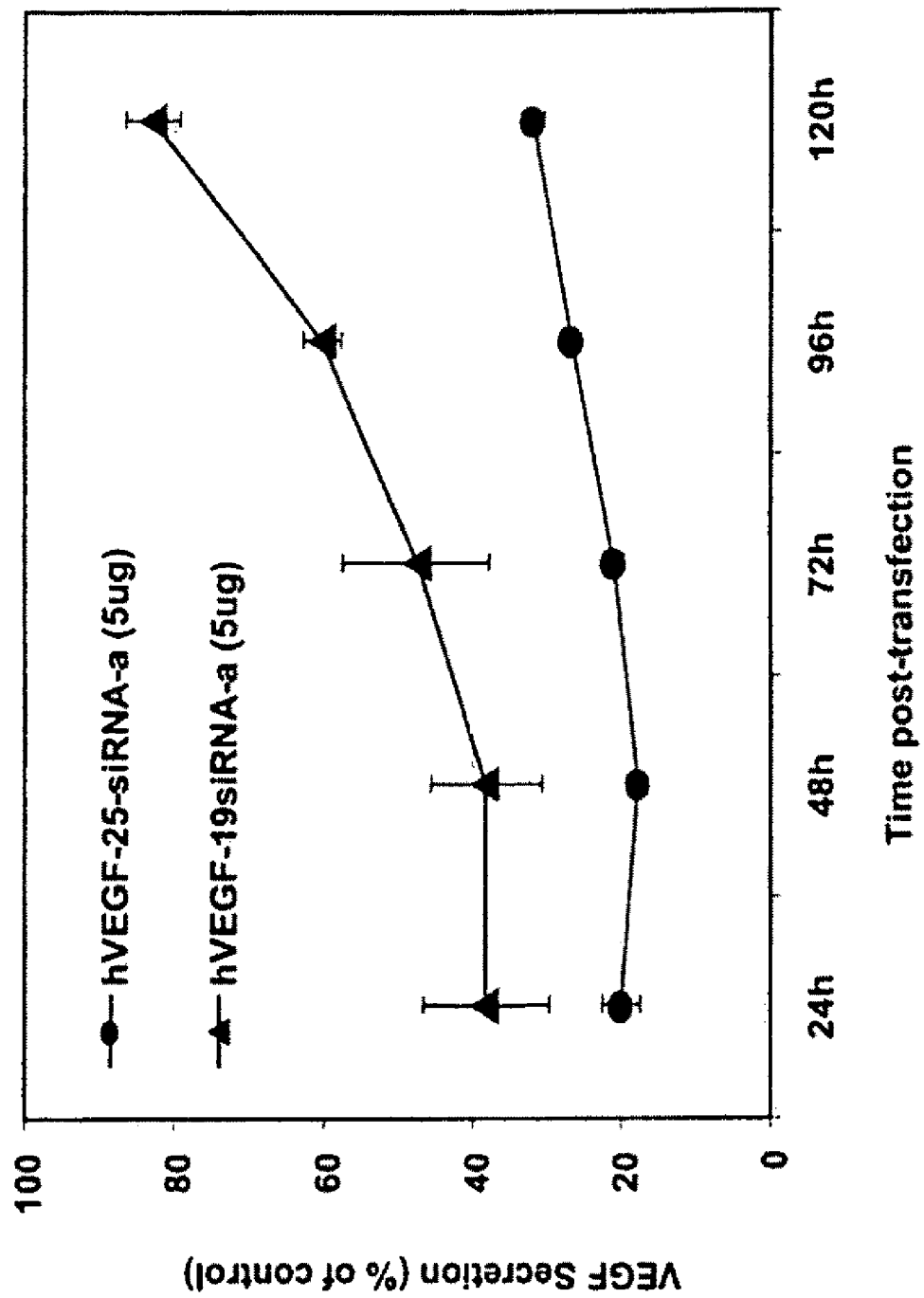
FIG. 8. Human VEGF-siRNA (25 basepair blunt end) is effective for silencing hVEGF expression in vitro and has longer duration than that of the 19 basepair siRNA.

We observed a significant stronger and elongated hVEGF target gene inhibition in 25 basepair hVEGF-siRNA treated cells than that in regular 19 basepair hVEGF siRNA treated cells at every time points tested. At 120 hours post siRNA treatment, there was still a more than 60% reduction of the secreted hVEGF protein in the culture media of cells transfected with 5 µg of 25 basepair blunted double-stranded hVEGF-25-siRNA molecules, compared to an less than 20% hVEGF protein reduction observed in cells transfected with 5 µg of regular 19 basepair hVEGF-siRNA-a (FIGS. 8 and 27). We also observed a dose-dependent siRNA mediated hVEGF gene inhibition for the 25 basepair blunted double-stranded hVEGF-25-siRNA molecules.

Base on our observation, the 25 basepair blunted double-stranded h VEGF-25-siRNA molecules not only gives a stronger target VEGF gene inhibition, but also results in a significant longer duration of effective target VEGF gene inhibition. For example, compared to only 48 hours of more than 60% hVEGF protein reduction achieved using 5 µg of regular 19 basepair hVEGF siRNA, at least 120 hours of more 60% reduction of protein was achieved using 25 basepair blunted double-stranded hVEGF siRNA. Therefore, the 25 basepair blunted double-stranded siRNA are more potent target gene inhibitor that can lead to more significant therapeutic efficacy.

Additional information include (1) Luc-25-siRNA has the sequence of (sense strand 5'-rGGAACCGCUGGAGAG-CAACUGCAUA-3' (SEQ ID NO: 249) and antisense strand 5'-rCCUUGGCGACCUCUCGUUGACGUAU-3') (SEQ ID NO: 250); (2) hVEGF-siRNA-a has the sequence of (sense strand, 5'-rUCGAGACCCUGGUGGACAUdTT-3' (SEQ ID NO: 251) and antisense strand, 5'-rAUGUCCACCAGGGU-CUCGAdTT-3') (SEQ ID NO: 252); (3) GFP-siRNA has the sequence of (sense strand, 5'-rGCUGACCCUGAAGUU-CAUCdTT-3' (SEQ ID NO: 253) and (antisense strand, 5'-rGAUGAACUUCAGGGUCAGCdTT-3') (SEQ ID NO: 254); (4) hVEGFR2-25-siRNA-c: 5'-r(CCAAGUGA-UUGAAGCAGAUGCCUUU)-3' (SEQ ID NO: 255).

Example 5

Figure 9:
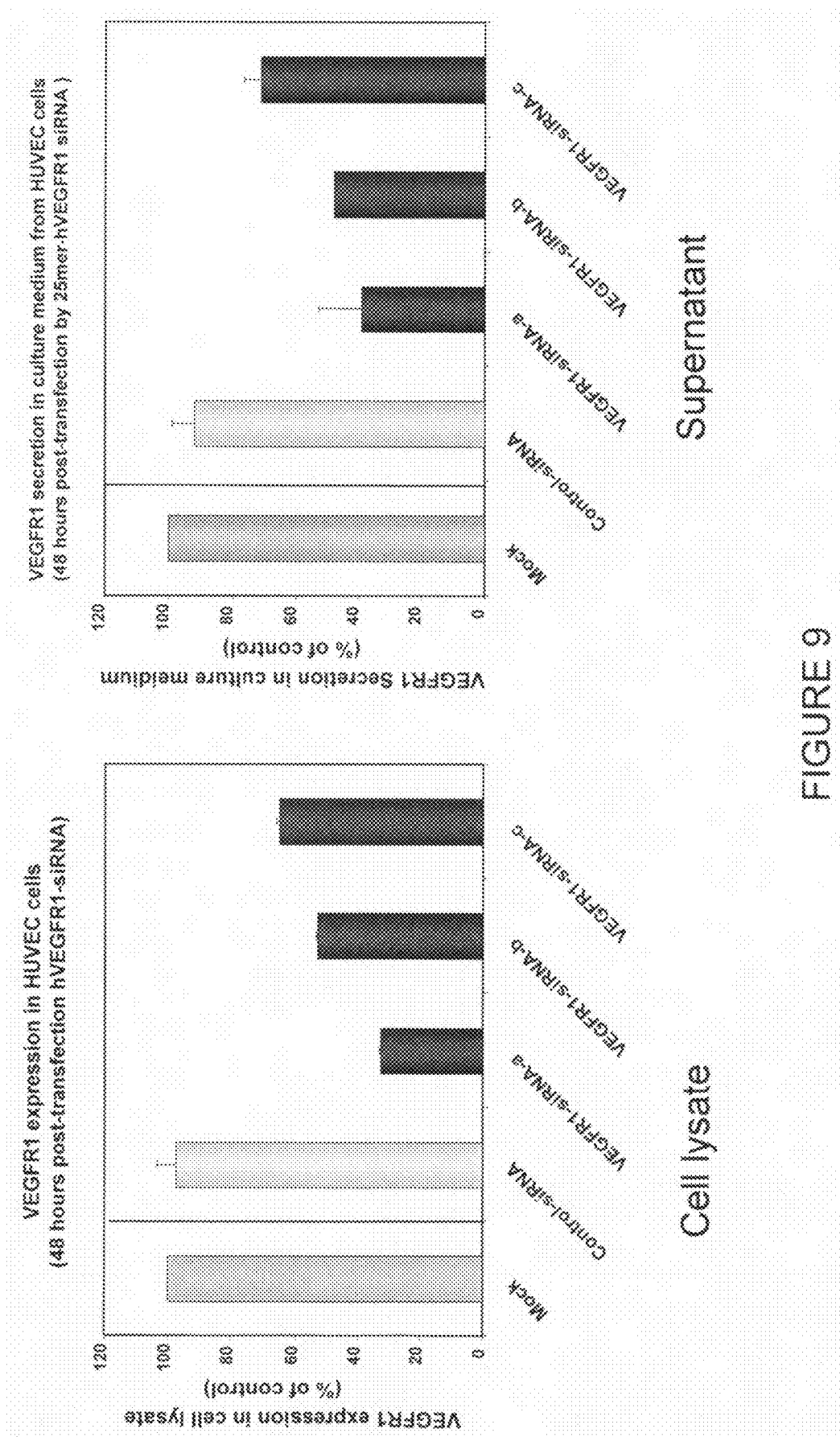
FIG. 9. Human VEGFR1-siRNA (25 base pair blunt end) is effective for silencing hVEGFR1 expression in vitro after 48 hr.
Figure 10:
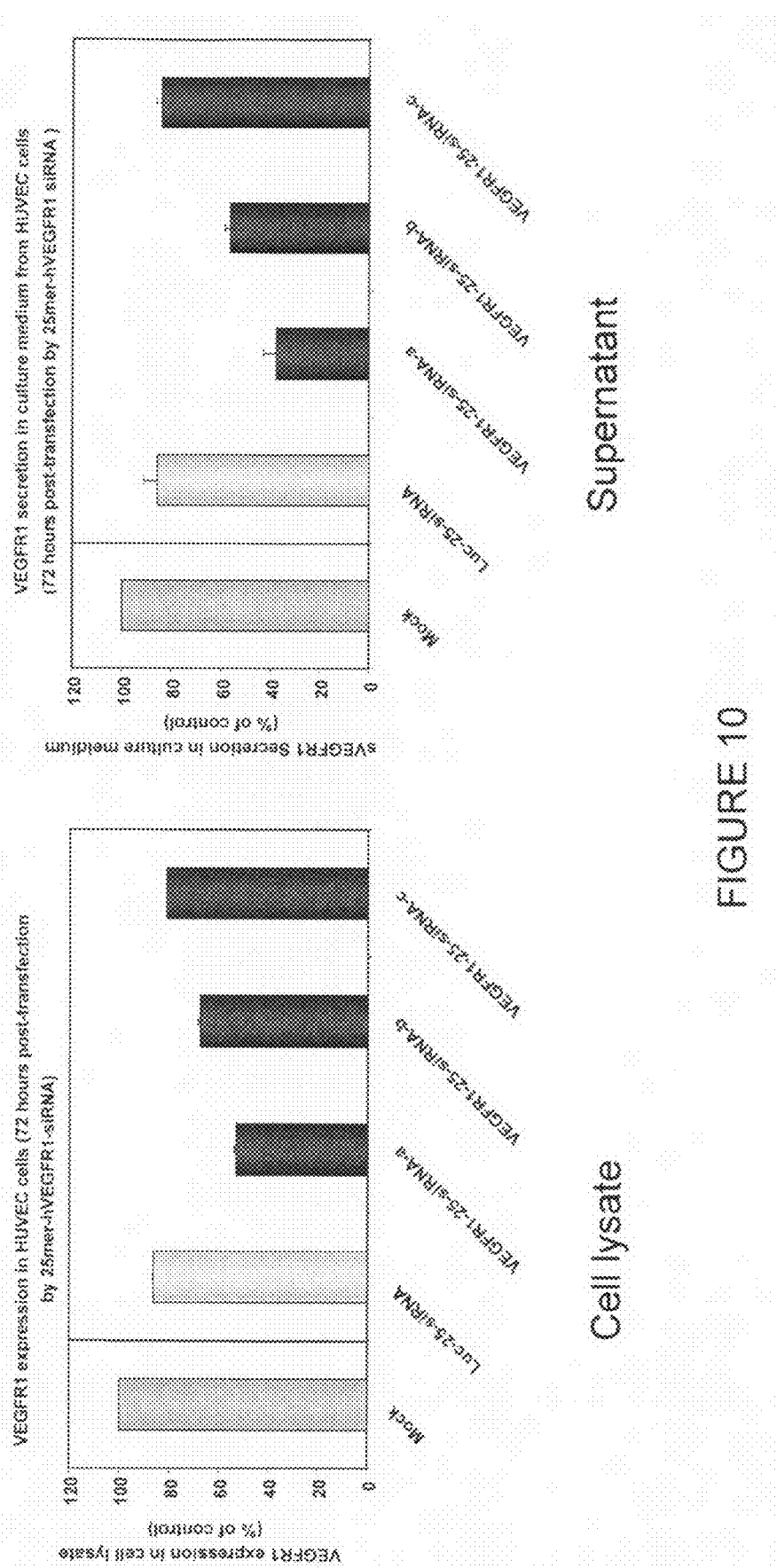
FIG. 10. Human VEGFR1-siRNA (25 base pair blunt end) is effective for silencing hVEGFR1 expression in vitro after 72 hr.
Figure 11:
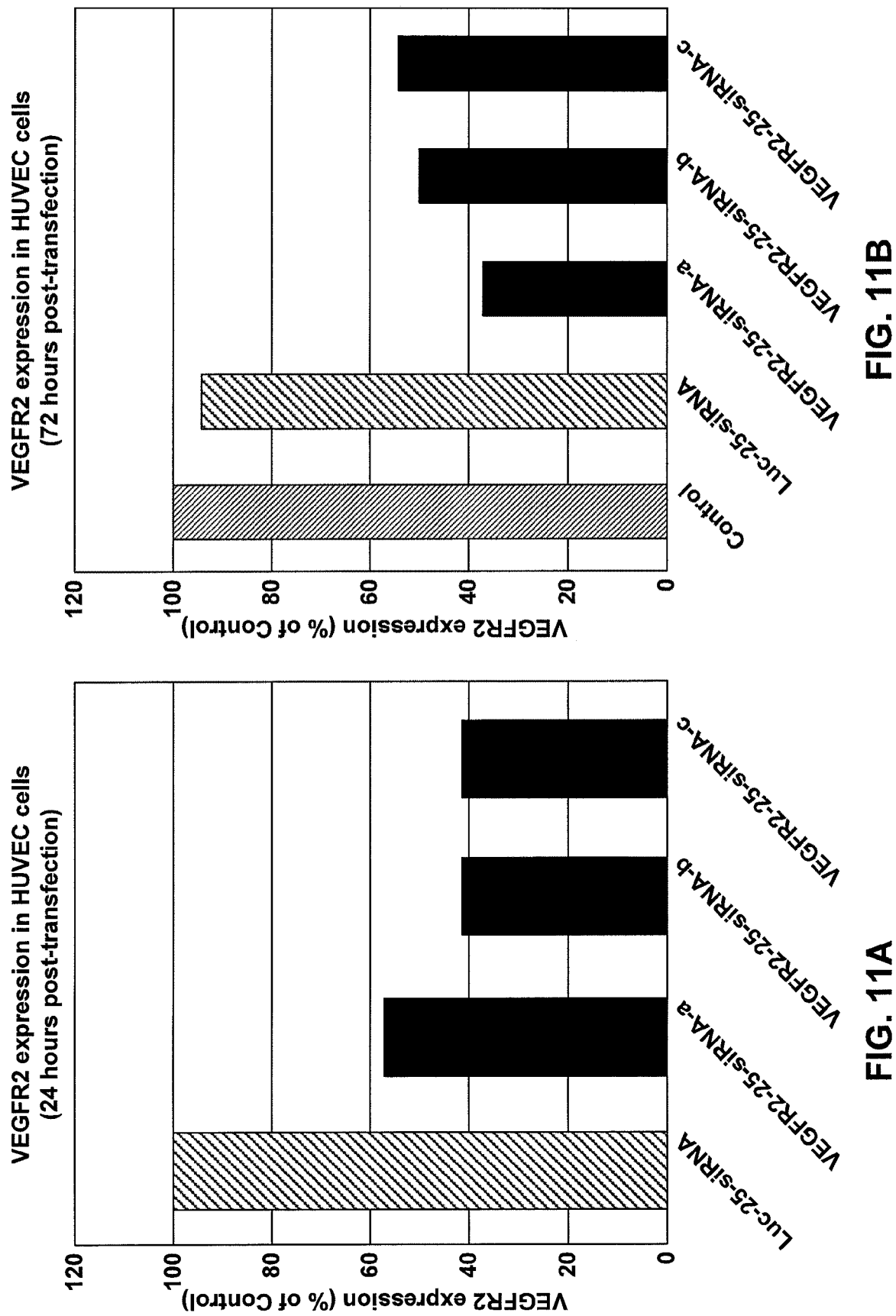
FIG. 11. Human VEGFR2-siRNA (25 base pair blunt end) is effective for silencing hVEGFR2 expression in vitro at two different time points.

25 Base Pair Blunted Double-Stranded siRNA Efficiently Knockdown Human VEGFR1 and VEGFR2 Expression In Vitro Three 25 base pair blunted double-stranded siRNA specifically targeting human VEGFR1 were transfected in HUVEC cells through electroporation. The membrane bound VEGFR1 and free extra cellular fragment of VEGFR1 were measured 96 hours post transfection, through ELISA assay. The VEGFR1-siRNA duplex a demonstrated the strongest VEGFR1 silencing activity, compared to two other siRNA, for both cell lysate protein and the free fragments in the cell culture supernatant solution (FIGS. 9 and 10). When using the same approach to evaluate three 25 base pair blunted double-stranded siRNA targeting human VEGFR2 gene, we found all three duplexes exhibiting potent silencing activity at both 24 hours and 72 hours post transfection time points (FIG. 11).

Example 6

Figure 12:
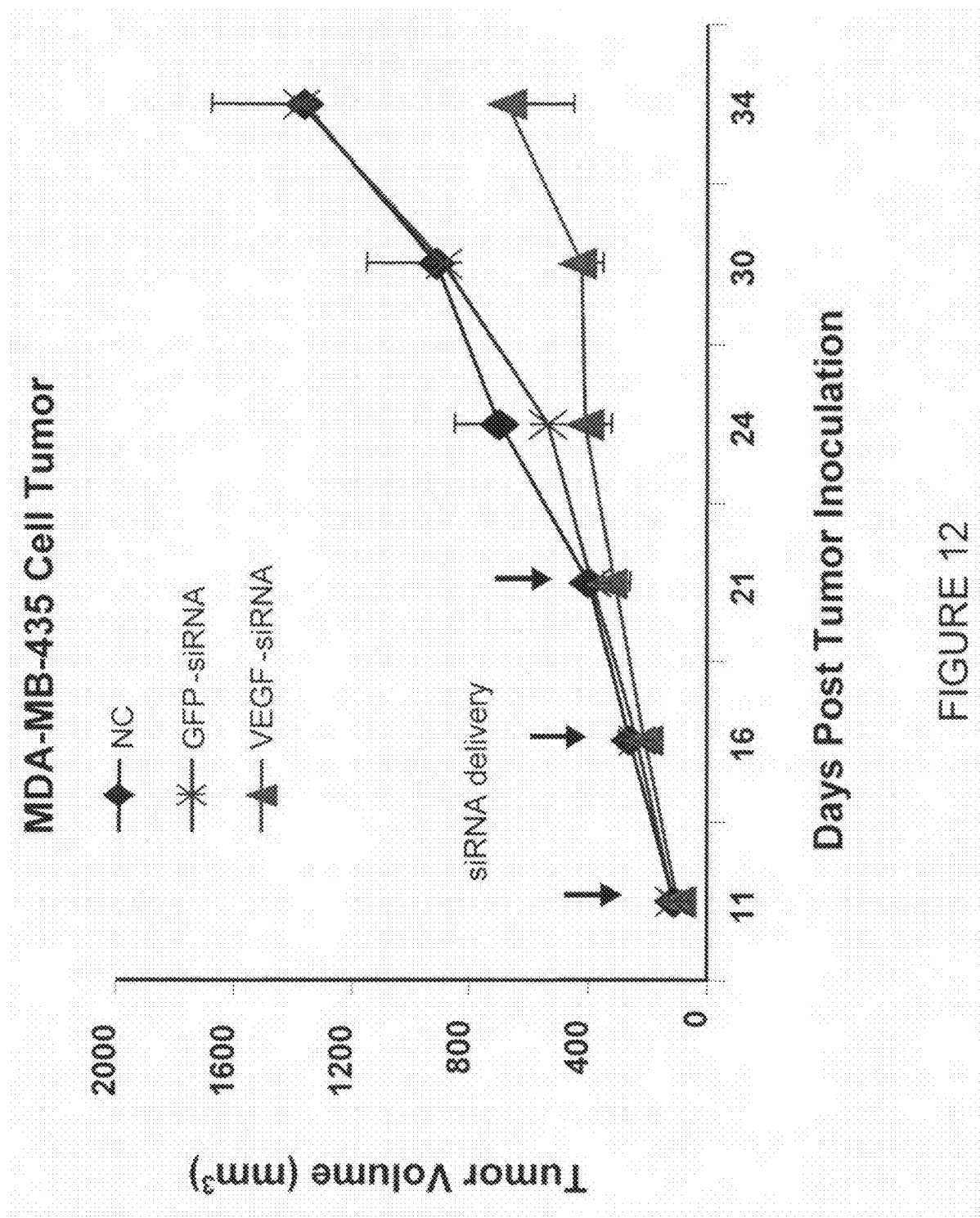
FIG. 12. Human VEGF-siRNA (25 base pair blunt end) is effective for silencing hVEGF expression in vivo resulting in tumor growth inhibition, with a MDA-MB-435 breast carcinoma cell line.

25 Basepair Blunted Double-Stranded siRNA Mediated Strong Anti-Tumor Efficacy in MDA-MB-435 Xenograft Tumor 25 basepair long siRNA duplex targeting human VEGF 165 gene sequence demonstrated strong activity of tumor growth inhibition, after three repeated intratumoral administrations of 10 µg every 5 days (FIG. 12), using a MDA-MB-435 breast carcinoma cell line known having high expression of VEGF and bFGF proteins.

Figure 13:
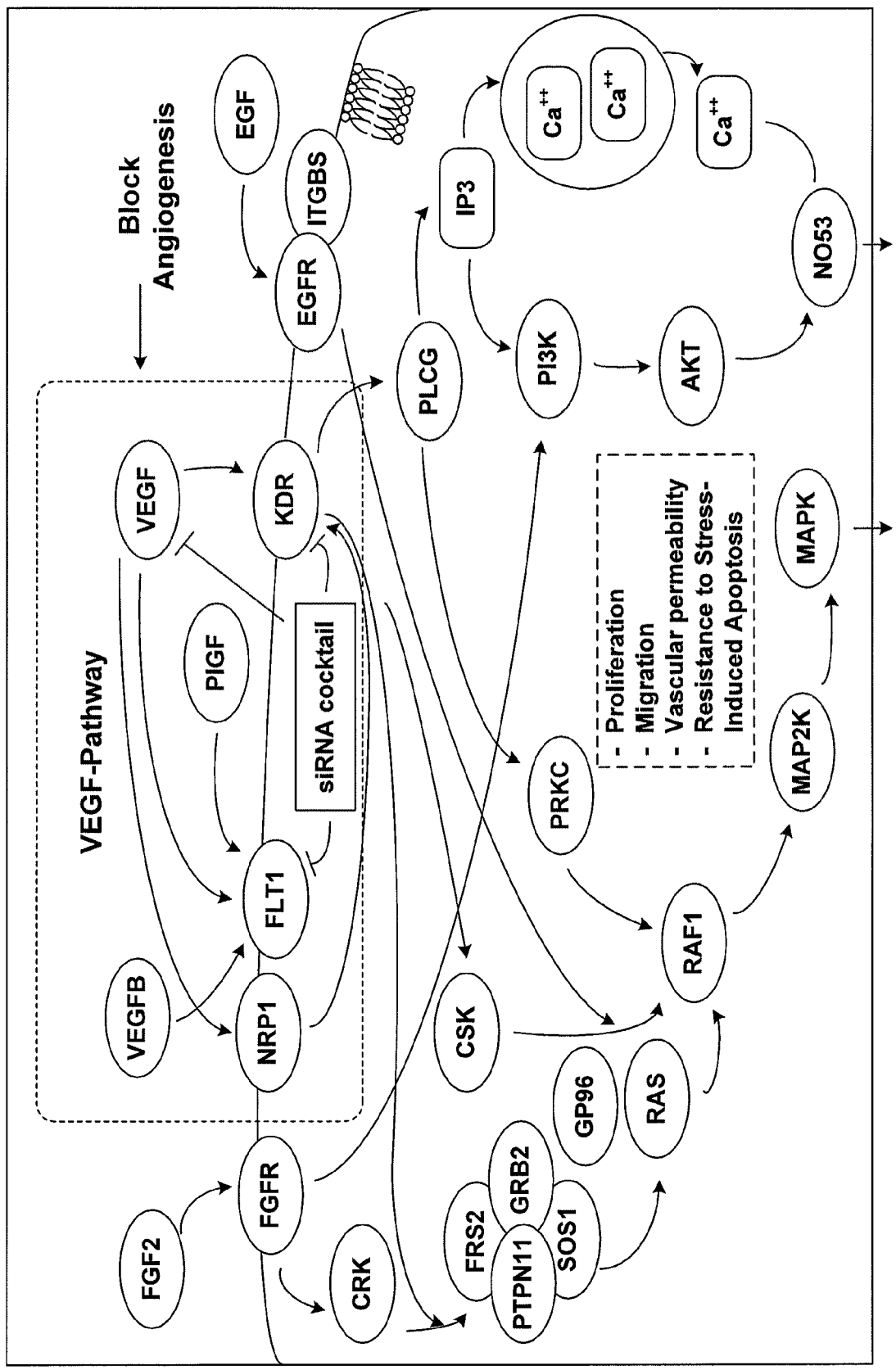
FIG. 13. Concept framework for using siRNA cocktail targeting VEGF, VEGFR1 and VEGFR2 in the same treatment to block the angiogenesis pathway.
Figure 14:
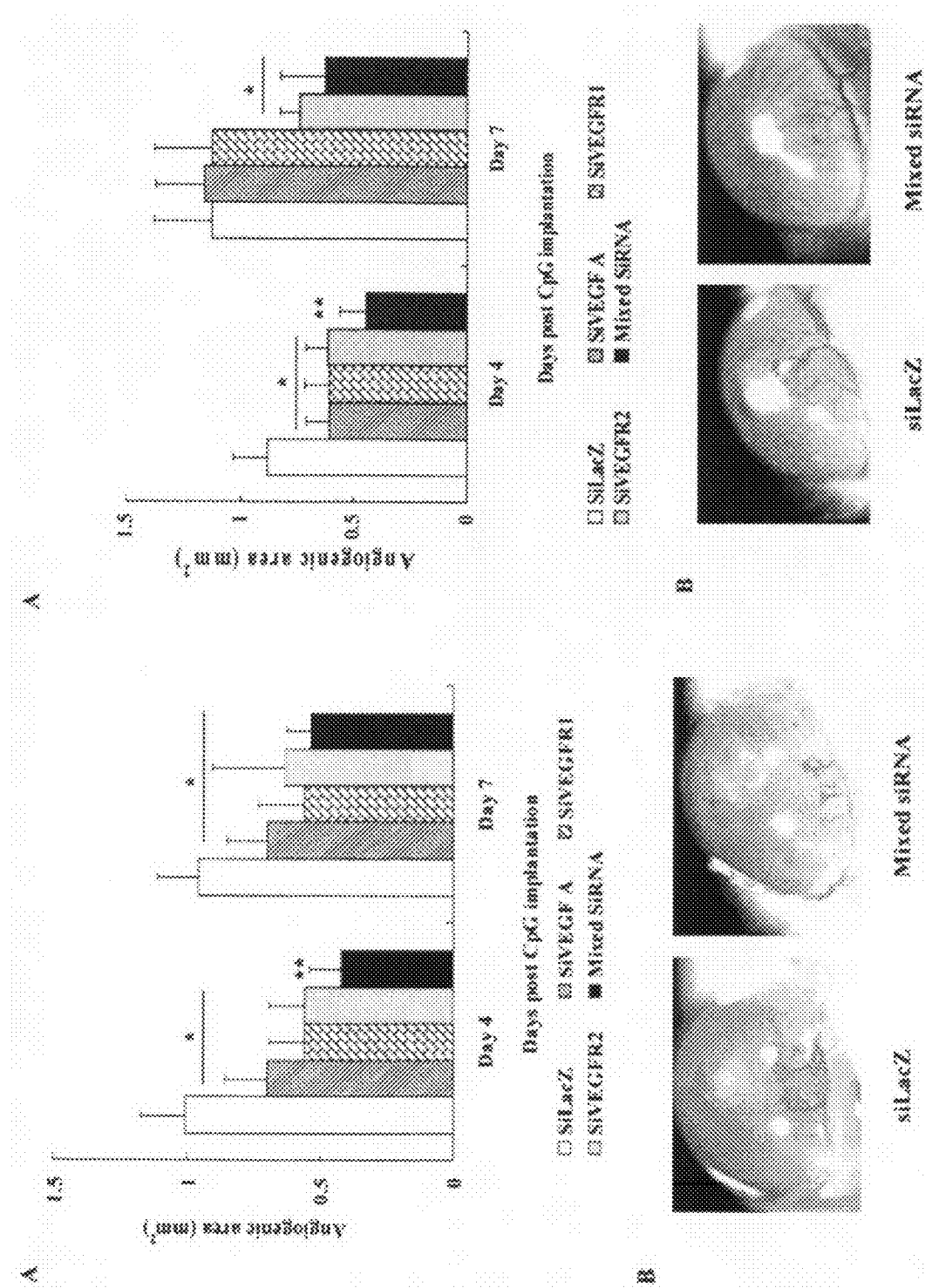
FIG. 14. siRNA cocktail targeting VEGF, VEGFR1 and VEGFR2 is more effective than any single siRNA targeting individual gene at the same dosage tested in the HSV induced ocular angiogenesis mouse model, with either local (left) or systemic (right) deliveries.
Figure 15:
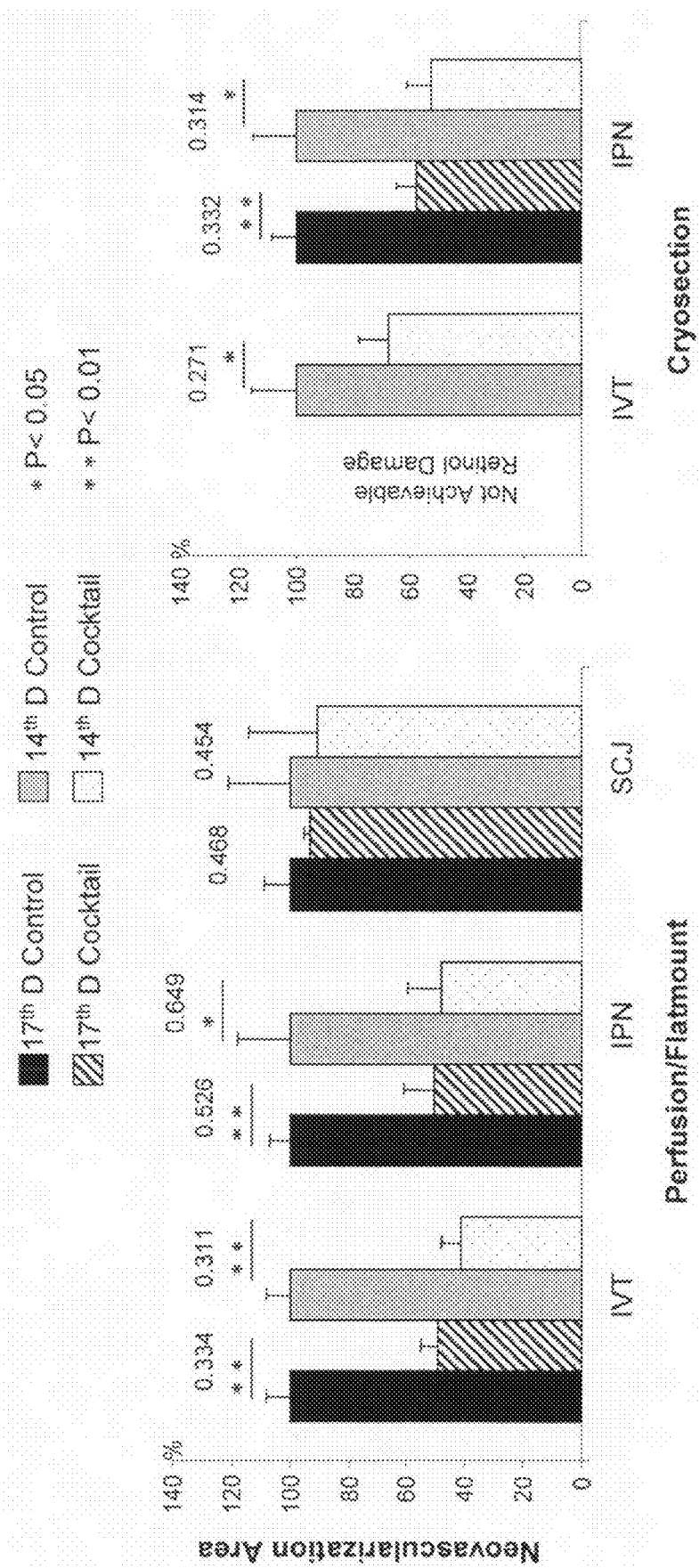
FIG. 15. Inhibition of angiogenesis by administration of VEGF pathway siRNA cocktail on day 17 or day 14 after induction of disease in ocular tissues of a murine model of retinal angiogenesis in a perfusion/flatmount measurement.
Figure 16:
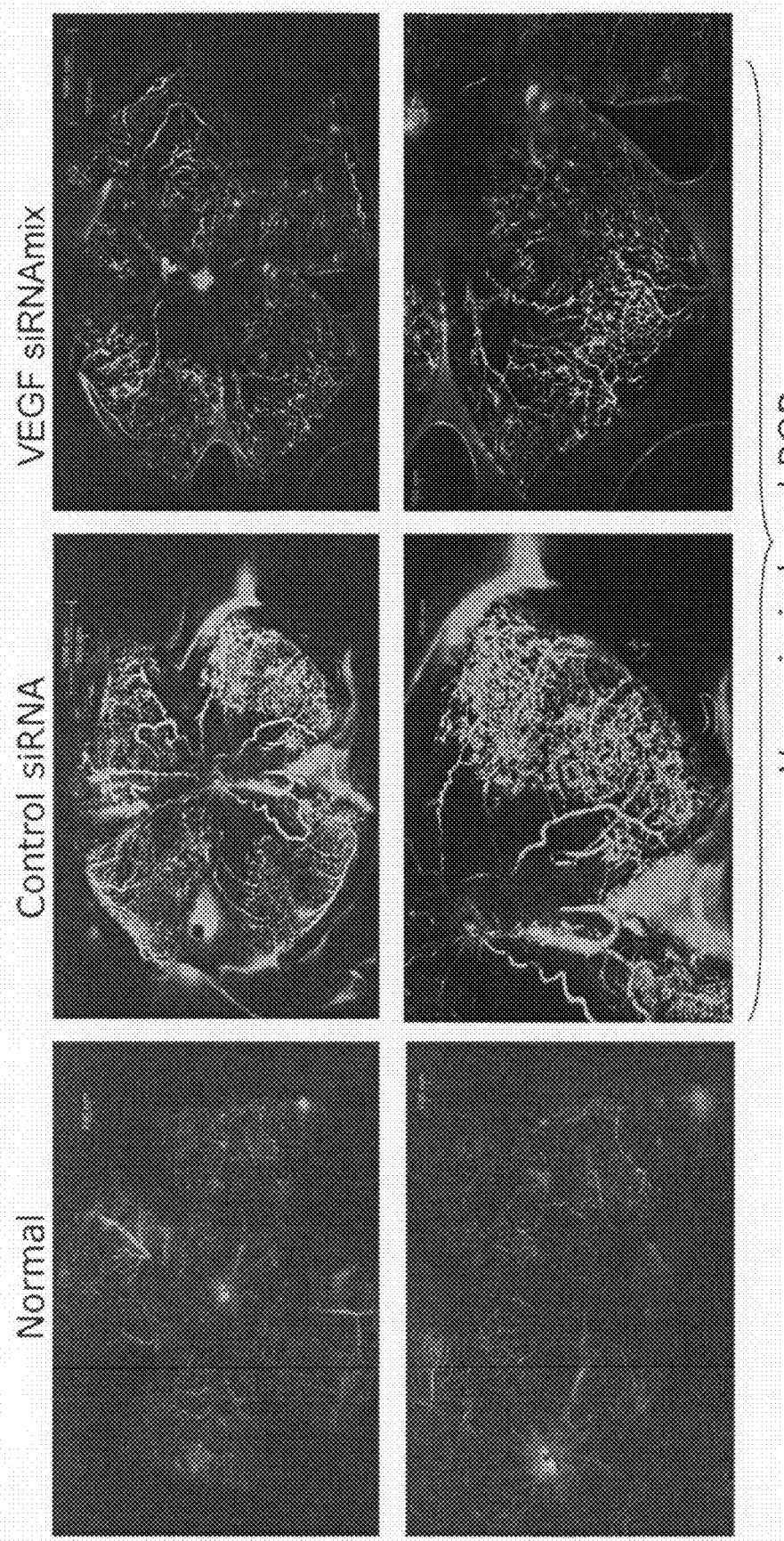
FIG. 16. siRNA cocktail targeting VEGF, VEGFR1 and VEGFR2 demonstrates very effective anti-angiogenesis activity in the retinopathy of prematural (ROP) mouse model induced by Hypoxia.
Figure 17:
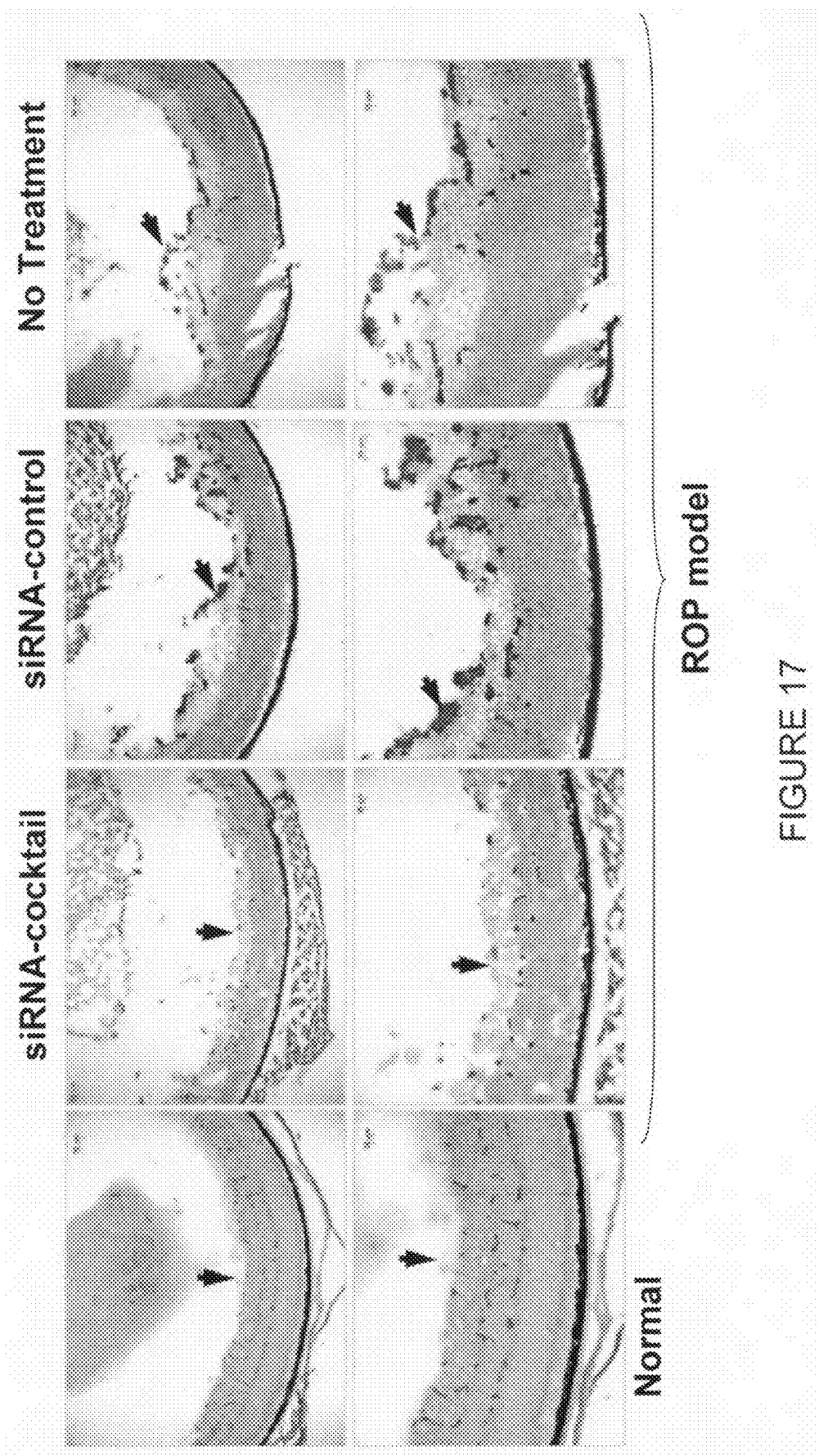
FIG. 17. siRNA cocktail targeting $VEGF_5$ VEGFR1 and VEGFR2 demonstrates very effective anti-angiogenesis activity in the retinopathy of prematural (ROP) mouse model induced by Hypoxia.
Figure 18:
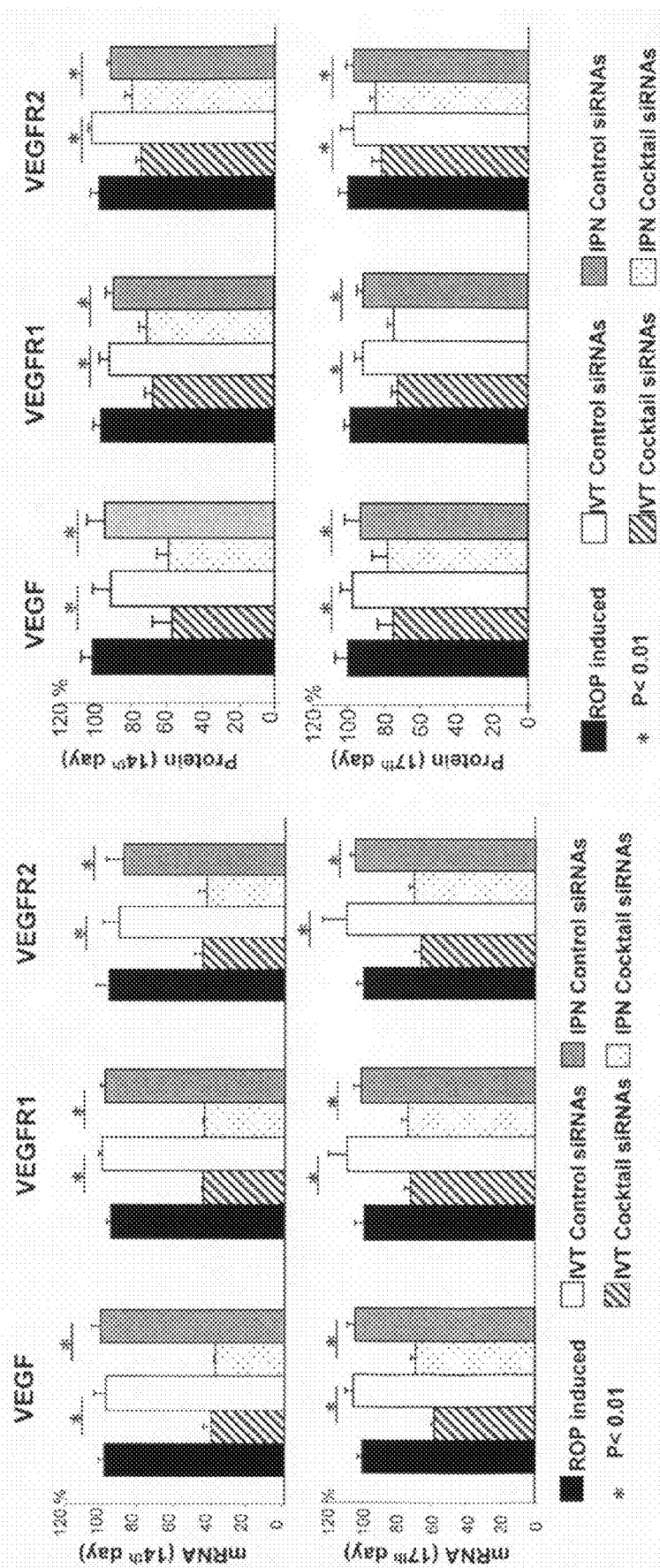
FIG. 18. siRNA cocktail targeting VEGF, VEGFR1 and VEGFR2 inhibits ocular angiogenesis significantly with different routes of administration with different carriers. IP delivery was mediated by a ligand-directed nanoparticle. siRNA Cocktail Mediated Knockdown of VEGF Pathway Factors RT-PCR Detection of mRNA levels with ROP Model.
Figure 20:
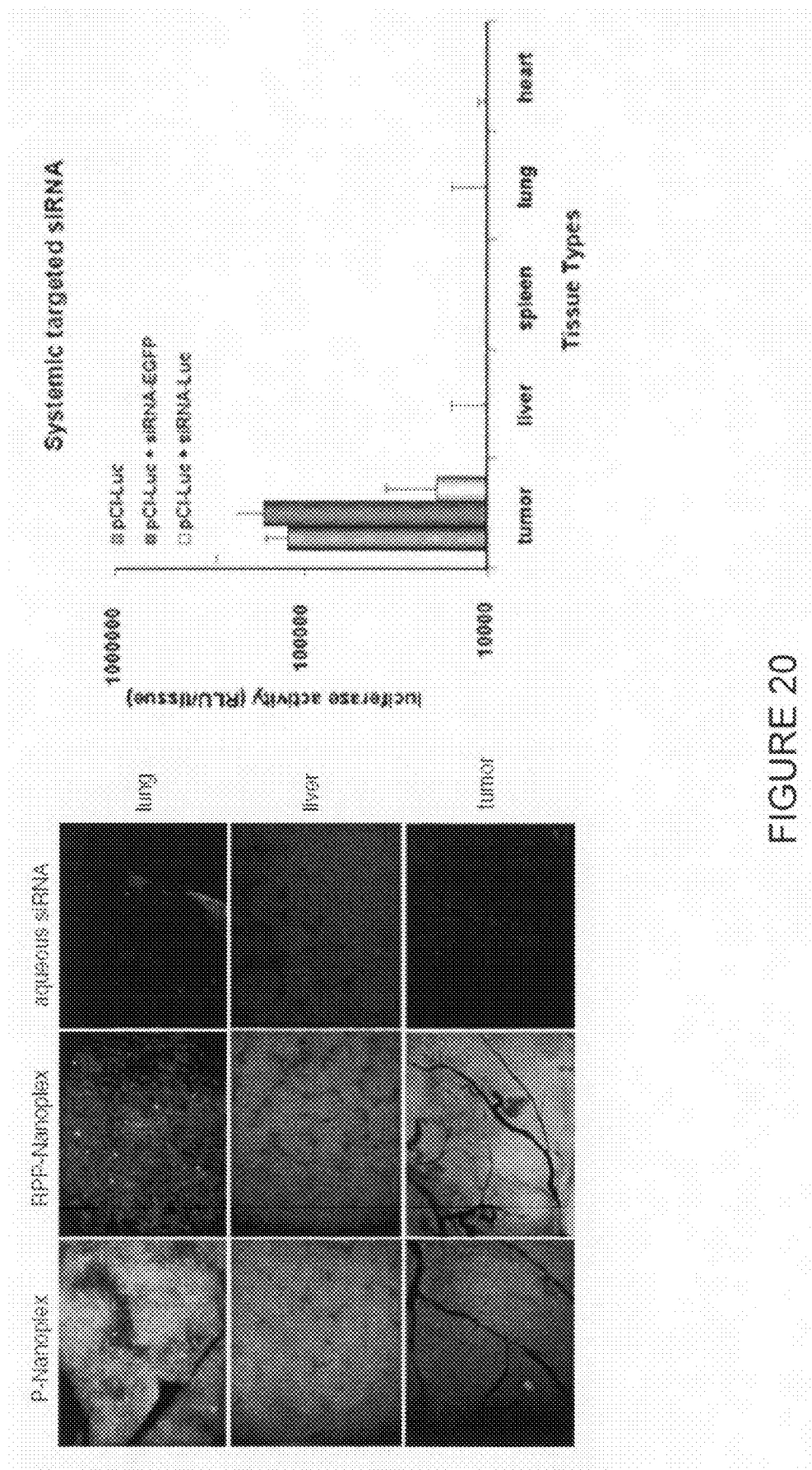
FIG. 20. siRNA nanoparticle targeting neovasculature demonstrated tumor targeting property using labeled siRNA payload (left) and plasmid payload expressing Luciferase reporter gene (right).
Figure 21:
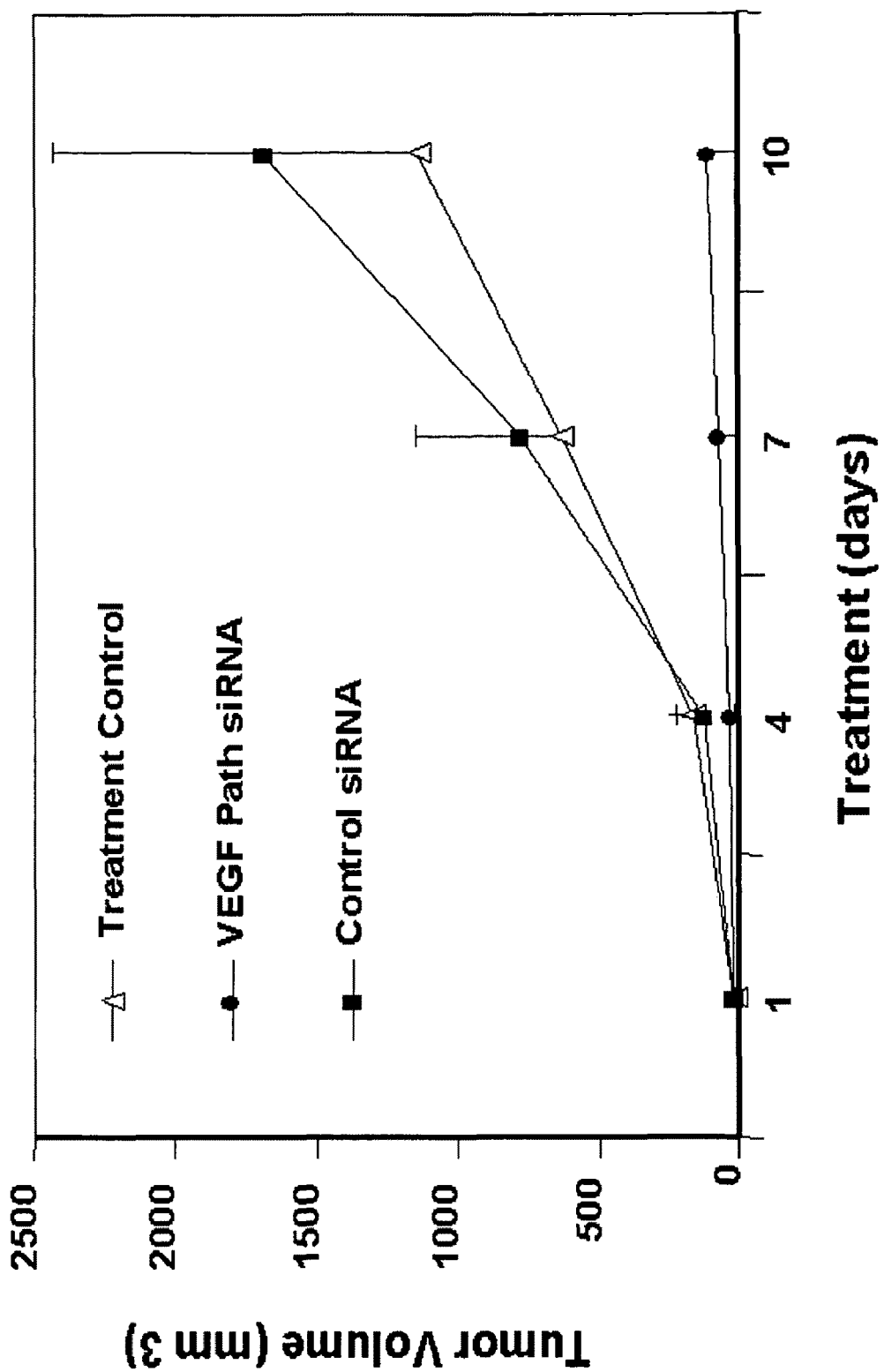
FIG. 21. VEGFR2-siRNA nanoparticle targeting neovasculature demonstrated potent efficacy in neuroblastoma syngenic mouse model (N2A tumor) after four repeated administrations every three days.
Figure 22:
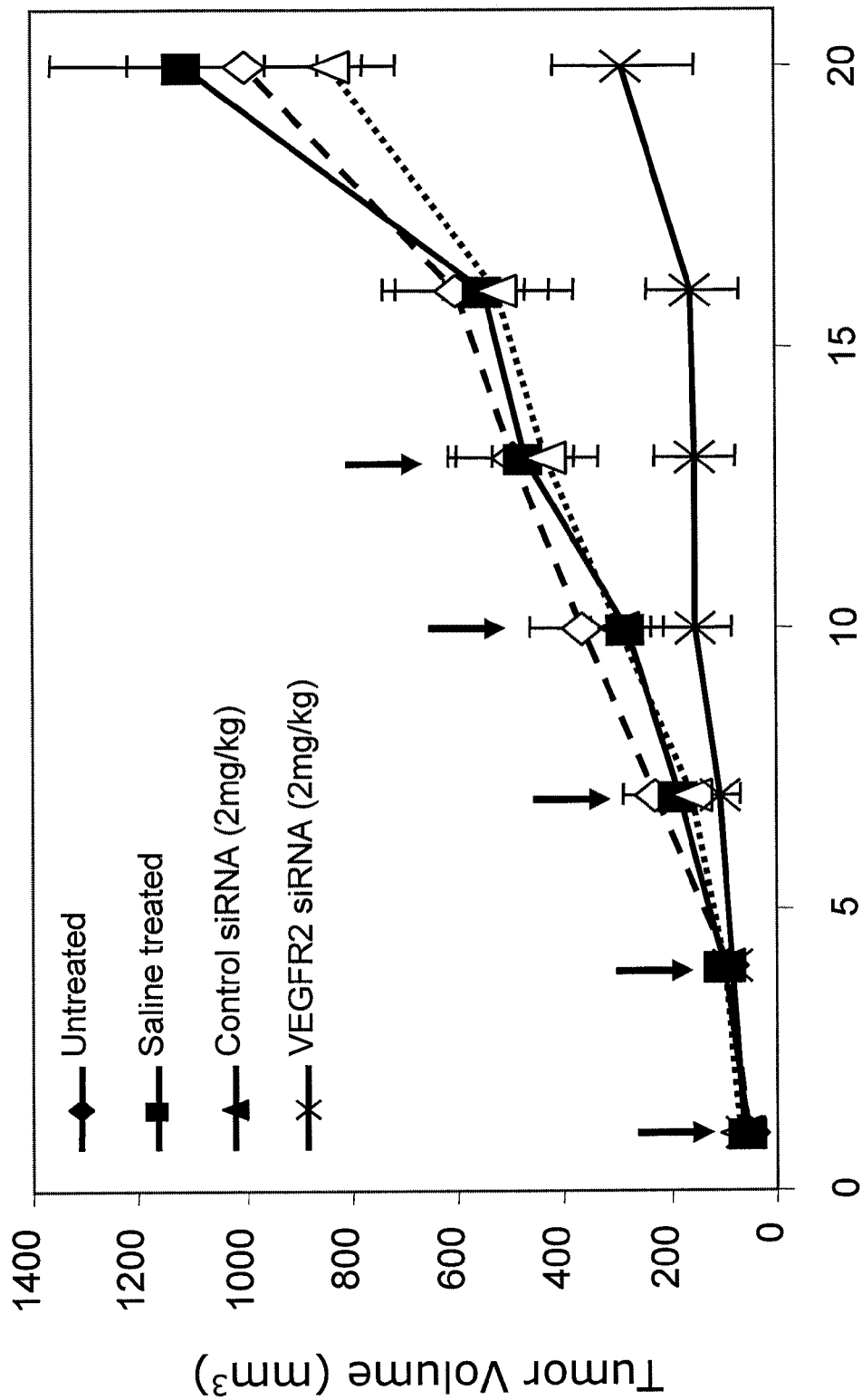
FIG. 22. VEGFR2-siRNA nanoparticle targeting neovasculature demonstrated potent efficacy in renal carcinoma xenograft mouse model (786-O tumor) after five repeated administrations every three days.
Figure 23:
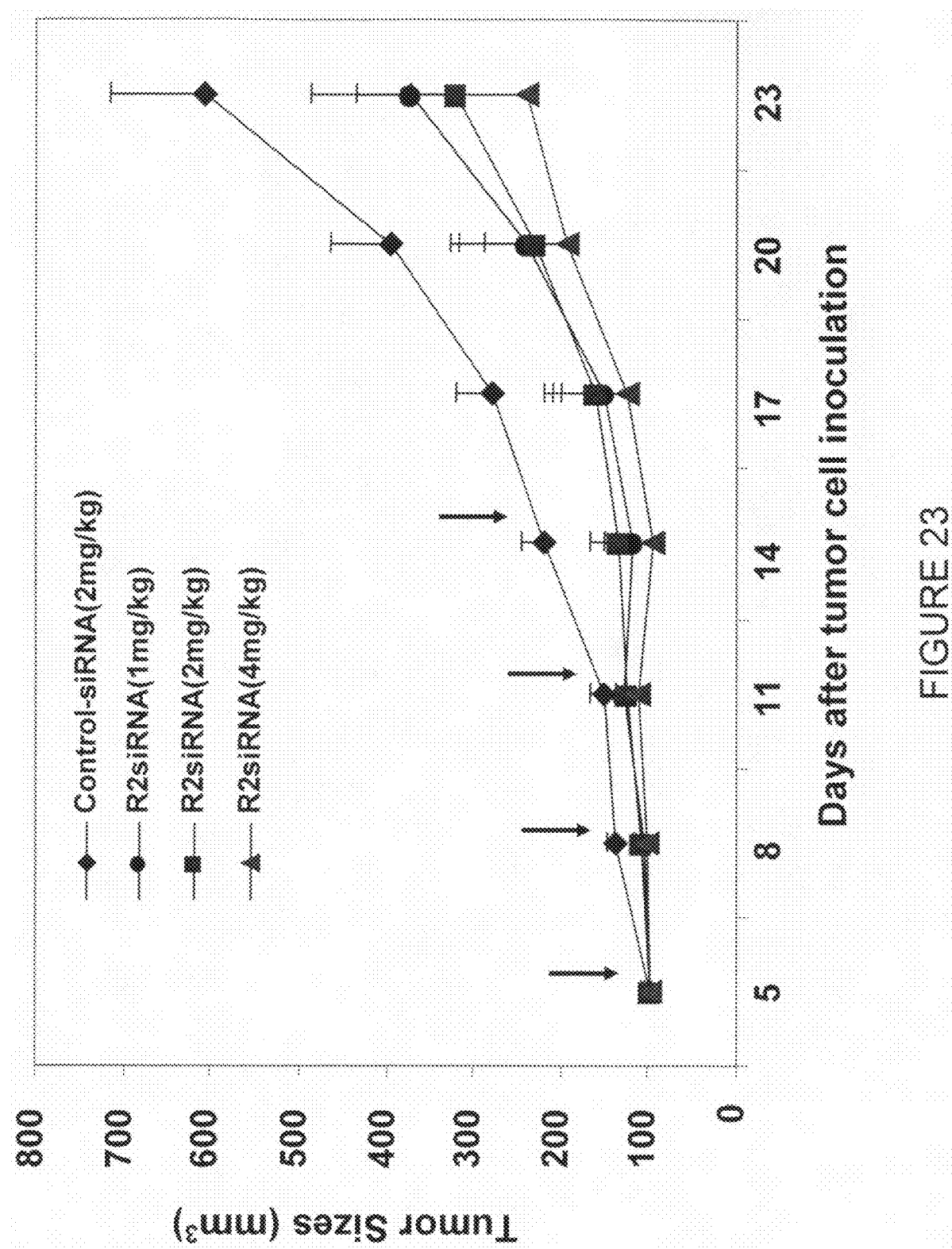
FIG. 23. VEGFR2-siRNA nanoparticle targeting neovasculature demonstrated potent efficacy in colon carcinoma xenograft mouse model (DLD-1 tumor) after four repeated administrations every three days. Three different dosages were used in the study.
Figure 24:
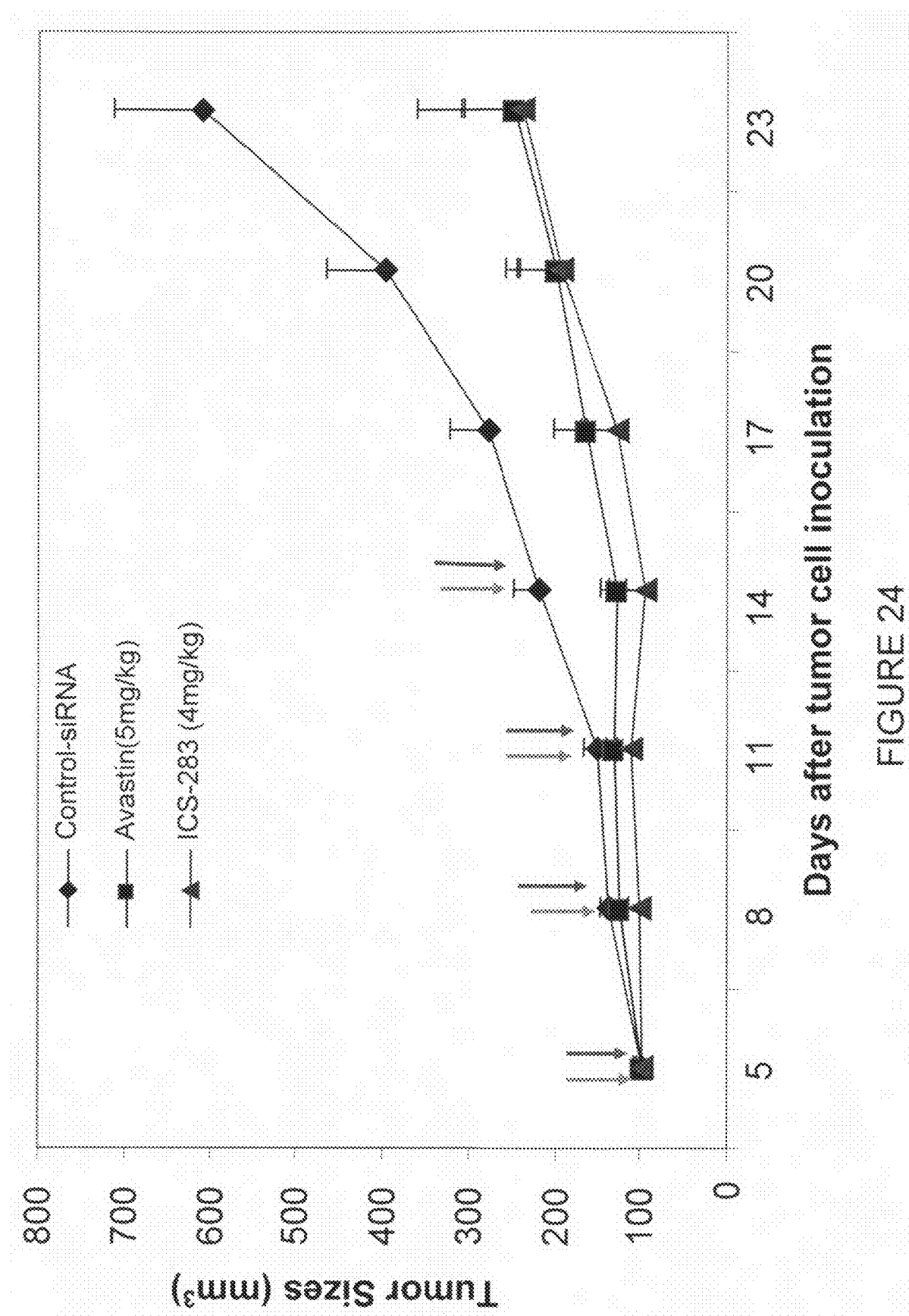
FIG. 24. VEGFR2-siRNA nanoparticle targeting neovasculature demonstrated potent efficacy in colon carcinoma xenograft mouse model (DLD-1 tumor) after four repeated administrations every three days. Four mg per kilo of VEGFR2 dosing resulted in the same anti-tumor efficacy as 5 mg per kilogram of Avastin.

Example 7 siRNA Cocktail Targeting VEGF, VEGFR1 and VEGFR1 Genes is More Potent than any of the Individual siRNA Targeting Only on of Those Genes in HSV Induced Ocular Neovascularization Model Recently, we demonstrated that the siRNA cocktail containing siRNA targeting VEGF, VEGFR1 and VEGFR2 can achieve more potent antiangiogenesis efficacy than only targeting one of those genes, at the same dosage, in the animal disease model. Using this approach, we are able to efficiently block the VEGF pathway which plays the key role for pathological angiogenesis (FIG. 13).

HSV DNA that contains abundant potentially bioactive CpG-containing motifs can induce the potent angiogenesis factor vascular endothelial growth factor (VEGF) and that neutralization of VEGF with antibody minimized HSV-induced angiogenesis. A convenient model was also established in which bioactive CpG containing oligodeoxynucleotides (ODNs) were also shown to induce neovascularization via the induction of VEGF. This model is used in the present study to evaluate the therapeutic potential of RNA interference (RNAi) to suppress VEGF expression and responsiveness.

Material and Methods

Reagents

Phosphorothioate ODNs were kindly provided by Dennis M. Klinman (Biologies Evaluation and Research, Food and Drug Administration, Washington, D.C.). The sequences of stimulatory ODNs used in this study were: 1466, TCAACGT-TGA (SEQ ID NO: 256), and 1555, GCTAGACGTTAGCGT (SEQ ID NO: 257). Subsequent studies were performed using an equimolar mixture of ODNs 1466 and 1555. *Molecular Design of Gene Targets and siRNA* Three mVEGF pathway factors, mVEGF A and two mVEGF receptors (mVEGFR1 and mVEGFR2), were targeted by RNAi. For each gene target, two target sequences were assigned at different locations on the same mRNA. siRNA were designed correspondent to the above target sequences. These siRNA were designed according to the guideline proposed by Tuschl. 14,15 The designed siRNA (duplexes of sense and anti-sense strands) were synthesized by Qiagen (Valencia, Calif.). All siRNA were 21-nucleotides long doublestranded RNA oligos with a two nucleotide (TT) overhang at the 3'-end. The targeted sequences of mVEGFA were (a) AAGCCGTCCTGT-GTGCCGCTG (SEQ ID NO: 258) and (b) AACGAT-GAAGCCCTGGAGTGC (SEQ ID NO: 259).

The targeted sequences of mVEGFR1 were: (a) AAGT-TAAAAGTGCCTGAACTG (SEQ ID NO: 260) and (b) AAGCAGGCCAGACTCTCTTTC (SEQ ID NO: 261). The targeted sequences of mVEGFR2 were (a) AAGCTCAGCA-CACAGAAAGAC (SEQ ID NO: 262) and (b) ATGCGGCG-GTGGTGACAGTA (SEQ ID NO: 263). The synthesis of unrelated siRNA controls, two target sequences each for LacZ and firefly luciferase were used. They were LacZ (a) AACAGTTGCGCAGCCTGAATG (SEQ ID NO: 264) and (b) AACTTAATCGCCTTGCAGCAC (SEQ ID NO: 265), Luc (a) AAGCTATGAAACGATATGGGC (SEQ ID NO: 266) and (b) AACCGCTGGAGAGCAACTGCA (SEQ ID NO: 267). Subsequent studies were conducted using an equimolar mixture of a and b for individual siRNA. Mice Female BALB/c mice (H-2d), 5 to 6 weeks old, were purchased from Harlan Sprague-Dawley (Indianapolis, Ind.) and housed conventionally. All investigations followed guidelines of the Committee on the Care of Laboratory Animals Resources, Commission of Life Sciences, National Research Council. The animal facilities of the University of Tennessee (Knoxville, Tenn.) are fully accredited by the American Association of Laboratory Animal Care.

Virus HSV-I strain RE (kindly provided by Dr. Robert Lausch, University of Alabama, Mobile, Ala.) was used in all of the procedures. Virus was grown in Vero cell monolayers (catalog no. CCL81; American Type Culture Collection, Manassas, Va.), titrated, and stored in aliquots at −80° C. until used.

In Vitro Efficacy of siRNA

To test the efficacy of RNAi in vitro, the following cell lines were used. RAW264.7 gamma NO cells (CRL-2278, ATCC) were used to test the efficiency of siVEGFA specific knockdown of VEGFA gene that is spontaneously expressed in these cells. The cells were plated in a six-well plate in RPMI with 10% fetal bovine serum overnight at 37° C. in 5% $CO_2$. One day after cell plating, the cells were transfected with different concentrations of siVEGFA or siLuc (at 0, 0.1, 0.5, 1.0, or 2.0 µg/2 ml/well, respectively) using Lipofectamine 2000 (Invitrogen, Carlsbad, Calif.). Twenty-four hours later RNA from these cells was extracted for reverse transcriptase-polymerase RNA Extraction and RT-PCR). SVR cells (CRL-2280, ATCC) were used to test the efficiency of siVEGFR1-specific knockdown of VEGFR1 gene that is constitutively expressed on these cells. The cells were plated in a six-well plate in Dulbecco's modified Eagle's medium with 5% fetal bovine serum overnight at 37° C. in 5% $CO_2$. One day after cell plating, the cells were transfected with different concentrations of siVEGFR1 or siLuc (at 0, 0.1, 0.5, or 1.0 µg/2 ml/well, respectively) using Lipofectamine 2000. Forty-eight hours later RNA from these cells was extracted for RSPCR to detect VEGFR1 (see RNA Extraction and NATemplate-Specific PCR) (RS-PCR). The 293 cells (CRL-1573, ATCC) were used to transfect with mVEGFR2-expressing plasmid for the detection of knockdown of exogenous mVEGFR2. The cells were plated in a six-well plate in Dulbecco's modified Eagle's medium with 5% fetal bovine serum overnight at 37° C. in 5% $CO_2$. One day after cell plating, the cells were cotransfected with plasmid pCI-VEGFR2 (0.2 µg/2 ml/well) and siVEGFR2 (a, b, a & b), or siLuc (0, 0.1, 0.5, or 1.0 µg/well, respectively) using Lipofectamine 2000. Forty eight hours later RNA from these cells was extracted for RS-PCR to detect VEGFR2.

Corneal Micropocket Assay

The corneal micropocket assay used in this study observed the general protocol of Kenyon and colleagues. Pellets for insertion into the cornea were made by combining known amounts of CpG ODNs, sucralfate (10 mg, Bulch Meditec, Vaerlose, Denmark), and hydron polymer in ethanol (120 mg/1 ml ethanol; Interferon Sciences, New Brunswick, N.J.), and applying the mixture to a 15 $mm^2$ piece of synthetic mesh (Sefar America, Inc., Kansas City, Mo.). The mixture was allowed to air dry and fibers of the mesh were pulled apart, yielding pellets containing CpG ODNs. The micropocket was made under a stereomicroscope (Leica Microsytems, Wetzlar, Germany) (four eyes per group) and pellets containing CpG ODNs were inserted into the micropocket. Angiogenesis was evaluated at days 4 and 7 after pellet implantation by using calipers (Biomedical Research Instruments, Rockville, Md.) with a stereomicroscope. The length of the neovessels originated from the limbal vessel ring toward the center of the cornea and the width of the neovessels presented in clock hours were measured. Each clock hour is equal to 30° at the circumstance. The angiogenic area was calculated according to the formula for an ellipse.

In Vivo Delivery of siRNA

Limbus was monitored at both day 4 and 7 after pellet implantation. Significant inhibition of corneal neovascularization resulted with all three test siRNA compared to those given control siLacZ at day 4 after pellet implantation (p<0.05). The combination of the three tested siRNA was the most effective inhibitor, providing an approximately 60% reduction in neovascularization (p<0.01).

Inhibition of CpG-Induced Neovascularization by Systemic Delivery of siRNA Targeting VEGF-Pathway Genes.

To test the anti-angiogenic effect of targeted individual siRNA and the efficiency of systemic siRNA delivery, mice with CpG ODN-containing micropockets were given a single dose i.v. of 40 µg siRNA containing either siVEGFA, siVEGFR1, siVEGFR2, a mix of the three, or control siLacZ 6 and 24 h post pellet implantation. In these experiments a polymer ("Targetran") was used that was shown in previous studies on tumor angiogenesis to facilitate extravascular delivery of siRNA. At day 4 and 7 after pellet implantation, the extent of angiogenesis was measured. All reagents used individually induced significant inhibition of neovascularization compared to the siLacZ treated group at day 4 after pellet implantation (p<0.05). As observed with local administration, the mix of the three test reagents provided the most effective inhibition (average 40% inhibition, p<0.01). In additional experiments, the function of the polymer vehicle was evaluated by comparing the anti-neovascularization activity of the test mix suspended in polymer or given in PBS. These experiments revealed that the use of the polymer vehicle resulted in more effective anti16 neovascularization than was evident when the PBS vehicle was used although result was only significant at the early test period (p<0.05). The results demonstrate that ocular neovascularization can be controlled by the i.v. administration of siRNA that target the VEGF system genes and that the use of the RGD-mediated dsRNA nanoparticle delivery enhanced the efficacy of the therapeutic effect.

To determine the efficient anti-angiogenic dose of siRNA in systemic delivery, mice with CpG ODN-containing micropockets were given a single dose i.v. of 10, 20, 40, 80 µg siRNA containing a mix of the siVEGFA, siVEGFR1 and siVEGFR2, or control siLuc with TargeTran vehicle at 6 and 24 h post pellet implantation. A administration of siRNA inhibited CpG induced angiogenesis in a dose dependent manner.

Therapeutic Application of siRNA Against VEGF-Pathway Genes in the HSK Model.

Figure 4:
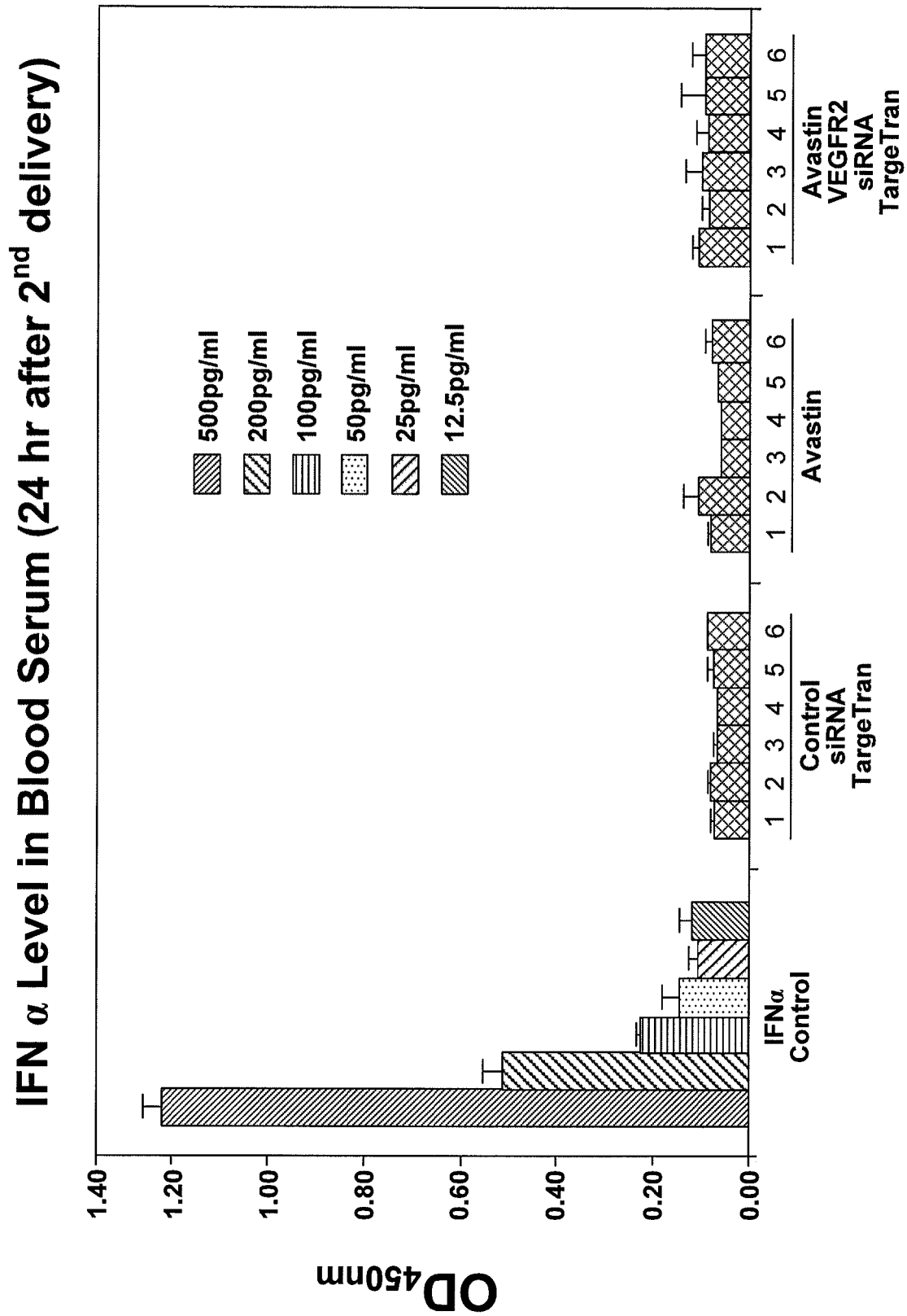
FIG. 4. While human VEGFR2-siRNA nanoparticle targeting neovasculature through systemic delivery demonstrated potent efficacy in colon carcinoma xenograft mouse model (DLD-1 tumor), no significant IFN-α induction was observed in the mouse blood stream 24 hours after the 2nd delivery.
Figure 5:
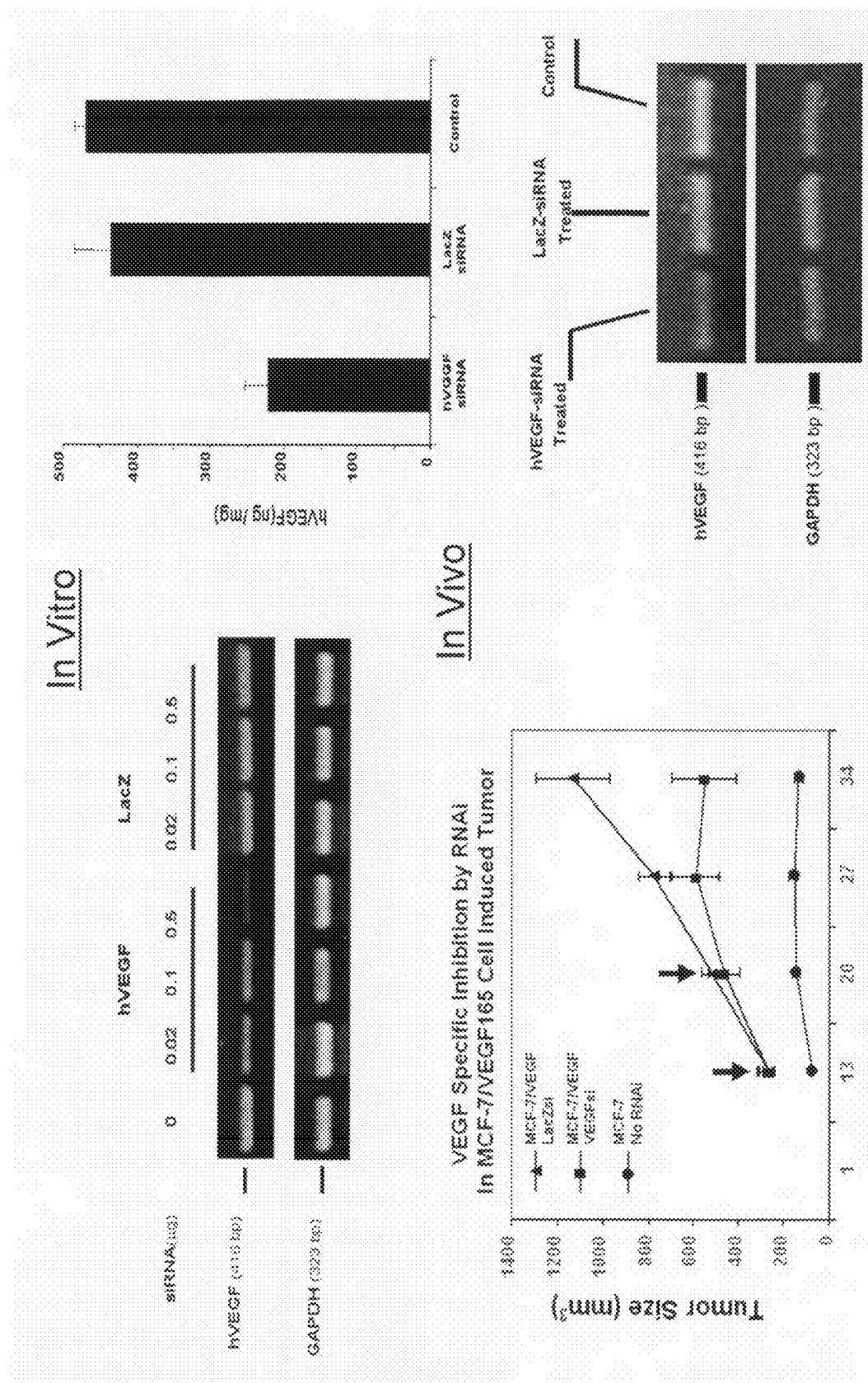
FIG. 5. Human VEGF-siRNA (19 base pair with 3' end overhangs) is effective for silencing hVEGF expression in vitro and in vivo, at both mRNA level and protein level, evaluated by RT-PCR and ELISA. Two upper figures demonstrated significant hVEGF knockdown at both mRNA and protein levels. The lower panel shows the anti-tumor activity of siRNA-mediated hVEGF knockdown in a MCF-7/VEGF165 cell induced xenograft model, where the hVEGF expression was significantly down regulated in the tumor tissue.
Figure 6:
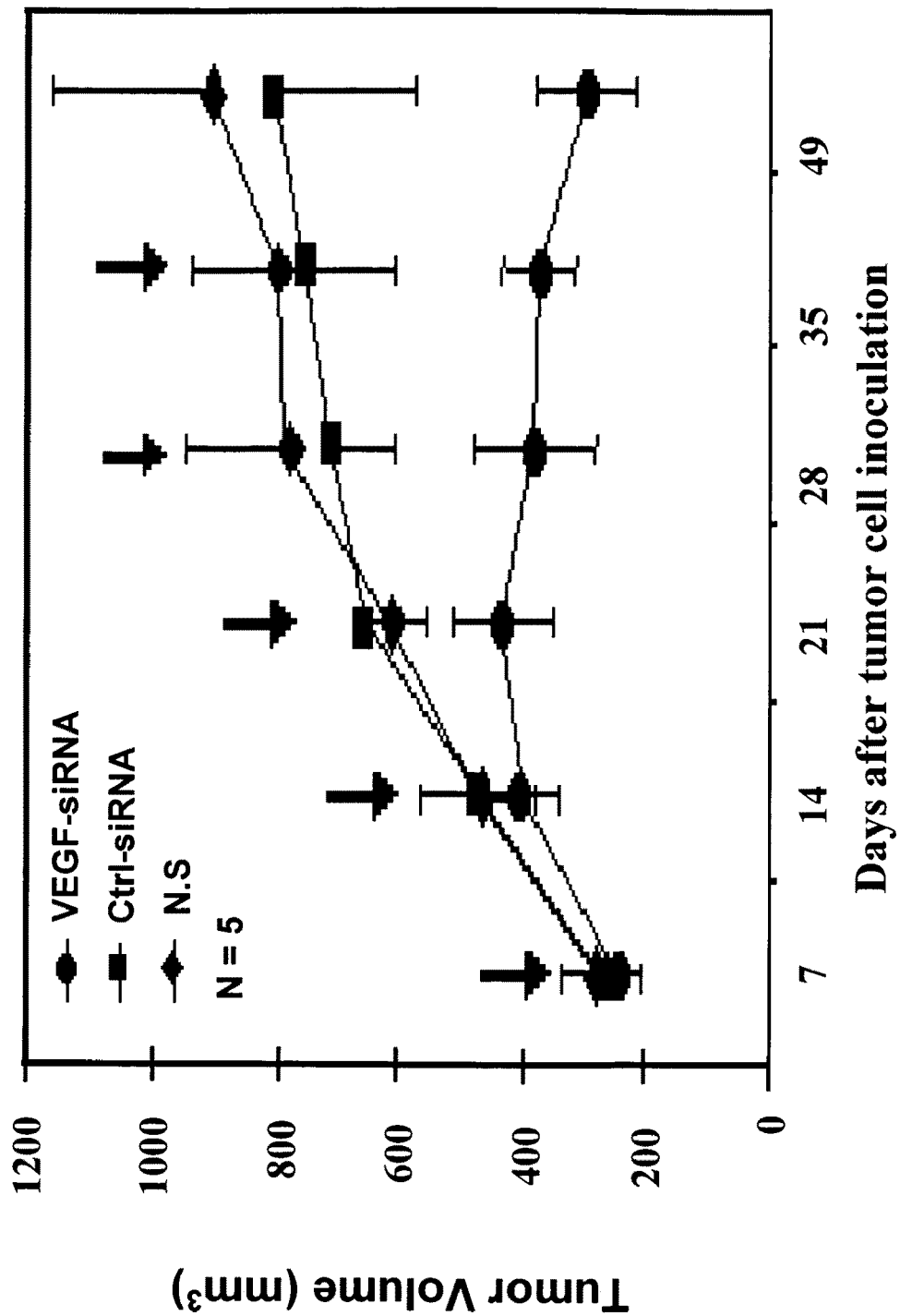
FIG. 6. Human VEGF-siRNA (19 base pair with 3' end overhangs) is effective for silencing hVEGF expression in vivo resulting in tumor growth inhibition (HNSCC 1483 cell). Five times repeated intratumoral delivery with electroporation enhancement with 7 day interval.

Previous studies have shown that VEGF is the critical angiogenic factor for induction of HSV specific angiogenesis in the HSK model. To evaluate whether administration of siRNA targeting VEGF-pathway genes inhibits the development of HSK, the corneas of mice were scarified and infected with 1-105 HSV-1 RE. Then mice were given a single dose of 10 µg (subconjunctival injection for local delivery) or 40 µg (tail vein injection for systemic delivery) mix of siRNA (an equimolar mixture of siVEGFA, siVEGFR1, and siVEGFR2) with polymer vehicle at day 1 and 3 after virus infection. As shown in FIG. 4, the angiogenesis and severity of HSK was significantly reduced in mice treated with siRNA targeting VEGF-pathway genes either locally or systemically compared to animals treated with siLuc control (p<0.05). Whilst 80% of siLuc control treated eyes developed clinically evident lesions (score 2 or greater at day 10 p.i.), only 42% (local delivery) or 50% (systemic delivery) of eyes treated with siRNA targeting VEGF-pathway genes developed such lesions. In addition by day 10 p.i., the angiogenesis score was greater than 6 in 9 of 12 control eyes, but only in 5 of 12 eyes of mice treated with siRNA against VEGF-pathway genes by either local or systemic delivery. Taken together these results show that administration of siRNA against VEGF-pathway genes reduced development of HSK via inhibition of angiogenesis.

Example 8 siRNA Cocktail Targeting VEGF, VEGFR1 and VEGFR1 Genes Very Potent Anti-Angiogenesis Agent in ROP Ocular Neovascularization Model Neovascularization in the eye is associated with various disorders, often causing severe loss of vision and eventually blindness. Among these disorders, diabetic retinopathy (DR), age-related macular degeneration (AMD), retinal vein occlusion (RVO) and retinopathy of prematurity (ROP) are prevalent. The imbalance of stimulatory factors and inhibitory factors result in NV (NV) and vascular endothelial growth factor (VEGF) is the most important factor of stimulatory factors which cause vascular permeability, dilation and endothelial cell migration, proliferation[1].

RNA interference (RNAi) is the process of sequence-specific post-transcriptional gene silencing in a wide range of organisms, initiated by double stranded RNA (dsRNA) that is homologous in sequence to the targeting gene. In this example, small interference dsRNA oligonucleotides (siRNA) targeting VEGF path ways were used to inhibition NV induced by oxygen-induced retinopathy.

Materials and Methods

The Design and Synthesis of siRNA siRNA was kindly provided by Intradigm Corporation. Three mVEGF pathway factors, mVEGF A and two mVEGF receptors (mVEGFR1 and mVEGFR2) were targeted by RNAi and called siMix. The siRNA targeting luciferase was called siLuc as control.

Mouse Model of Oxygen Induced Retinal Neovascularization

The model we used (Smith et al.[2]) imitates retinopathy of prematurity. On postnatal day seven (P7) the mice and their nursing mother were placed in an airtight incubator (own production) ventilated by a mixture of oxygen and air to a final oxygen fraction of 75%±2%. Oxygen levels were checked at least 3 times a day. On P12 the mice were returned to room air. On P17 the animals were sacrificed.

Mice

The C57BL/6 mice were purchased from center of experimental animal of Guangzhou Medical college and Guangzhou University of traditional Chinese Medicine. All investigations followed guidelines of the Committee on the Care of Laboratory Animals Resources, Commission of Life Science, National Research Council.

In Vivo Delivery of siRNA

For local delivery, siMix (4 μg/2 μl per eye) was delivered subconjunctivaly or intravitreally in the left eye and siLuc (4 μg/2 μl per eye) in the right eye by a 32-gauge Hamilton syringe (Hamilton Co, Revo, Nev.) on P12 and P13 under deep anesthesia. For systemic administration, siRNA (15 μg/50 μl per mouse) was mixed with the RGD-PEG-PEI polymer conjugate preparation (TargeTran) and delivered intraperitoneally on P12 and P13.

Retinal Angiography[4]

On P17 the animals were sacrificed by cardiac perfusion with a solution of 50 mg/ml fluorescein-labeled dextran in sodium chloride as described previously. Both eyes were enucleated and fixed for 0.5-1 h in 10% buffered formaldehyde at room temperature. The anterior segment was cut off and the neurosensory retina carefully removed. The retina was cut radially and flat mounted in glycerin, photoreceptors facing downward. A cover slip was placed over the retina and sealed with nail polish. Retinal whole mounts were examined by fluorescence microscopy. The areas of retinal NV were measured by soft Image-Pro Plus (Media Cybernetics, USA).

Cryosection[5]

Eyes were removed and frozen in optimal cutting temperature embedding compound (Miles Diagnostics). Ocular frozen sections (10 μm) were histochemically stained with biotinylated GSA. Slides were incubated in methanol/$H_2O_2$ for 10 min at 4° C., washed with 0.05 M Tris-buffered saline (TBS), pH 7.6, and incubated for 30 min in 10% normal bovine serum. Slides were incubated 1 h at 37° C. with biotinylated GSA and after rinsing with 0.05 M TBS, they were incubated with avidin coupled to alkaline phosphatase (Vector Laboratories) for 45 min at room temperature. After being washed for 10 min with 0.05 M TBS, slides were incubated with diaminobenzidine to give a brown reaction product and were counterstained with eosin, mounted with Cytoseal. To perform quantitative assessments, 10 μm serial sections were cut through entire eyes, and starting from the 1st section that contained iris and extending to the last section on the other side of the eye that contained iris, every tenth section was stained with GSA and total 15 sections were stained. GSA-stained sections were examined with an microscope, and images were digitized using a digital color video camera. Image-Pro Plus software (Media Cybernetics, Silver Spring, Md., USA) was used to delineate GSA-stained cells on the surface of the retina and their area was measured. For local injection the total measurements from each eye was used as a single experimental value. For systemic injection the mean of both eyes of a mouse was used as a single experimental value.

RT-PCR

On P14 and P17 the mouse were sacrificed and total RNA was extracted from retinae with TRIzol reagent (Invitrogen, USA). Total RNA was quantified at a ratio of 260 to 280 nm and 2 ug RNA was converted to cDNA via cDNA synthesis Kit (Fermentas, USA). RT-generated cDNAs encoding VEGF, VEGFR1, VEGFR2 and b-actin (acting as a control of RNA integrity and as an internal standard) were amplified with RT-PCR. Amplification of 1.5 ul of cDNA was performed with 1 ul sense and antisense and 2.5 U of Taq polymerase. The oligonucleotide primer sequences are: mVEGF (430 bp) ☐ forward 5'—GAT GTC TAC CAG CGA AGC TAC TGC CGT CCG—3' (SEQ ID NO: 268) ☐ reverse 5'—GAA CAT CGA TGA CAA GCT TAG GTA TCG ATA caa gct gcc teg cct tg—3' (SEQ ID NO: 269) ☐ mVEGFR1 (404 bp) ☐ forward 5'—GTCAGC TGC TGG GAC ACC GCG GTC TTG CCT—3' (SEQ ID NO: 270) ☐ reverse 5'—GAA CAT CGA TGA CAA GCT TAG GTA TCG ATA tag art gaa gat tec gc—3' (SEQ ID NO: 271) ☐ mVEGFR2 (485 bp) ☐ forward 5'-TGG CTG GTC AAA CAG CTC ATC-3' (SEQ ID NO: 272) ☐ reverse 5'-CTC ATC CAA GGG CAA TTC ATC-3' (SEQ ID NO: 273) ☐☐ β-actin (232 bp) ☐ forward 5'-CAT TGT GAT GGA CTC CGG AGA CGG-3' (SEQ ID NO: 274) ☐ reverse 5'-CAT CTC CTG CTG AAG TCT AGA GC-3' (SEQ ID NO: 275).

ELISA for VEGF and VEGF 1, VEGFR2

On P14 and P17 the mouse were sacrificed and retinae were extracted quickly on ice. Samples were homogenized in a cell lysis buffer (Mammalian cell lysis Kit, Biotechnology Department Bio Basid Inc, Canada) and were subsequently centrifuged at 12,000 rpm for 30 min. The supernatants were analyzed for protein concentrations via the BCA protein quantitative analysis Kit (Shenery Biocolor Bioscience & Technology Company, China). Samples were diluted to a final concentration of 1 mg/ml. Levels of VEGF, VEGFR1, and VEGFR2 were determined using the Quantikine M Murine VEGF, sVEGFR1, and sVEGFR2 Immunoassay Kits, respectively (R&D Systems Inc., Minneapolis, Minn.). Six to 12 tissue samples were analyzed for each group and time point.

Results and Discussion

Fluorescein Angiographic Assessment of the Effect of siRNA on Retinal NV

The retinas of the normal P17 mouse had both superficial and deep vascular layers (joined by connecting vessels) that extended from the optic nerve to the periphery. Retinas from P17 control mouse exposed to hyperoxia contained many neo vascular tufts (high fluorescein) extending from the surface of the retina at the junction between the perfused and nonperfused retina. After subconjunctival injection of siLuc or siMix the retinas also had many NV, the areas had no obvious differences. Whereas the areas of NV after intravitreal and intraperitoneal injection of siMix were significant less than the control.

Assessment of Effects of siRNA by Histologic Quantitation of Retinal NV.

Retinal NV was also assessed histologically by measured the GSA-positive cells (neovascularization) anterior to the internal limiting membrane (ILM). Retinas of P17 normoxic mice had superficial, middle, deep vessels and contained no endothelial cells anterior to the ILM. Retinas of P17 mice subjected to hyperoxia contained multiple neovascular tufts on the surface with some extending into the vitreous. Retinas of mice treated with subconjunctival injection of siLuc or siMix had no difference with the areas of NV. The areas of NV after intravitreal and intraperitoneal injection of siMix were obviously reduced compared to siLuc injection.

Decreased Level of VEGF, VEGFR1, VEGFR2 mRNA after Intravitreal and Intraperitoneal Injection of siRNA To address whether treatment of siRNA against VEGF pathway genes reduces the levels the VEGF, VEGFR1, VEGFR2 mRNA, retinas were collected on P14 and P17 after intravitreal and intraperitoneal injection of siRNA. The mRNA levels were measured by RT-PCR. The expression of VEGF, VEGFR1, VEGFR2 mRNA were reduced in the retinas treated with siMix against VEGF pathway genes compared to the control retinas treated with siLuc (p<0.05).

Decreased Expression of VEGF, VEGFR1, VEGFR2 Protein Levels after Intravitreal and Intraperitoneal Application of siRNA To evaluate whether treatment of siRNA targeting VEGF pathway genes diminishes the production of VEGF, VEGFR1, VEGFR2 protein, ELISA was used to measure VEGF, VEGFR1, VEGFR2 protein in siRNA-treated retinas on P14 and P17. As shown in table 1 and 2, VEGF, VEGFR1, VEGFR2 protein levels were lower in those that received siMix compared controls given with siLuc.

Imbalance in the demand and supply of oxygen and nutrients is the initiating factor of neovascularization which induces upregulation of VEGF. VEGF is not only the potent mitogenic factor for endothelial cells; it also induces vascular permeability and dilation. These biological activities are mediated by binding VEGF to high-affinity transmembrane autophosphorylating tyrosine kinase receptors[5]. Three distinct VEGF receptors have been identified, namely VEGFR1 (fms-line tyrosine kinase-1 or Flt-1), VEGFR2 (kinase insert domain-containing receptor or KDR) and VEGFR3 (fms-line tyrosine kinase-4 or Flt-4). VEGFR1 and VEGFR2 are predominantly expressed on vascular, VEGFR3 on lymphatic endothelium[6]. Increased intravitreal and intraretinal levels of VEGF are associated with retinal neovascularization not only in animal model but also in patients with ischemic retinopathy. These data suggest that VEGF signaling is a good target for treatment of retinal neovascularization[5].

Oxygen-induced retinopathy in mice is widely recognized in the world. Eric AP et al[7] had reported that the mRNA levels of VEGF increased dramatically between 6 to 12 h after hypoxia and remained elevated for several days and then decreased toward baseline with regression of retinopathy. So we delivered siRNA on P12 and P13 in order to interfere the synthesize of VEGF before upregulation. The results of whole mount and cryosection had proved that the NV areas of retinas treated with intravitreal and intraperitoneal injection of siMix were less than injection of siLuc. That is siMix can obviously inhibit retinal NV. To explore the mechanism the retinal VEGF, VEGFR1 and VEGFR2 expressions on P14 and P17 were examined and the mRNA and protein levels were lower than the siLuc controls. These suggested it is through inhibiting VEGF pathway genes that siMix inhibit retinal NV.

However there is no distinct difference after subconjuctival injection, so it is concluded that it hadn't achieved the effective concentration in local. After intravitreal injection there was high concentration of siRNA in vitreous and siRNA was transfected into retinal neovascular endothelial cells. But this injection can result in intraocular hemorrhage and endophthalmitis et al. Intraperitoneal injection is relative safe and siRNA can be absorbed into blood through abundant celiac capillary. But siRNA are easily trapped in the nonspecigic organs including liver, lungs, and spleen. So how to enhance the transfecting efficiency of siRNA is very important. The vehicle TargeTran is composed of polyethylene imine (PEI), polyethylene glycol (PEG) and arginine-glycine-aspartate peptide sequences (RGD). PEI binds to negative charges in phosphates of the siRNA. RGD motif has been identified as an integrin ligand of activated endothelial cells. Endothelial cells express a number of different integrins and integrin αvβ3 and α5β1 have been shown to be important during angiogenesis. Both integrins are the receptor for matrix proteins with an exposed RDG tripeptide moiety and are most prominent on activated endothelial cells during angiogenesis. Thus the application of Targetran can improve the transfecting efficiency of siRNA. Kim B et al[8] had reported the subconjunctival and intravenous injection of siMix can inhibit the CPG induced the corneal neovascularization in mice. It may also apply to other neovascular diseases.

Example 9

Ligand Directed Nanoparticle siRNA can be Specifically Delivery into Tumor with Systemic Administration This self-assembled siRNA nanoparticle has demonstrated the neovasculature targeting property when they were systemically administrated through IV injection. The tumor specific targeting capability of this siRNA nanoparticle system has been revealed with a Luciferase report gene system.

Example 10

Ligand Directed Nanoparticle siRNA is Potent Anti-Tumor Agent Validated in Mouse Syngenic Model (Neuroglioblastoma)

Tumor targeted delivery of siRNA using the targeted nanoparticle system from iv administration is demonstrated using fluorescently labeled siRNA packaged in RGD-PEG-PEI nanoparticle.

Mouse Tumor Model

Female nude mice (6-8 weeks of age) were obtained from Taconic (Germantown, N.Y.), kept in filter-topped cages with standard rodent chow and water available ad libitum, and a 12 h light/dark cycle. Experiments were performed according to national regulations and approved by the local animal experiments ethical committee. Subcutaneous N2A tumors were induced by inoculation of $1 \times 10^6$ N2A-cells in the flank of the mice. At a tumor volume of approximately 0.5-1 $cm^3$, mice received nanoplexes or free siRNA by i.v. injection of a solution of 0.2 ml via the tail vein. 40 µg fluorescently-labeled siRNA was injected in the free form or as PEI- or RGD-PEG-PEI-nanoparticle. One hr after injection, tissues were dissected and examined with a dissection microscope fitted for fluorescence. Microscopic examination of tissues was performed with an Olympus SZX12 fluorescence microscope equipped with digital camera and connected to a PC running MagnaFire 2.0 camera software (Optronics, Goleta, Calif.). Pictures were taken at equal exposure times for each tissue.

Result: Intravenous injection by tail vein of free fluorescent labeled siRNA did nor show any significant accumulation in lung, liver or tumor tissue. SiRNA delivered using PEI-nanoparticle showed highest accumulation in the lung tissue followed by liver and tumor. SiRNA delivered using RGD-PEG-PEI nanoparticle showed highest level of accumulation in tumor tissue. There was a considerable reduction in lung accumulation compared to PEI-nanoparticles and very little accumulation in liver. This experiment demonstrates tumor targeted delivery of siRNA using RGD-PEG-PEI nanoparticle.

RNAi mediated inhibition of tumor angiogenesis and tumor growth were studied using tumor targeted nanoparticle formulation containing siRNA targeted against VEGFR2. Subcutaneous tumor bearing mice were treated by intravenous injection of the nanoparticle formulation at a dose of 40 µg siRNA per injection. Injections were repeated every third day and growth of the tumor was evaluated and compared with animals treated with control formulations. Inhibition of the angiogenesis was evaluated at the end of the experiment.

Mouse Tumor Model

Female nude mice (6-8 weeks of age) were obtained from Taconic (Germantown, N.Y.), kept in filter-topped cages with standard rodent chow and water available ad libitum, and a 12 h light/dark cycle. Experiments were performed according to national regulations and approved by the local animal experiments ethical committee. Subcutaneous N2A tumors were induced by inoculation of $1\times10^6$ N2A-cells in the flank of the mice. At a tumor volume of approximately 0.5-1 cm$^3$, mice received nanoplexes or free siRNA by i.v. injection of a solution of 0.2 ml via the tail vein. The nanoparticle formulations containing siRNA were prepared by simple mixing of siRNA solutions with polymer solution at given N/P ratio.

For the tumor growth inhibition studies, the experiment was started when the tumors became palpable, at 7 days after inoculation of the tumor cells. Treatment consisted of 40 µg siRNA per mouse in RPP-nanoplexes every 3 days intravenously via the tail vein. Tumor growth was measured at regular intervals using a digital caliper by an observer blinded to treatment allocation. Each measurement consisted of tumor diameter in two directions approximately 90 degrees apart. Tumor volume was calculated as, 0.52×longest diameter× shortest diameter$^2$. At the end of the experiment, the animals were sacrificed and tumor tissue and surrounding skin was excised and put on a microscopy glass slide. Tissue examination for vascularization and angiogenesis was performed by microscopy using the Olympus microscope and camera equipment described above for fluorescent tissue measurements. Tissue was trans-illuminated to visualize blood vessels in the skin and a digital image was taken and stored as described above. Tissue was snap frozen immediately thereafter for Western blotting.

Result: Significant tumor growth inhibition was observed for animals treated with nanoparticle formulations containing VEGFR2 siRNA. Animals treated with non-specific siRNA did not show any substantial tumor growth inhibition compared to untreated animals. Significant inhibition of blood vessel growth was observed around the tumor tissue indicating the inhibition of angiogenesis in the VEGFR2-siRNA treated mice. Mice treated with control siRNA showed similar blood vessel growth as the untreated animals. Western blot analysis of the tumor lysate collected from animals of different treatment groups showed substantial reduction of VEGFR2 in VEGFR2-siRNA treated animals whereas no reduction in VEGFR2 was observed in control siRNA treated animals. These experiments clearly demonstrate the delivery of siRNA into tumor tissue from intravenous administration. Effectiveness of VEGFR2 siRNA packaged in the RGD-PEG-PEI nanoparticle to inhibit tumor growth in renal cell carcinoma model was studied using a 786-O xenograft tumor model. An experimental procedure similar to example 7 was used in this study. Briefly, female nude mice (6-8 weeks of age) were obtained from Taconic (Germantown, N.Y.). Subcutaneous 786-O tumors were induced by inoculation of $5\times10^6$ 786-O cells in the flank of the mice. At a tumor volume reached approximately 100 mm$^3$, treatment was started by i.v. injection of a solution of VEGFR2-siRNA in RGD-PEG-PEI nanoparticle via the tail vein. Control treatment groups received nanoparticles containing non-specific siRNA or saline. Treatment was repeated for several days with injections every three days. Tumor volume was measured once every three days as described in example 7. Result: Significant tumor growth inhibition was observed for animals treated with VEGFR2-siRNA nanoparticle formulation. No significant tumor growth inhibition was observed for animals treated with control siRNA nanoparticles. This experiment demonstrates that the VEGFR2 siRNA delivered by tumor targeted nanoparticle formulation can achieve tumor growth inhibition.

The ligand directed siRNA nanoparticles were systemically administrated into a C57 mouse model with subcutaneous inoculation of N2A glioblastoma cells for evaluation of the impact of VEGF knockdown on the tumor angiogenesis activity. Female nude mice (6-8 weeks of age) were obtained from Taconic (Germantown, N.Y.), kept in filter-topped cages with standard rodent chow and water available ad libitum, and a 12 h light/dark cycle. The experiments were performed according to national regulations and approved by the local animal experiments ethical committee. Subcutaneous N2A tumors were induced by inoculation of $1\times10^6$ N2A cells in the flank of the mice. At a tumor volume of 0.5-1 cm3, mice received nanoplexes or free siRNA by i.v. injection of a solution of 0.2 ml via the tail vein. The nanoplex solutions were prepared as above, at N/P ratio of 2. For tissue distribution experiments, 40 mg fluorescently labeled siRNA was injected in the free form or as P- or RPP-nanoplexes. One hour after injection, the tissues were dissected and examined with a dissection microscope fitted for fluorescence. Microscopic examination of tissues was performed with an Olympus SZX12 fluorescence microscope equipped with digital camera and connected to a PC running MagnaFire 2.0 camera software (Optronics, Goleta, Calif.). Pictures were taken at equal exposure times for each tissue.

In the co-delivery experiments, plasmid and siRNA were mixed in a 1:100 molar ratio, respectively (40 mg pLuc with 13 mg siRNA), and in the sequential delivery experiments 40 mg plasmid was delivered first, followed by 40 mg siRNA 2 h later (1:300 molar ratio). The tissues were dissected, weighed and put in ice-cold reporter lysis buffer (Promega) in magnetic beads containing 2 ml tubes (Q-Biogene, Carlsbad, Calif.), 24 h after injection of the nanoplexes. Tissues were homogenized with a Fastprep FP120 magnetic homogenizer (Q-Biogene) and samples were assayed for reporter enzyme activity using the luciferase assay system (Promega) on a Monolight 2010 luminometer (Analytical Luminescence Laboratory). In the tumor growth inhibition studies, the experiment was started when the tumors became palpable at 7 days after inoculation of the tumor cells. Treatment consisted of 40 mg siRNA per mouse in RPP-nanoplexes every 3 days intravenously via the tail vein. Tumor growth was measured at regular intervals using a digital caliper by an observer blinded to treatment allocation. Each measurement consisted of tumor diameter in two directions of_90_apart. Tumor volume was calculated as: 0.52×longest diameter×shortest diameter$^2$.

At the end of the experiment, the animals were sacrificed and tumor tissue and surrounding skin was excised and put on a microscopy glass slide. Tissue examination for vascularization and angiogenesis was performed by microscopy using the Olympus microscope and camera equipment described above for fluorescent tissue measurements. Tissue was trans-illuminated to visualize blood vessels in the skin and a digital image was taken and stored as described above. Tissue was snap frozen immediately thereafter for western blotting.

Tumor growth inhibition by siRNA RPP-nanoplexes. Mice were inoculated with N2A tumor cells and left untreated or treated every 3 days by tail vein injection with RPP-nanoplexes with siLacZ or siVEGF R2 at a dose of 40 mg per mouse. Treatment was started at the time-point that the tumors became palpable (20 mm$^3$). Only VEGF R2-sequence-specific siRNA inhibited tumor growth, whereas treatment with LacZ siRNA did not affect tumor growth rate as compared with untreated controls (n=5).

Example 11

Ligand Directed Nanoparticle siRNA is Potent Anti-Tumor Agent Validated in Xenograft Tumor Model (Renal Carcinoma)

The ligand directed siRNA nanoparticles were also tested in a mouse xenograft model with a renal carcinoma cell lines. The siRNA nanoparticles were manufactured with the same materials and same procedure, using the same route of delivery as that of Example 10. Five times of repeated deliveries with three day intervals using 2 mg/kg dosage were carried out with six animals per cohort. The significant tumor growth inhibition was observed.

Example 12

Ligand Directed Nanoparticle siRNA is Potent Anti-Tumor Agent Validated in Xenograft Tumor Model (Colorectal Carcinoma)

Using siRNA nanoparticle targeting VEGFR2 gene, we further tested the antitumor efficacy in mouse xenograft model with a human colorectal carcinoma cell line, DLD-1.

Material and Methods. Reagents: Avastin, monoclonal antibody against VEGF (25 mg/ml, Genetech); siRNA against VEGFR2, sequence (Appendix 1); siRNA against luciferase (Qiagen); Avertin made of 1.5 gram 2,2,2,Tribromoethanol and 1.5 ml t-amyl alcohol (Cat# T4840-2, Cat# 24048-6, Aldrich) in 100 ml distill water, St. Louis, Mo.]. Mice: athymus female nude mice, 5 to 6 weeks old, were purchased from TACONIC ( ) and housed conventionally. All investigations followed guidelines of the Committee on the Care of Laboratory Animals Resources, Commission of Life Sciences, National Research Council. The animal facility of Biomedical Research Institute in Rockville Md. is fully accredited by the American Association of Laboratory Animal Care. Cells: Colon carcinoma cell line, DLD-1 (CCL-221, ATCC) was grown in RPMI 1640 medium with 2 mM L-glutamine, 1.5 g/L sodium bicarbonate, 4.5 g/L glucose, 10 mM HEPES, and 1.0 mM sodium pyruvate, 10% fetal bovine serum.

Reagents

Avastin, monoclonal antibody against VEGF (25 mg/ml, Genetech); siRNA against VEGFR2, sequence (Appendix 1); siRNA against luciferase (Qiagen); Avertin made of 1.5 gram 2,2,2,Tribromoethanol and 1.5 ml t-amyl alcohol (Cat# T4840-2, Cat# 24048-6, Aldrich) in 100 ml distill water, St. Louis, Mo.]. Mice: athymus female nude mice, 5 to 6 weeks old, were purchased from TACONIC ( ) and housed conventionally. All investigations followed guidelines of the Committee on the Care of Laboratory Animals Resources, Commission of Life Sciences, National Research Council. The animal facility of Biomedical Research Institute in Rockville Md. is fully accredited by the American Association of Laboratory Animal Care. Cells: Colon carcinoma cell line, DLD-1 (CCL-221, ATCC) was grown in RPMI 1640 medium with 2 mM L-glutamine, 1.5 g/L sodium bicarbonate, 4.5 g/L glucose, 10 mM HEPES, and 1.0 mM sodium pyruvate, 10% fetal bovine serum. Procedure: 1) DLD-1 cells near confluence were harvested and resuspended in serum-free RPMI medium. 2) Mice were anaesthetized with Avertin, 0.4 ml/mouse i.p. 3) 100 million cells in 0.1 ml serum-free RPMI medium were injected into mice back s.c. on the left flank for establishment of xenograft tumor model. 4) 5 days after inoculation of tumor cells, sizes of growing tumors were measured with a caliper. Mice were then randomly grouped with 7 mice per group. Three different dosing regimen were applied: 1 mg/kg, 2 mg/kg and 4 mg/kg respectively. Although the high dose at 4 mg/kg represented the strongest anti-tumor activity, there is no significant difference amount three treatment groups. Using a different comparison, it has been found that the high dose of the siRNA nanoparticle at 4 mg/kg exhibited a stronger anti-tumor efficacy than that of 5 mg/kg Avastin treatment.

REFERENCES

1. Peter A, Campochiaro. Retinal and choroidal neovascularization. J Cell Physiol, 2000, 184:301-10.
2. Smith L E, Wesolowski E, Mclellan A, et al. Oxygen-induced retinopathy in the mouse. Invest Opthalmol Vis Sci, 1994, 35:101-11.
3. 3 D'Amato R, Wesolowski E, Smith L E. Microscopic visualization of the retina by angiography with high-molecular-weight fluorescein-labeled dextrans in the mouse. Microvasc Res 1993; 46:135-42.
4. Jikui shen, Rebecca samul, Joelle Zimmer, et al. Deficiency of Neuropilin 2 Suppresses VEGF-Induced Retinal NV. Molecular medicine, 2004, 10:12-18.
5. Unsoeld A S, Junker B, Mazitschek R, et al. Local injection of receptor tyrosine kinase inhibitor MAE 87 reduces retinal neovascularization in mice. Mol Vis, 2004, 10:468-75.
6. Clauss M. Molecular biology of the VEGF and VEGF receptor family. Semin Thromb Hemost, 2000, 26:561-9.
7. Eric A P, Robert L A, Eliot D F, et al. Vascular endothelial growth factor/vascular permeability factor expression in a mouse model of retinal neovascularization. Proc. Natl. Acad. Sci, 1995, 92:905-9.
8. Lu P. Y. et al., Keystone Symposia, Molecular Targets for Cancer Therapy, (2003, p 219. Xu J. et al., Gene Suppression. (2003).
9. Lu, Patrick et al., (2002), *Cancer Gene Therapy*, Vol. 10, Supplement 1, 011.
10. Lu, Patrick Y et al., (2003), *Current Opinion in Molecular Therapeutics*, 5(3):225-234.
11. Cogoni C. et al., (2000), *Genes Dev* 10:638-643.
12. Guru T., (2000), *Nature* 404:804-808.
13. Hammond S M et al., (2001), *Nature Rev Gen* 2:110-119.
14. Napoli C et al., (1990), *Plant Cell* 2:279-289.
15. Jorgensen R A et al., (1996), *Plant Mol Biol*, 31:957-973.
16. Ingelbrecht I et al., (1994), *Proc Natl Acad Sci USA*, 91:10502-10506.
17. Cogoni C et al., *EMBO J*, 15:3153-3163.
18. Palauqui J C et al., (1998), *EMBO J*, 16:4738-4745.
19. Guo S et al., (1995), *Cell*, 81:611-620.
20. Fire A et al., (1998), *Nature* 391:806-811.
21. Timmons L. et al., (1998), *Nature* 395:854.
22. Timmons L. et al., (2001), *Gene* 263:103-112.
23. Hunter C P, (2000), *Current Biology* 10:R137-R140.
24. Tabara H et al., (1998), *Science* 282:430-431.
25. Kamath R S et al., (2000), *Genome Biology* 2:2.1-2.10.
26. Grishok A et al., (2000), *Science* 287:2494-2497.
27. Sharp P A et al., (2000), *Science* 287:2431-2433.
28. Sharp P A, (2001), *Genes Dev* 15:485-490.
29. Kennerdell J R et al., (1998), *Cell* 95:1017-1026.
30. Kennerdell J R et al., (2000), *Nature Biotech* 18:896-898.
31. Dzitoyeva S et al., (2001), *Mol Psychiatry* 6(6):665-670.

32. Worby C A et al., (2001), *Sci STKE* Aug. 14, 2001(95): PL1.
33. Schmid A et al., (2002), *Trends Neurosci* 25(2):71-74.)
34. Hamilton A. J. et al., (1999), *Science* 286:950-952.
35. Hammond S et al., (2000), *Nature,* 404:293-298.
36. Zamore P D et al., (2000), *Cell* 101:25-33.
37. Hutvagner G et al., (2002), *Curr Opin Genetics & Development* 12:225-232.
38. Bernstein E et al., (2001), *Nature* 409:363-366.
39. Nykanen A et al., (2001), *Cell* 107:309-321.
40. Lipardi C et al., (2001), *Cell* 107:297-307.
41. Ketting R F et al., (1999), *Cell* 99:133-141.
42. Grishok A et al., (2001), *Cell* 106:23-34.
43. Hutvagner G et al., (2001), *Science* 293(5531):834-838.
44. Ketting R F et al., (2001), *Genes Dev* 15(20):2654-2659.
45. Lagos-Quintana M et al., (2001), *Science* 294:853-858.
46. Lau N C et al., (2001), *Science* 294:858-862.
47. Lee R C et al., (2001), *Science* 294:862-864.
48. Ruvkun G., (2001), *Science* 294:797-799.
49. Manche L et al., (1992), *Mol. Cell. Biol.* 12:5238-5248.
50. Minks M A et al., (1979), *J. Biol. Chem.* 254:10180-10183.
51. Yang S et al., (2001), *Mol. Cell. Biol.* 21(22):7807-7816.
52. Paddison P J et al., (2002), *Proc. Natl. Acad. Sci. USA* 99(3):1443-1448. Elbashir S M et al., (2001), *Genes Dev* 15(2):188-200.
53. Elbashir S M et al., (2001), *Nature* 411:494-498.
54. Caplen N J et al., (2001), *Proc. Natl. Acad. Sci. USA* 98:9746-9747.
55. Holen T et al., (2002), *Nucleic Acids Research* 30(8):1757-1766.
56. Elbashir S M et al., (2001), *EMBO J* 20:6877-6888.
57. Jarvis R A et al., (2001), *TechNotes* 8(5):3-5.
58. Brown D et al., (2002), *TechNotes* 9(1):3-5.
59. Brummelkamp T R et al., (2002), *Science* 296:550-553.
60. Lee N S et al., (2002), *Nature Biotechnol.* 20:500-505.
61. Miyagishi M et al., (2002), *Nature Biotechnol.* 20:497-500.
62. Paddison P J et al., (2002), *Genes & Dev.* 16:948-958.
63. Paul C P et al., (2002), *Nature Biotechnol.* 20:505-508.
64. Sui G et al., (2002), *Proc. Natl. Acad. Sci. USA* 99(6):5515-5520.
65. Yu J-Y et al., (2002), *Proc. Natl. Acad. Sci. USA* 99(9):6047-6052.
66. McCaffrey, A. P. et al., (2002), *Nature,* Vol. 418, July, 2002.
67. Watanabe A, Taniguchi M. (2005). A case of oropharyngeal cancer with multiple bone metastases from prostate cancer that responded to docetaxel, ifosfamide and cisplatin combination therapy. Gan To Kagaku Ryoho, 32(1):65-7.
68. Miner J, Gillan M M, Alex P, Centola M. (2005). Steroid-Refractory Ulcerative Colitis Treated with Corticosteroids, Metronidazole and Vancomycin: a Case Report. BMC Gastroenterol. 5(1):3.
69. Orbay E, Sargin M, Sargin H, Gozu H, Bayramicli O U, Yayla A. (2004). Addition of rosiglitazone to glimepirid and metformin combination therapy in type 2 diabetes. Endocr J. 51(6):521-7.
70. Smith L E, Wesolowski E, Mclellan A, et al. Oxygen-induced retinopathy in the mouse. Invest Opthalmol Vis Sci, 1994, 35:101-11.

TABLE B1-1 human VEGF specific siRNA sequences (25 basepairs with blunt ends):

| | | |
|---|---|---|
| VEGF-1, | CCUGAUGAGAUCGAGUACAUCUUCA | (SEQ ID NO: 276) |
| VEGF-2, | GAGUCCAACAUCACCAUGCAGAUUA | (SEQ ID NO: 277) |
| VEGF-3, | AGUCCAACAUCACCAUGCAGAUUAU | (SEQ ID NO: 278) |
| VEGF-4, | CCAACAUCACCAUGCAGAUUAUGCG | (SEQ ID NO: 279) |
| VEGF-5, | CACCAUGCAGAUUAUGCGGAUCAAA | (SEQ ID NO: 280) |
| VEGF-6, | GCACAUAGGAGAGAUGAGCUUCCUA | (SEQ ID NO: 281) |
| VEGF-7, | GAGAGAUGAGCUUCCUACAGCACAA | (SEQ ID NO: 282) |

TABLE B1-3 human VEGFR1 specific siRNA sequences (25 basepairs with blunt ends):

| | | |
|---|---|---|
| VEGFR1-1, | CAAAGGACUUUAUACUUGUCGUGUA | (SEQ ID NO: 283) |
| VEGFR1-2, | CCCUCGCCGGAAGUUGUAUGGUUAA | (SEQ ID NO: 284) |
| VEGFR1-3, | CAUCACUCAGCGCAUGGCAAUAAUA | (SEQ ID NO: 285) |
| VEGFR1-4, | CCACCACUUUAGACUGUCAUGCUAA | (SEQ ID NO: 286) |
| VEGFR1-5, | CGGACAAGUCUAAUCUGGAGCUGAU | (SEQ ID NO: 287) |
| VEGFR1-6, | UGACCCACAUUGGCCACCAUCUGAA | (SEQ ID NO: 288) |
| VEGFR1-7, | GAGGGCCUCUGAUGGUGAUUGUUGA | (SEQ ID NO: 289) |
| VEGFR1-8, | CGAGCUCCGGCUUUCAGGAAGAUAA | (SEQ ID NO: 290) |
| VEGFR1-9, | CAAUCAAUGCCAUACUGACAGGAAA | (SEQ ID NO: 291) |
| VEGFR1-10, | GAAAGUAUUUCAGCUCCGAAGUUUA | (SEQ ID NO: 292) |

TABLE B1-5 human VEGFR2 specific siRNA sequences (25 basepairs with blunt ends):

| | | |
|---|---|---|
| VEGFR2-1, | CCUCGGUCAUUUAUGUCUAUGUUCA | (SEQ ID NO: 293) |
| VEGFR2-2, | CAGAUCUCCAUUUAUUGCUUCUGUU | (SEQ ID NO: 294) |
| VEGFR2-3, | GACCAACAUGGAGUCGUGUACAUUA | (SEQ ID NO: 295) |
| VEGFR2-4, | CCCUUGAGUCCAAUCACACAAUUAA | (SEQ ID NO: 296) |
| VEGFR2-5, | CCAUGUUCUUCUGGCUACUUCUUGU | (SEQ ID NO: 297) |
| VEGFR2-6, | UCAUUCAUAUUGGUCACCAUCUCAA | (SEQ ID NO: 298) |

TABLE B1-5-continued human VEGFR2 specific siRNA sequences (25 basepairs with blunt ends):

| | | |
|---|---|---|
| VEGFR2-7, | GAGUUCUUGGCAUCGCGAAAGUGUA | (SEQ ID NO: 299) |
| VEGFR2-8, | CAGCAGGAAUCAGUCAGUAUCUGCA | (SEQ ID NO: 300) |
| VEGFR2-9, | CAGUGGUAUGGUUCUUGCCUCAGAA | (SEQ ID NO: 301) |
| VEGFR2-10, | CCACACUGAGCUCUCCUCCUGUUUA | (SEQ ID NO: 302) |

TABLE B1-7 human EGF specific siRNA sequences (25 basepairs with blunt ends):

| | | |
|---|---|---|
| EGF-1, | CAGGUAUUUCUUACUGGCUUCCAAA | (SEQ ID NO: 303) |
| EGF-2, | GCUGGUGUCUCAGUGAUCAUGGAUU | (SEQ ID NO: 304) |
| EGF-3, | CAGAUCUCGAUGGUGUGGGAGUGAA | (SEQ ID NO: 305) |
| EGF-4, | GAUGGAGGUUCUGUCCACAUUAGUA | (SEQ ID NO: 306) |
| EGF-5, | GCCAAGAGAUUAUUCUGGACUGAUA | (SEQ ID NO: 307) |
| EGF-6, | CGAUGCCAAGCAGUCUGUGAUUGAA | (SEQ ID NO: 308) |
| EGF-7, | UGGCAGGUGGUGAAGUUGAUCUAAA | (SEQ ID NO: 309) |

TABLE B1-7-continued human EGF specific siRNA sequences (25 basepairs with blunt ends):

| | | |
|---|---|---|
| EGF-8, | GCGAAGCUUUCAUAUGCCCUCCUAU | (SEQ ID NO: 310) |
| EGF-9, | UCUCUACGACUAAUCACCUACUCAA | (SEQ ID NO: 311) |
| EGF-10, | CACUGCAGUCUUAUUUCCAAGUAAG | (SEQ ID NO: 312) |

TABLE B1-9 human EGFR specific siRNA sequences (25 basepairs with blunt ends):

| | | |
|---|---|---|
| EGFR-1, | CACAGUGGAGCGAAUUCCUUUGGAA | (SEQ ID NO: 313) |
| EGFR-2, | CGCAAAGUGUGUAACGGAAUAGGUA | (SEQ ID NO: 314) |
| EGFR-3, | CGCAGCAUGUCAAGAUCACAGAUUU | (SEQ ID NO: 315) |
| EGFR-4, | CAGAAGGAGGCAAAGUGCCUAUCAA | (SEQ ID NO: 316) |
| EGFR-5, | GCCUAUCAAGUGGAUGGCAUUGGAA | (SEQ ID NO: 317) |
| EGFR-6, | CCAAGUCCUACAGACUCCAACUUCU | (SEQ ID NO: 318) |
| EGFR-7, | UCUCUGAGUGCAACCAGCAACAAUU | (SEQ ID NO: 319) |
| EGFR-8, | CAGCUUCUUGCAGCGAUACAGCUCA | (SEQ ID NO: 320) |
| EGFR-9, | GAAGCCAAGCCAAAUGGCAUCUUUA | (SEQ ID NO: 321) |
| EGFR-10, | UACAGAAACGCAUCCAGCAAGAAUA | (SEQ ID NO: 322) |

---

What is claimed is:

1. A small interfering RNA (siRNA) molecule, wherein the siRNA is double-stranded and consists of a sense strand consisting of the sequence CACAGUGGAGCGAAUUCCU-UUGGAA (SEQ ID NO: 313) and an anti-sense strand consisting of the complement of CACAGUGGAGCGAA-UUCCUUUGGAA (SEQ ID NO: 313) and wherein the siRNA reduces EGFR expression in a cell.

2. The siRNA molecule of claim 1, comprising at least one nucleotide that is chemically modified.

3. The siRNA molecule of claim 2, wherein the at least one chemically modified nucleotide is a nucleotide comprising a 2'-O-methyl ribose.

4. The siRNA molecule of claim 2, wherein the at least one chemically modified nucleotide is in the sequence in SEQ ID NO: 313.

5. The siRNA molecule of claim 2, wherein the at least one chemically modified nucleotide is in the complement of the sequence in SEQ ID NO: 313.

6. A composition comprising the siRNA molecule of claim 1 and a pharmaceutically acceptable carrier.

7. The composition of claim 6, further comprising one or more additional nucleic acid molecules that induce RNA interference and decrease the expression of a gene of interest.

8. The composition of claim 7, wherein at least one of the one or more additional nucleic acid molecules decreases the expression of a gene selected from the group consisting of VEGF, VEGFR1, VEGFR2, VEGFR3, PDGF, PDGFR-α, PDGFR-β, EGF, EGFR, RAF-a, RAF-c, AKT, RAS, NFkB, HIF, bFGF, bFGFR, Her-2, c-Met, c-Myc and HGF.

9. The composition of claim 6, wherein the carrier is a nucleic acid delivery vehicle.

10. The composition of claim 9, wherein the nucleic acid delivery vehicle is synthetic.

11. The composition of claim 10 wherein the synthetic nucleic acid delivery vehicle comprises a cationic polymer-siRNA complex.

12. The composition of claim 11, wherein the cationic polymer is a histidine-lysine co-polymer.

13. The composition of claim 11, wherein the synthetic nucleic acid delivery vehicle further comprises a hydrophilic polymer.

14. The composition of claim 13, wherein the hydrophilic polymer comprises a component selected from the group consisting of: polyethylene glycol, a polyacetal and a polyoxazoline.

15. The composition of claim 10, wherein the synthetic nucleic acid vehicle further comprises a targeting moiety.

16. The composition of claim 15, wherein the targeting moiety binds a tumor specific molecule or an angiogenesis-specific molecule.

17. The composition of claim 6 comprising an additional therapeutic agent selected from the group consisting of: an anti-cancer agent, an anti-inflammatory agent and an anti-infective agent.

18. The composition of claim 6 comprising an additional anti-angiogenic agent.

19. A 25 base pair, blunt-ended siRNA molecule that is double-stranded and comprises a sense strand and an anti-sense strand, wherein the antisense strand consists of the complement of the sequence in SEQ ID NO: 313 and wherein the siRNA reduces EGFR expression in a cell.

20. The siRNA molecule of claim 19, comprising at least one nucleotide that is chemically modified.

21. The siRNA molecule of claim 20, wherein the at least one chemically modified nucleotide is a nucleotide comprising a 2'-O-methyl ribose.

22. The siRNA molecule of claim 20, wherein the at least one chemically modified nucleotide is in the sense strand.

23. The siRNA molecule of claim 20, wherein the at least one chemically modified nucleotide is in the antisense strand.

24. A composition comprising the siRNA molecule of claim 19 and a pharmaceutically acceptable carrier.

25. The composition of claim 24, wherein the composition comprises a cationic polymer.

26. The composition of claim 25, wherein the cationic polymer is a histidine-lysine co-polymer.

27. The composition of claim 24, wherein the composition comprises a hydrophilic polymer.

28. The composition of claim 24, wherein the composition comprises a targeting ligand.

29. A siRNA molecule, wherein the siRNA is double-stranded and consists of a sense strand consisting of the sequence CACAGUGGAGCGAAUUCCUUUGGAA (SEQ ID NO: 313), optionally with an overhang of one to four nucleotides and an anti-sense strand consisting of the complement of CACAGUGGAGCGAAUUCCUUUGGAA (SEQ ID NO: 313), optionally with an overhang of one to four nucleotides and wherein the siRNA reduces EGFR expression in a cell.

* * * * *